United States Patent [19]
Watanabe et al.

[11] Patent Number: 5,674,741
[45] Date of Patent: *Oct. 7, 1997

[54] APPARATUS FOR MANUFACTURE OF BLOOD PRODUCTS AND METHOD FOR MANUFACTURE OF BLOOD PRODUCTS

[75] Inventors: Takahiko Watanabe; Nobukazu Tanokura; Norio Hosono; Noboru Ishida, all of Shizuoka, Japan

[73] Assignee: Terumo Kabushiki Kaisha, Tokyo, Japan

[ * ] Notice: The term of this patent shall not extend beyond the expiration date of Pat. No. 5,518,575.

[21] Appl. No.: 255,919

[22] Filed: Jun. 7, 1994

[30] Foreign Application Priority Data

| Jun. 7, 1993 | [JP] | Japan | 5-164048 |
| Aug. 27, 1993 | [JP] | Japan | 5-235564 |
| Dec. 9, 1993 | [JP] | Japan | 5-341542 |

[51] Int. Cl.$^6$ ............................. C12M 1/36; C12M 1/00
[52] U.S. Cl. ............ 435/283.1; 435/2; 435/286.5; 422/100; 422/101; 141/114; 604/410; 156/503; 156/494
[58] Field of Search ............... 435/2, 283.1, 286.5, 435/308.1; 210/782, 781, 361, 512.1; 141/10, 83, 114; 604/408, 410; 422/63–67, 100, 101, 102, 99; 156/503, 494, 499

[56] References Cited

U.S. PATENT DOCUMENTS

| 2,483,924 | 10/1949 | Moulinier . |
| 3,619,568 | 11/1971 | Taplin . |
| 4,024,010 | 5/1977 | Boccia . |
| 4,068,998 | 1/1978 | Attucci et al. . |

(List continued on next page.)

FOREIGN PATENT DOCUMENTS

| 0 122 772 | 10/1984 | European Pat. Off. . |
| 0 416 495 | 3/1991 | European Pat. Off. . |
| 0 471 953 | 2/1992 | European Pat. Off. . |
| 0 611 581 | 8/1994 | European Pat. Off. . |

(List continued on next page.)

OTHER PUBLICATIONS

M. Vogelsanger, "Robots: future key elements in laboratory automation", *Chemometrics and Intelligent Laboratory Systems: Laboratory Information Management*, 17 (1992), pp. 107–109.

*Primary Examiner*—William H. Beisner
*Attorney, Agent, or Firm*—Burns, Doane, Swecker & Mathis, LLP

[57] ABSTRACT

This invention concerns an apparatus and a method for the manufacture of blood products which are aimed at attaining the manufacture of blood products automatically and rationally with the operational efficiency enhanced, the quality of blood products stabilized, and the safety of blood products exalted, which are characterized in that the tube of a first container and the tube of a second container are aseptically and automatically connected preparatorily to the transfer of a plurality of blood components obtained by the separation of blood in the first container to the second container and the blood components in the first container are transferred through the connected tubes to the second container by use of a blood component transferring device.

52 Claims, 35 Drawing Sheets

U.S. PATENT DOCUMENTS

| | | |
|---|---|---|
| 4,276,112 | 6/1981 | French et al. . |
| 4,369,779 | 1/1983 | Spencer ................................ 128/213 A |
| 4,372,681 | 2/1983 | Sallenbach . |
| 4,412,835 | 11/1983 | Spencer ........................................ 604/29 |
| 4,443,215 | 4/1984 | Smith ........................................ 604/29 |
| 4,507,119 | 3/1985 | Spencer ...................................... 604/280 |
| 4,516,971 | 5/1985 | Spencer ...................................... 604/280 |
| 4,521,263 | 6/1985 | Benin et al. ................................ 156/159 |
| 4,595,562 | 6/1986 | Liston et al. . |
| 4,610,670 | 9/1986 | Spencer ........................................ 604/29 |
| 4,619,642 | 10/1986 | Spencer ........................................ 604/29 |
| 4,795,281 | 1/1989 | Ulinski, Sr. et al. . |
| 4,857,713 | 8/1989 | Brown . |
| 4,909,949 | 3/1990 | Harmony et al. . |
| 4,978,505 | 12/1990 | Kertz ........................................ 422/63 |
| 5,050,651 | 9/1991 | Hejlesen ...................................... 141/114 |
| 5,055,408 | 10/1991 | Higo et al. . |
| 5,150,795 | 9/1992 | Nakayama et al. . |
| 5,229,074 | 7/1993 | Heath et al. ................................ 422/67 |
| 5,341,854 | 8/1994 | Zezulka et al. ............................ 141/114 |
| 5,518,575 | 5/1996 | Watanabe .................................. 156/503 |
| 5,554,253 | 9/1996 | Watanabe .................................. 156/503 |

FOREIGN PATENT DOCUMENTS

| | | |
|---|---|---|
| 0 623 450 | 11/1994 | European Pat. Off. . |
| 0 667 226 | 8/1995 | European Pat. Off. . |
| 1 577 625 | 8/1969 | France . |
| 2 321 440 | 3/1977 | France . |
| 2 401 011 | 3/1979 | France . |
| 2 625 320 | 6/1989 | France . |
| 60-68925 | 4/1985 | Japan . |
| 1-131644 | 5/1989 | Japan . |
| 2-144045 | 6/1990 | Japan . |
| 3-29660 | 2/1991 | Japan . |
| 1648831 | 5/1991 | U.S.S.R. ...................................... 141/114 |
| 753641 | 7/1956 | United Kingdom . |
| 2 174 149 | 10/1986 | United Kingdom . |
| WO 86/04818 | 8/1986 | WIPO . |
| WO 86/04829 | 8/1986 | WIPO . |
| 90/15631 | 12/1990 | WIPO ........................................ 210/782 |

FIG. 32
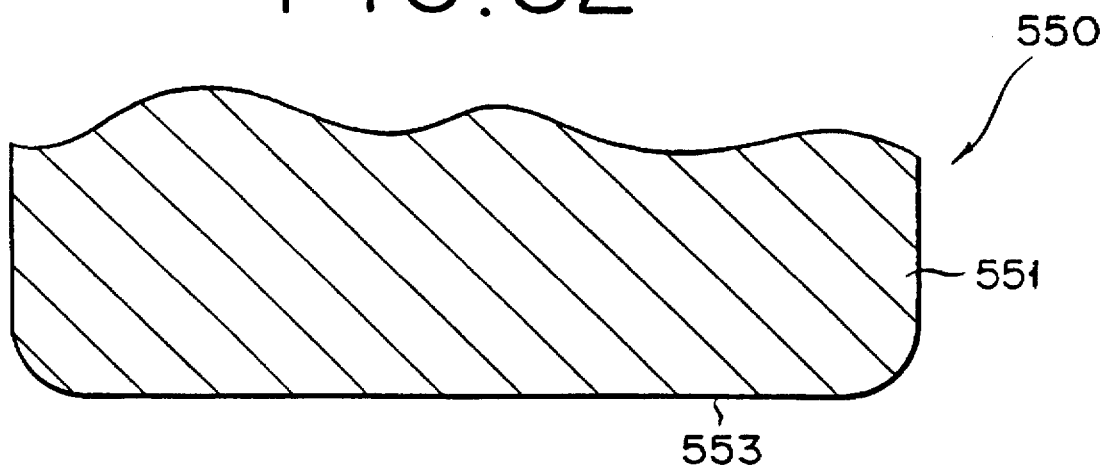
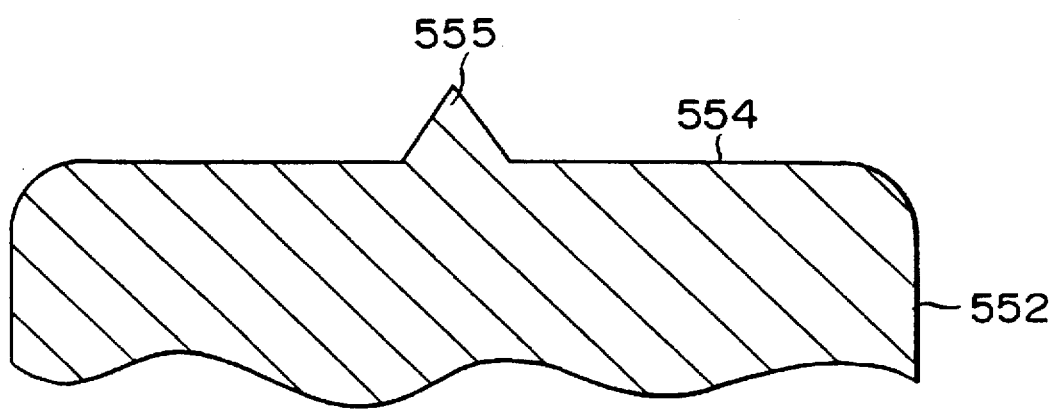
FIG. 33
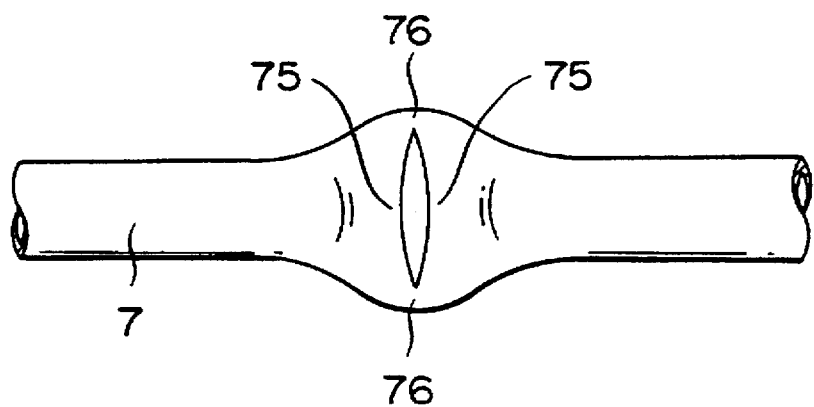

APPARATUS FOR MANUFACTURE OF BLOOD PRODUCTS AND METHOD FOR MANUFACTURE OF BLOOD PRODUCTS

BACKGROUND OF THE INVENTION

1. Field of the Invention

This invention relates to an apparatus for the manufacture of blood products and a method for the manufacture of blood products.

2. Description of the Prior Art

In the transfusion of blood to a patient, the practice of separating the blood obtained from a donor into various blood components as by centrifugation and transfusing only necessary blood components into the patient is prevailing today for such reasons as efficient utilization of blood and relief of the patient from the otherwise possible burden.

The manufacture of blood products to be used for the componential transfusion is accomplished by preparing a multiple bag (compound bag) comprising a plurality of flexible bags and tubes interconnecting the flexible bags, centrifuging at least once the compound bag containing blood thereby separating the blood into the three components, namely concentrated red blood cells, concentrated blood platelets, and platelet deficient blood plasma, transferring the concentrated blood platelets and the platelet deficient blood plasma out of the three components via tubes respectively into a blood platelet storage bag and a blood plasma storage bag, and separating the component bags of the compound bag asunder by fusing proper portions of the tubes and making cuts in the fused portions of the tubes.

The series of works just mentioned is substantially wholly carried out manually. By this reason or owing to the use of the multiple bag, the procedure entails various drawbacks as described below.

When a blood center adopts for blood preparation a procedure which ranges from blood collection through manufacture of blood products, for example, it is required to draw up a rough plan for blood collection and prepare a necessary number of bags severally proper in kind and shape. In this case, the bags are known in numerous kinds including a single bag, a two-piece bag, a three-piece bag, a four-piece bag, and so on. Likewise, the bags for blood collection are known in numerous forms (in terms of construction and capacity of bag and number of connecting tubes to be used, for example). The blood center, therefore, is forced to spend time and labor appreciably in preparing itself for the blood collection. It is possibly prevented from securing blood components in necessary amounts or compelled to waste surplus blood as when the plan for blood collection is changed or when the plan does not conform to the actual state of the site of blood collection. In an extreme case, it must wastefully discard such bags as are left unused.

Further, prior to the blood collection, the staff engaging in blood collection must select bags of suitable kind and shape mentioned above and confirm the fitness of the actually selected bags. During the manufacture of blood products, the work of separating the blood into the components thereof, the work of transferring the components to the relevant component bags, etc. vary with the kind and form of the bags. Thus, the works are highly complicated and prone to errors.

Besides, the multiple bag is so constructed that in the process of manufacture of blood products, the component bags thereof are kept in an interconnected state until they are separated asunder. While the multiple bag is being transported or handled, therefore, it is at a disadvantage in having the component bags thereof interfere with one another.

Particularly when the separation of blood into the components thereof is effected by use of a centrifuge, it entails various drawback as follows. Firstly, since the blood bag containing the collected blood and other bags are bundled, then set jointly in a auxiliary cup, and subsequently subjected to centrifugation, it is not easy to place these bags in the cup and eventually remove therefrom. Secondly, when the bags are stowed in the auxiliary cup, a dead space occurs in the bottom part of the cup and possibly causes the bags to sustain an injury due to the pressure of centrifugation. Thirdly, since the defects of the first and the second reasons mentioned above gain in conspicuity proportionately to the number of bags, the frequency of inferior centrifugation reaches to a point where the standardization of works and the stabilization of quality of products are will not be attained. Fourthly, the centrifugation lacks efficiency of operation because the ideal conditions of centrifugation vary with the kind and form of bags discussed above and the operation of centrifugation must be performed on the bags of a particular kind to ensure balance in weight of the rotor of a centrifuge in use of the occasion.

After the centrifugation, the blood bags are manually extracted from the centrifuge, transported, and set to a device or an apparatus which is adapted to transfer the separated components of blood. If, in this case, the bags happen to be shaken or swung, the boundaries of separated components of blood will be disturbed possibly to the extent of degrading the yields of produced blood components (degradation of the ratios of removal of other components). Particularly when the ratio of removal of white blood cells from the blood products is degraded, this degradation brings about the disadvantage of exalting the probability of infection with hepatitis virus, AIDS virus, etc. If the boundaries of the separated components of blood are heavily disturbed, the blood products to be eventually manufactured from these components will have to be either discarded as defective or subjected to centrifugation.

Thus, the manual works mentioned above must be carried out with extreme advertence lest the boundaries of the separated components of blood should be disturbed. The advertence imposes an immune burden on the workers and impairs the efficiency with which the blood products are manufactured.

For the control operation of the bags containing the blood products so manufactured, labels displaying such information as name of product, blood type, serial number of manufacture, and date of manufacture are applied one each to the bags. Since this is a manual work necessitating human discretion, it possibly exposes the workers to the danger of using wrong labels on bags or misreading the information on labels. The positions of the pasted labels on the bags are so dispersed that the information displayed on the labels are difficult to read correctly and are apt to be misread. Thus, the control operation of the blood products contained in these bags cannot be proper and perfect. The information from these labels is the sole means of indicating the origin of manufacture of blood products. The attachment of a wrong label could end in a fatal accident to a patient. The mistake of this nature should never happen. The work of applying these labels to the bags containing blood products, therefore, dictates payment of meticulous attention and imposes an immense burden of the workers and jeopardizes all efforts to streamline the operation of manufacture of blood products.

SUMMARY OF THE INVENTION

This invention, produced for the purpose of solving the various problems encountered by the conventional techniques as described above, has for a primary object thereof the provision of an apparatus for the manufacture of blood products and a method for the manufacture of blood products which are capable of automating and rationalizing manufacture of blood products, exalting the efficiency of manufacture, imparting a stabilized quality to the manufactured blood products, and enhancing the avirulent properties of the products.

An apparatus for the manufacture of blood products which is contemplated by this invention for the purpose of accomplishing the blood mentioned above is characterized by comprising a blood component transferring device for transferring from a first container storing therein a plurality of separated blood components at least one of the plurality of blood components to a second container and a tube connecting device capable of aseptically connecting a first tube communicating with the first container to a second tube communicating with the second container and utilizing the tube connecting device for connecting the first tube to the second tube and the blood component transferring device for transferring the blood components stored in the first container to the second container through the interconnected first and second tubes.

The first container is a flexible bag and the blood component transferring device comprises compressing means adapted to compress the first container and expel the blood components therefrom.

The blood component transferring device comprises aspirating means adapted to aspirate the blood components from the first container.

The aspirating means is a roller pump.

The tube connecting device comprises a pair of retaining members capable of parallel retaining the first and the second tube, a heat plate exchangeably disposed between the two retaining members and adapted to fuse and cut the first and the second tube, and a tube sealing device for causing the two retaining members to move relatively to each other and joining the cut surfaces of the first and the second tube.

The tube connecting device comprises a tube loading device for seating the first and the second tube on the retaining members and the tube loading device comprises a conveying head provided with two chucks for chucking the tubes at mutually different positions and drive means for moving at least either of the two chucks and varying the distance intervening between the two chucks.

The tube connecting device comprises a tube shape retention device for depriving the first and the second tube of deformation imparted thereto in consequence of the interconnection thereof and the tube shape retention device comprises a tube inserting space for permitting insertion therethrough of tubes, a pair of pressing members severally provided with pressing surfaces for chucking the deformed part of the tubes, and drive means for moving the pressing surfaces in opposite directions relative to each other.

The tube sealing device is characterized by comprising a pair of heating heads for chucking the tubes and having a protuberance formed on the tube chucking surface of at least either of the heading heads.

The tube sealing device is characterized by comprising cutting means for cutting the sealed portions of the tubes.

The tubes are retained in place by a tube conveying device for conveying the tubes in the longitudinal direction thereof and the tube conveying device comprises conveying rails forming a passage for passing the tubes, at least one pair of rollers adapted to chuck and rotate the tubes, and drive means for rotating the rollers.

The tube conveying device comprises a tube pickup device for retaining the tubes in a taut state.

The first container is characterized by being so adapted as to be accommodated in a cup and in situ conveyed by a first container conveying device capable of a conveying motion to the blood component transferring device.

The cup is transparent or translucent.

The first container conveying device is characterized by comprising a rotary drive mechanism composed of a rotator, a plurality of cup retaining parts disposed in the peripheral part of the rotator and adapted to retain the cup in place, and rotary drive means for imparting a rotary driving motion to the rotator.

The first container conveying device is characterized by comprising a cup conveying mechanism for taking out the cups from a centrifuge and seating the cups in the cup retaining part.

The first container conveying device is characterized by being provided in the area of conveyance thereof with a first container recovery part for recovering the first container which has completed transfer of the blood component.

The second container is characterized by being seated in the container loading base and enabled as seated in the container loading base to convey the blood component from the first container.

The second container is an unused flexible bag supplied from a container feeding device and having the second tube connected thereto.

The container feeding device is characterized by comprising a bag accommodating part capable of accommodating bags as orderly superposed therein with the second tube sides thereof posed in one fixed direction, a mounting base disposed near the bottom part of the bag accommodating part and used for mounting the bags thereon, and a lift capable of imparting a vertical reciprocating motion to the mounting base and, thereby, enabling the mounting base to be elevated by the action of the lift and permitting the bags mounted on the mounting base to be supplied out successively from the upper side of the pile of bags downwardly.

The mounting base is characterized by being elevated at different ratios of elevation on the second tube side of the bags and on the side opposite thereto thereby enabled to impart a prescribed angle to the uppermost bag in the pile of bags accommodated in the bag accommodating part without reference to the number of bags so accommodated.

The mounting base is characterized by being rotatably disposed round one end part thereof and adapted so as to be rotated in consequence of an elevation thereof.

The mounting base is characterized by comprising a plurality of mounting pieces jointly forming a link mechanism and varying shape in consequence of an elevation thereof.

The lift comprises two drive mechanisms for elevating the mounting base at different ratios of elevation on one end side and on the other end side of the mounting base.

The second container supplied from the container feeding device is adapted to be conveyed by a second container conveying device to a prescribed position and the second container conveying device comprises a head provided with retaining means for retaining the second container in place and moving means for moving the head in at least two perpendicularly intersecting direction.

The retaining means comprises a suction cup for attracting fast thereto the second container by aspiration and decompression means for reducing the pressure within the suction cup.

The second container conveying device is provided within the conveying area thereof with at least one second container recovering case for recovering the second container which has completed conveyance of the blood component.

The first or the second tube is so adapted as to enable a liquid held therein to be moved therein by a tube squeeze device for imparting a squeezing action to the tube in the longitudinal direction thereof.

The tube squeeze device comprises a tube squeeze part composed of a roller and a counter member thereof, roller rotating means for rotating the roller, and displacing means for varying the distance between the roller and the counter member thereof and thereby utilizes the action of the displacing means for causing the roller and the counter member thereof to approach to each other and close the tube and, at the same time, utilizes the action of the roller rotating means for rotating the roller, squeezing the tube to a prescribed length, and moving the liquid in the tube.

The tube squeeze device is characterized by comprising a tube squeeze part composed of a roller and a counter member thereof, roller rotating means for rotating the roller, and displacing means for varying the distance between the roller and the counter member thereof, a container loading base for seating a flexible container having the tube attached thereto as allowed to communicate with the interior of the flexible container, and control means for controlling the actions of the roller rotating means and the displacing means and thereby enabling the control means to utilize the action of the displacing means for causing the roller and the counter member thereof to approach each other and compress and close the tube, the action of the roller rotating means for rotating the roller, squeezing the tube to prescribed length, and moving the liquid in the tube toward the container, and then the action of the roller rotating means for moving the roller and the counter member thereof away from each other and relieving the tube of the closure.

The tube squeeze device is characterized by comprising a tube squeeze part composed of a pair of rollers disposed as opposed to each other through the tube, roller rotating means for rotating at least either of the rollers, and displacing means for varying the distance between the rollers, a container loading base for seating a flexible container having the tube attached thereto as allowed to communicate with the interior of the flexible container, and control means for controlling the actions of the roller rotating means and the displacing means and thereby enabling and thereby enabling the control means to utilize the action of the displacing means for causing the two rollers to approach each other and compress and close the tube and, at the same time, the action of the roller rotating means for rotating the rollers and squeezing the tube to a prescribed length, and moving the fluid in the tube toward the container, and then the action of the roller rotating means for moving the two rollers away from each other and relieving the tube of the closure.

The tube squeeze device is characterized by comprising a tube squeeze part composed of a pair of rollers disposed as opposed to each other through the tube, roller rotating means for rotating at least either of the rollers, and displacing means for varying the distance between the rollers, a container loading base for seating a flexible container having the tube attached thereto as allowed to communicate with the interior of the flexible container, stirring means for stirring a liquid in the container seated on the container sealing part, and control means for controlling the actions of the displacing means and the stirring means and thereby enabling the control means to utilize the action of the displacing means for causing the two rollers to approach each other and compress and close the tube and, at the same time, the action of the roller rotating means for rotating the roller, squeezing the tube to a prescribed length, and moving the liquid in the tube toward the container, then the action of the stirring means for stirring the liquid in the container, and thereafter the action of the displacing means for moving the rollers away from each other and relieving the tube of the closure.

The stirring means is shaking means for shaking the container loading base.

The tube squeeze device terminates the squeezing action thereof exerted on the tube at a position near the joint between the tube and the first or the second container.

The tube squeeze device terminates the squeezing action thereof exerted on the tube at a position near the joint between the tube and the first or the second container.

The first container and/or the second container is adapted for allowing a chemical solution to be introduced therein by use of a chemical solution feeding device.

The chemical solution feeding device is characterized by comprising a chemical solution container storing the chemical solution and a third tube communicating with the chemical solution container and allowing the chemical solution in the chemical solution container to be transferred in a prescribed amount to the first container through said first and the third tube after the tube connecting device has interconnected the first and the third tube.

The transfer of the chemical solution is characterized by being effected by use of a roller pump.

The control means for controlling the component units of the apparatus for the manufacture of blood products comprises an data processing device for managing the information concerning the content of the first container.

The data processing device comprises a reader for reading an data code adapted to indicate the information concerning the content and attached to the first container.

The data code is a one-dimensional or a two-dimensional code.

The reader is characterized by being so adapted as to read optically the data code.

The reader is characterized by being so adapted as to read the data code in a flattened state.

The data processing device is characterized by comprising a label producing device for producing a label vested with the data code.

The label producing device is a printer for displaying the data code on a label.

The data processing device comprises a label application device for applying a label produced by the label producing device to the second container.

The label application device comprises a pressure head for applying the label fast with pressure to a surface and moving means for moving the pressure head in at least two perpendicularly intersecting directions.

The label has other information displayed thereon besides the information concerning the content.

The control means is characterized by being adapted for enabling the data processing device to utilize the reader for reading the data code attached to the first container, the label producing device for producing a label having attached thereto the data code carrying the information corresponding to the information read out by the reader, and the label application device for applying the label to the second container.

The data processing device comprising a check reader for reading the data code on the label.

The control means is characterized by being adapted for enabling the data processing device to utilize the reader for reading the data code attached to the first container, the label producing device for producing a label having attached thereto the data code carrying the information corresponding to the information read out by the reader, the label application device for applying the label to the second container, and the check reader for comparing the information read out thereby with the data code on the applied label with the information read out and confirming coincidence therebetween.

The control means is characterized by being adapted to give an alarm when it confirms the absence of the coincidence between the information read out by the reader and the information read out by the check reader.

The control means is characterized by comprising flow detecting means for detecting the amounts of a liquid flowing in and/or flowing out of the first container.

The control means is characterized by comprising weight detecting means for detecting a change in weight of the second container.

The weight detecting means is characterized by comprising overload releasing means for precluding exertion of an excessive load.

The first or the second container severally comprises one or more pieces.

A method for the manufacture of blood products which is contemplated by this invention for the purpose of accomplishing the object mentioned above effects automatically the manufacture of blood products by use of a plurality of blood components obtained by the separation of blood, which is characterized by comprising a tube connecting step of aseptically interconnecting a first tube communicating with a first container accommodating the blood therein to a second tube communicating with a second container and a step of transferring at least one of the plurality of separated blood components in the first container to the second container through the interconnected first and second tubes.

A method for the manufacture of blood products which is contemplated by this invention for the purpose of accomplishing the object mentioned above effects automatically the manufacture of blood products by use of a plurality of blood components obtained by the separation of blood, which is characterized by comprising a step of conveying a first container accommodating the blood therein to a blood component transferring device, a tube connecting step of aseptically interconnecting a first tube communicating with the first container accommodating the blood therein to a second tube communicating with a second container, and a step of transferring at least one of the plurality of separated blood components in the first container to the second container through the interconnected first and second tubes.

A method for the manufacture of blood products which is contemplated by this invention for the purpose of accomplishing the object mentioned above effects automatically the manufacture of blood products by use of a plurality of blood components obtained by the separation of blood, which is characterized by comprising a step of centrifugally separating the blood accommodated in the first container into a plurality of blood components, a step of conveying the first container to a blood component transferring device, a tube connecting step of aseptically interconnecting a first tube communicating with the first container accommodating the blood therein to a second tube communicating with a second container, and a step of transferring at least one of the plurality of blood components in the first container to the second container through the interconnected first and second tubes.

A method for the manufacture of blood products which is contemplated by this invention for the purpose of accomplishing the object mentioned above effects automatically the manufacture of blood products by use of a plurality of blood components obtained by the separation of blood, which is characterized by comprising a step of extracting an unused second container and disposing the second container on a container loading base, a tube connecting step of aseptically interconnecting a first tube communicating with the first container accommodating the blood therein to a second tube communicating with the second container, and a step of transferring at least one of the plurality of blood components in the first container to the second container through the interconnected first and second tubes.

A method for the manufacture of blood products which is contemplated by this invention for the purpose of accomplishing the object mentioned above effects automatically the manufacture of blood products by use of a plurality of blood components obtained by the separation of blood, which is characterized by comprising a tube connecting step of aseptically interconnecting a first tube communicating with a first container accommodating the blood therein to a second tube communicating with a second container, a step of eliminating deformation formed in the interconnected tubes in consequence of the interconnection, and a step of transferring at least one of the plurality of blood components in the first container to the second container through the interconnected first and second tubes.

The method further comprises a step of detecting the weight of the second container and adjusting the amount of the blood component to be transferred based on the numerical value obtained by the detection preparatorily to the transfer.

The method further comprises a step of squeezing the tube in the longitudinal direction thereof and moving a liquid in the tube.

The method further comprises a step of sealing the tube by fusion.

The method further comprises a step of cutting the sealed part of the tube after the tube has been sealed by fusion.

The method further comprises a step of supplying a chemical solution into the first container.

The transfer of the chemical solution is characterized by comprising a step of interconnecting a third tube communicating with a chemical solution containing storing the chemical solution to the first tube and a step of transferring the chemical solution in the chemical solution container in a prescribed amount to the first container through the first and third tubes.

The supply of the chemical solution is characterized by adjusting the amount of the chemical solution to be supplied in accordance with the amount of the blood components remaining in the first container.

The first or the second container severally comprises one or more pieces.

This invention, owing to the construction described above, enjoys the following advantages.

Since the conventional blood bags are notably diversified in kind (number of interconnected component bags, for example) and form (construction and capacity, for example), the preparation thereof for blood collection and the actual use thereof in blood collection have required very large amounts of time and labor. Frequently, blood components are obtained only in amounts short of necessary levels or excess blood is wasted inevitably as when the plan for blood collection is altered or when the plan does not coincide with the actual state of the site of blood collection. Not infrequently, blood bags elaborately obtained are discarded before use is found therefor. This invention allows use of all-purpose or unique bags. These bags, therefore, are readily prepared for blood collection and, prior to the blood collection, are neither required to be selected in terms of kind and form nor examined to confirm the fitness as to the kind and form. Thus, the use of these bags results in precluding the problem of shortage or oversupply of blood components mentioned above.

Further, since the bags are all-purpose or unique bags, they can be easily transported and handled. During the centrifugal separation, they can be easily set in place in a centrifuge and easily extracted therefrom. The possibility of these bags giving rise to a dead space in the bottom part of a auxiliary cup and consequently sustaining an injury due to the pressure of centrifugation is nil. The differences otherwise caused in the conditions of centrifugation by the conventional diverse kinds of bags cannot occur on the bags of unique kind and form contemplated by this invention. Besides, the centrifugation performed on the bags proceeds with high operational efficiency.

When the bags containing the separated blood components are being conveyed or the blood components contained in the bags are being transferred to other bags, the bags are inevitably shaken or stirred. Even then, the possibility of the boundaries of the separated blood components being disturbed to the extent of degrading the yields of the produced blood components (lowered ratios of removal of other components) is nil in the case of the bags of this invention.

Further, since the plurality of tubes to be used during the transfer of blood components are aseptically interconnected, the manufacture of blood products can be carried out effectively in a perfect closed system. The possibility of manufactured blood products contained in the bags being contaminated by microbes is nil.

The apparatus and method according to this invention allow standardization of works involved in the manufacture of blood products and uniformization and stabilization of products in quality. Particularly when they further use the function of detecting and/or adjusting the weights of blood components transferred and the amounts of chemical solutions added, their effects are further exalted.

When the apparatus of this invention is further furnished with an data processing device, the workers are spared the sever burden of paying a meticulous attention to the process control and are prevented from applying wrong labels to the bags or misreading the information on the labels. As a result, the operation of manufacture of blood products is prevented from causing accidents due to mistaken identification of blood type and moreover allowed to enjoy high safety.

Besides, when the apparatus is provided with control means capable of methodically aggregating the information to be read out, it permits the blood transfusion system to utilize comprehensive management of the information.

This invention enables the manufacture of blood products to proceed with exalted productivity by automating and streamlining the works involved therein. It also permits standardization of the works for the manufacture of blood products and stabilization of quality of the products. Particularly when the blood components offer a plurality of mutually different forms of transfer to choose, this invention permits the manufacture of blood products to be attained extensively, depending on the construction of blood bags and the amount of blood or blood products to be handled.

The invention will be better understood and the objects and features thereof other than those set forth above will become apparent when consideration is given to the following detailed description thereof, which makes reference to the annexed drawings.

BRIEF DESCRIPTION OF THE DRAWINGS

FIG. 32 is a cross section illustrating the essential part of a tube sealing device on a magnified scale.

FIG. 33 is a diagram illustrating the shape of a tube sealed by use of the tube sealing device.

DETAILED DESCRIPTION OF THE PREFERRED EMBODIMENT

Now, one working example of this invention will be described below with reference to the accompanying drawings.

Figure 1:
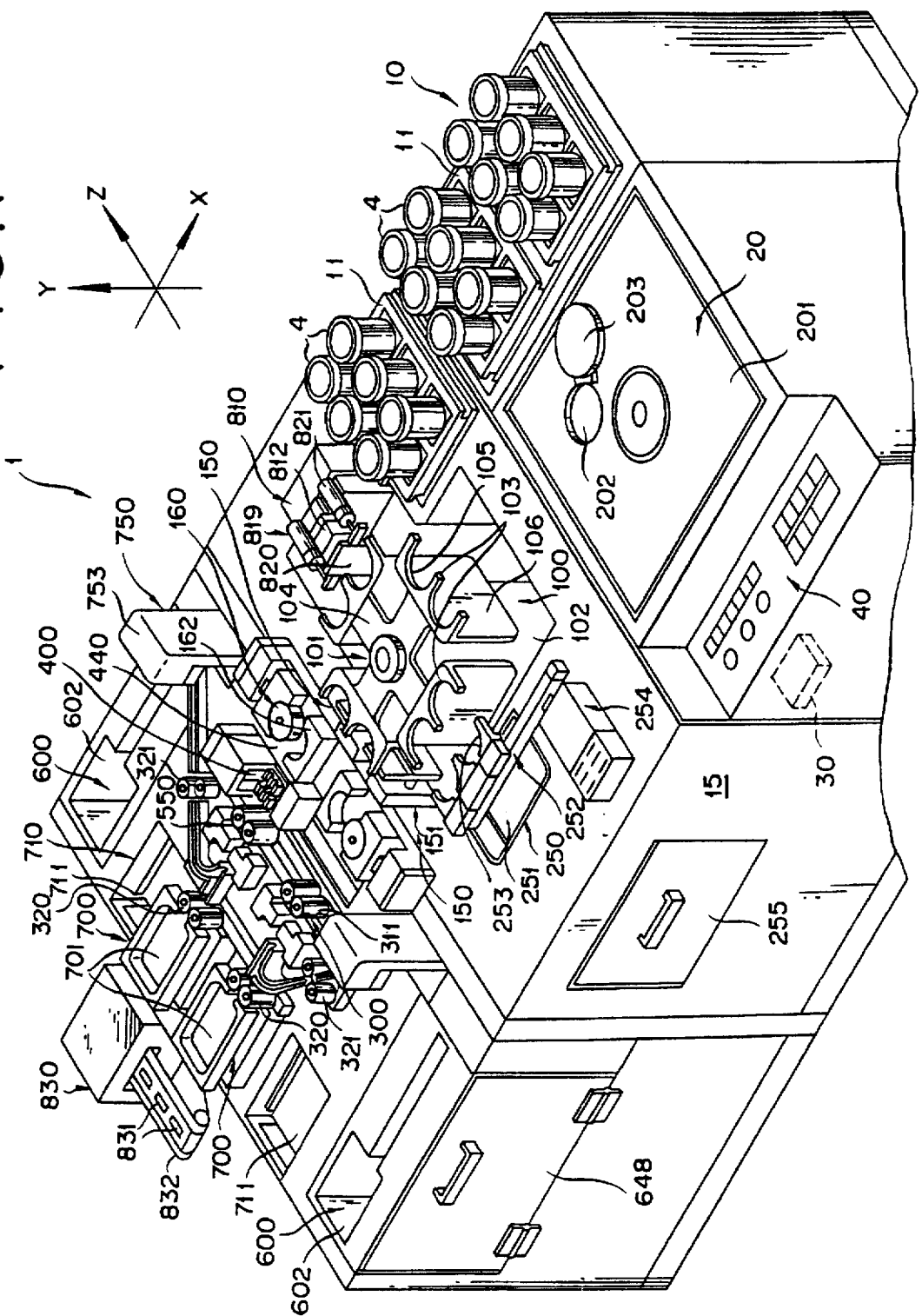
FIG. 1 is a schematic perspective view of an apparatus for manufacture of blood products as one embodiment of this invention.

FIG. 1 is a schematic perspective view illustrating an apparatus for the manufacture of blood products according to this invention. The part of the construction of the apparatus which is not shown in this diagram will be illustrated supplementarily in FIGS. 2 to 56. As illustrated in these drawings, an apparatus 1 for the manufacture of blood products contemplated by this invention comprises a container gathering case 10, a centrifuge 20, control means 30, an operator console 40, a first container conveying device 100, a blood component transferring device 150, a tube pickup device 200, a first container recovering case 250, a tube conveying device 300, a tube loading device 350, a tube connecting device 400, a tube shape retention device 450, a tube squeeze device 500, a tube sealing device 550, a container feeding device 600 or 601, a second container conveying device 650, a containing seating part 700, a second container recovering case 710, a chemical solution feeding device 750, and an data processing device 800. Now, the constructions of these component members of the apparatus will be described in order below.

The apparatus 1 for the manufacture of blood products is provided on one end side (frontal side in the bearings of FIG. 1) thereof with the container gathering case 10 and the centrifuge 20 adjoined thereto.

[Container gathering case 10]

On the container gathering case 10, three trays 11 are set in place. On each of the trays 11, a blood bag 2 or a first container accommodated in a cup 4 is seated in an erect state.

Figure 38:
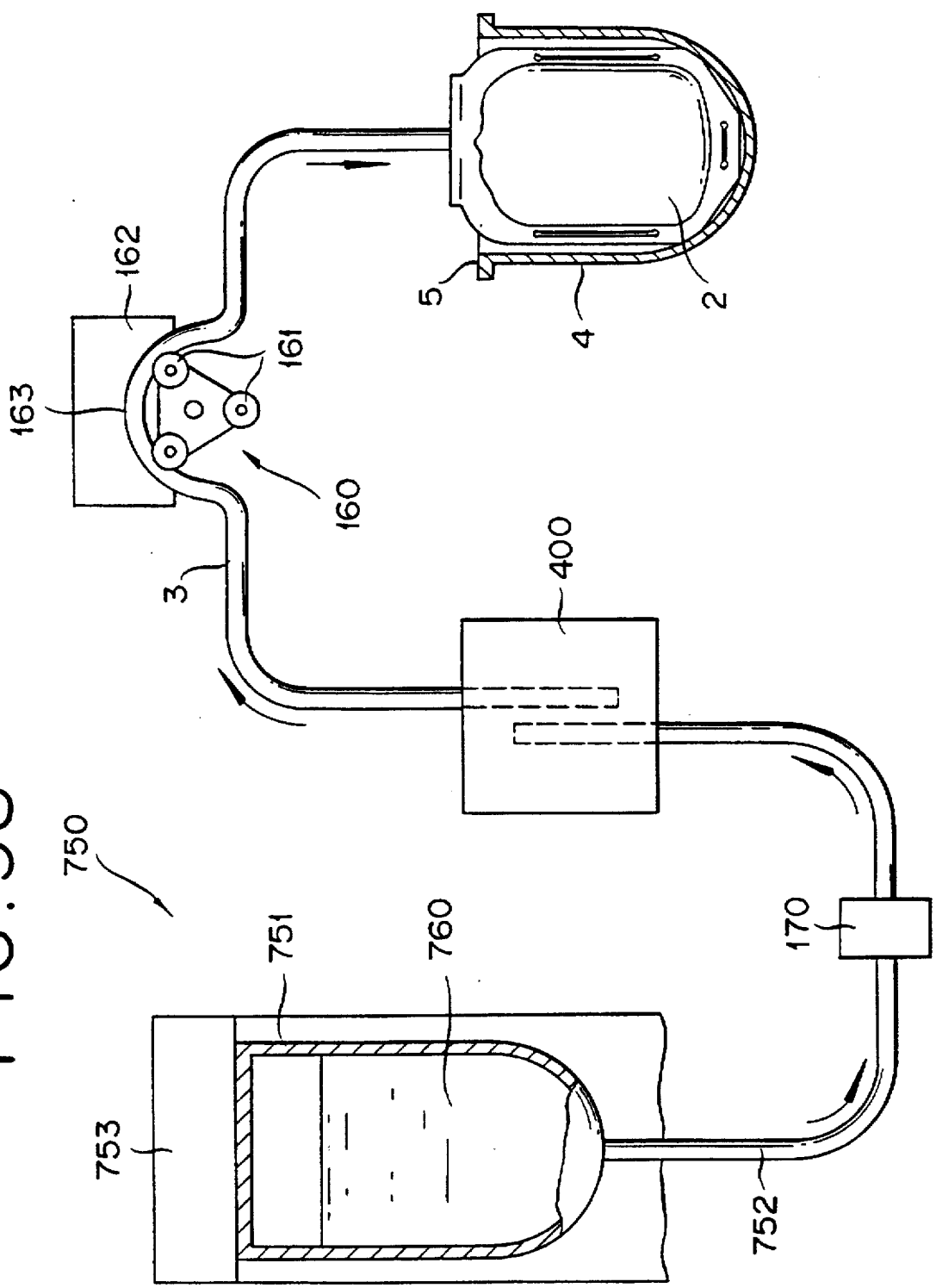
FIG. 38 is a circuit diagram illustrating in the form of a model the construction of circuits in a chemical solution feeding device.

The blood bag 2, as illustrated in FIG. 38, is obtained by superposing two resinous sheet materials such as of soft polyvinyl chloride and fusing the matched peripheral parts of the superposed sheet materials (thermal fusion, high frequency fusion, etc.). One end of a flexible tube 3 is connected to one end of the blood bag 2 in such a manner that the flexible tube 3 will communicate with the interior of the blood bag 2.

The cup 4 is a tubular member possessed of a curved bottom part. An annular rib 5 is formed on the edge part of the upper end opening of the cup 4. The part of the cup 4 excluding the rib 5 is made of a soft material. As concrete examples of the soft material, such thermoplastic elastomers as soft polyvinyl chloride, polyethylene, polypropylene, polyester, polyurethane, polyamide, silicone, polyester elastomer, polyamide elastomer, and styrene-butadiene-styrene copolymer may be cited.

The cup 4 is desired to be transparent or translucent so that an data code (bar code) attached to the blood bag 2 accommodated in the cup 4 will be read by a reader 810 which will be specifically described hereinbelow.

A tube retaining part (not shown) for retaining the end part of the tube 3 is formed in the upper part of the rib 5. This tube retaining part, for example, may be a groove or a chucking member in which the tube 3 fits. The end part of the tube 3 as retained in place by the tube retaining part is picked up by the tube pickup device 200 which will be specifically described hereinbelow.

The construction of the cup 4 does not need to be limited to what is illustrated in the drawing. Positioning means (not shown) which is capable of accommodating blood bags 1 invariably in one fixed direction relative to the cup 4 may be used instead. The cup 4 may be seated through a cylindrical erection auxiliary member (not shown) adapted to retain the cup 4 in an erected state instead of being directly seated on the tray 11.

The trays 11 may be so installed so as to be movable in the directions of X and Z shown in FIG. 1 for the purpose of enabling the cups 4 to be extracted at specific positions relative to the main body of the apparatus 15 when the cups 4 are extracted by a cup conveying mechanism which will be specifically described hereinbelow or when they are seated on the tray 11.

The trays 11 may be severally provided with means (weight sensor or touch sensor, for example) for discerning whether or not the trays 11 have installed the cups 4.

[Centrifuge 20]

The centrifuge 20 is provided therein with a rotor (not shown) which can be rotated at a high speed by rotary drive means. In this rotor, a plurality of hard auxiliary cups (not shown) allowing insertion therein of the cups 4 are disposed in a radial pattern. When the cups 4 holding the blood bags 2 are inserted in the auxiliary cups and the rotor is set rotating, the blood in the blood bags 2 is centrifugally separated into a plurality of blood components. The conditions (revolution number, duration of operation, for example) for centrifugation of the centrifuge 20 are set manually by use of an operator console 40 which will be described specifically hereinbelow) or automatically by the control means 30.

The upper side of the centrifuge 20 is covered with a ceiling plate 201. In this ceiling plate 201, a circular opening 202 allowing the cup 4 to be inserted therethrough is formed. When the cups 4 are set in place on the centrifuge 20 and extracted from the centrifuge 20 by use of a cup conveying mechanism 110 which will be specifically described herebelow, they are passed severally through these openings 202. When the cups 4 are set in place on the rotor of the centrifuge 20 and when they are extracted from the rotor after completion of the centrifugation, therefore, the control means 30 controls the rotor so that the rotor will rotate one pitch at a time (the angle of rotation equaling the interval separating the adjoining auxiliary cups) and the auxiliary cups seated on the rotor will be positioned directly below the openings 202.

While the centrifuge 20 is in operation, the openings 202 are kept closed with lids 203.

[First container conveying device 100]

In the substantially central part of the apparatus 1 for the manufacture of blood products, the blood component transferring device 150 for transferring the blood components in the blood bag 2 to a blood component bag 6 which is a second container and the first container conveying device 100 for conveying the blood bag 2 to the blood component transferring device 150 are installed.

Figure 5:
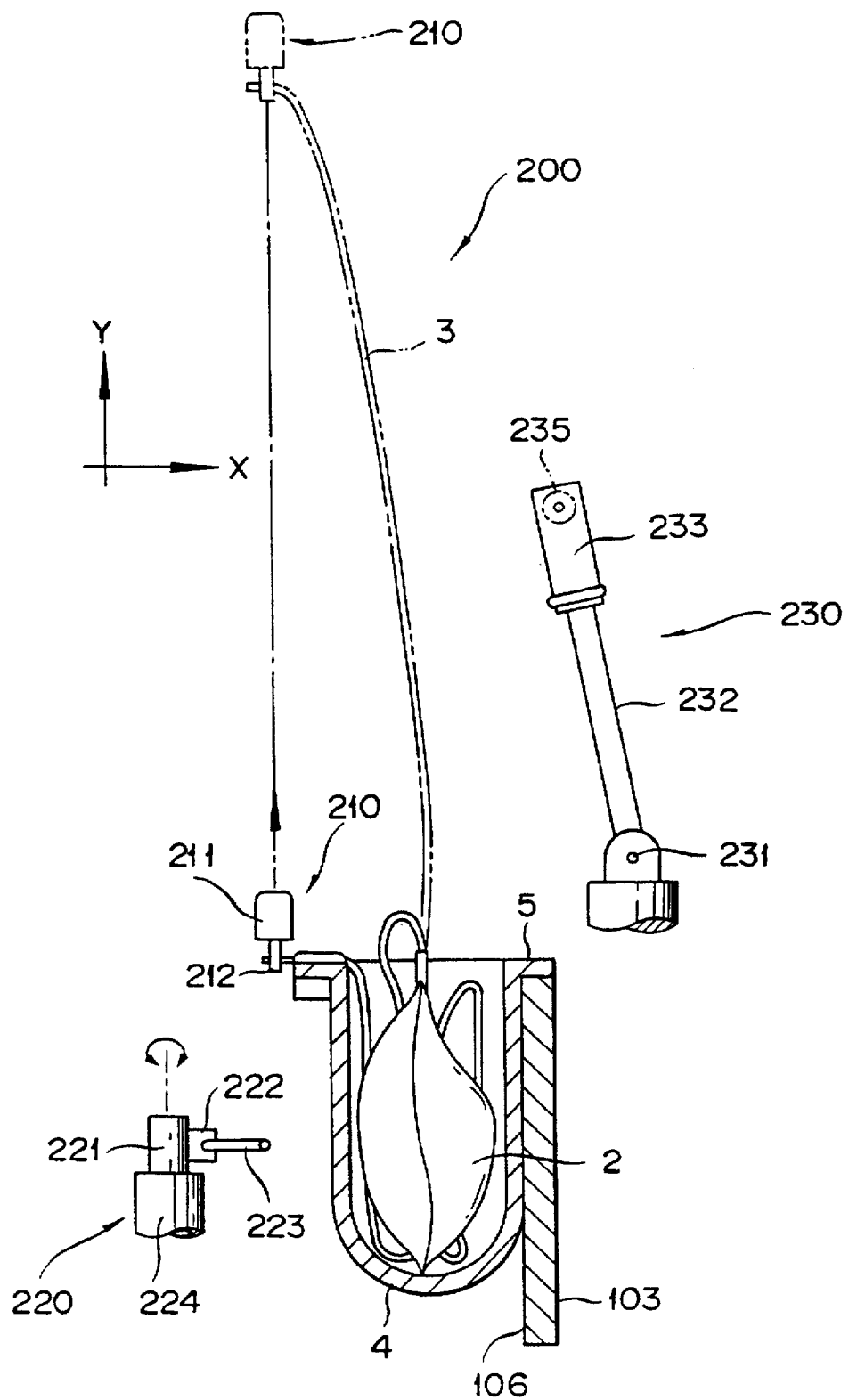
FIGS. 5 to 8 are partially sectioned side views each illustrating a tube pickup device.

The first container conveying device 100 is composed of a rotary conveying mechanism 101 and the cup conveying mechanism 110 (as shown in FIG. 5). In the present working example, the rotary conveying mechanism 101 is responsible mainly for the latter half of the conveyance and the cup conveying mechanism 110 for the former half of the conveyance. Now, the constructions of these component parts will be described in order below.

The rotary conveying mechanism 101 is composed of a rotator (turn table) 102 which is rotatably set in place relative to the main body 15 of the apparatus, cup retaining members 103 disposed in the peripheral part of the rotator 102 and adapted to retain the cup 4 in place, and rotary drive means (not shown) for rotationally driving the rotator 102.

A cruciform arm 104 is fixed in the upper part of the rotary shaft of the rotator 102. The cup retaining members 103 which are severally provided with two arcuate notches 105 are fixed one each of the four end parts of the arm 104. The cups 4 are suspended and retained in place by the cup retaining members 103 when the cups 4 are inserted into the notches 105 and, at the same time, the ribs 5 are fastened to the edge parts of the notches 105.

The rotary driving means for rotationally driving the rotator 102 is provided with a drive source like a motor and a reduction gear. The drive source is electrically connected to the control means 30 so that the drive thereof will be subject to the control means 30. For example, the drive source is powered by the control means 30 so as to rotate the rotator 102 by 90° in a prescribed direction at a prescribed time. In this case, the rotator 102 is rotated at a relatively low speed so that the rotation will not disturb the boundaries of the blood components separated inside the blood bag 2. When the rotation of the rotator 102 is started and when it is stopped, the drive of the rotator 102 is controlled so as to produce only an insignificant shock.

The cup conveying mechanism 110 is intended to take hold of the cups 4 for accommodating the blood bags 2 and conveying them to a prescribed destination. It does the work of setting on the rotor of the centrifuge 20 the cups 4 supported on the tray 11 which holds the blood bags 2 with full blood, the work of extracting the cups 4 which have undergone centrifugation from the centrifuge 20 and setting them in place on the tray 11, and the work of loading on the cup retaining member 103 the cups 4 installed on the tray 11.

Figure 2:
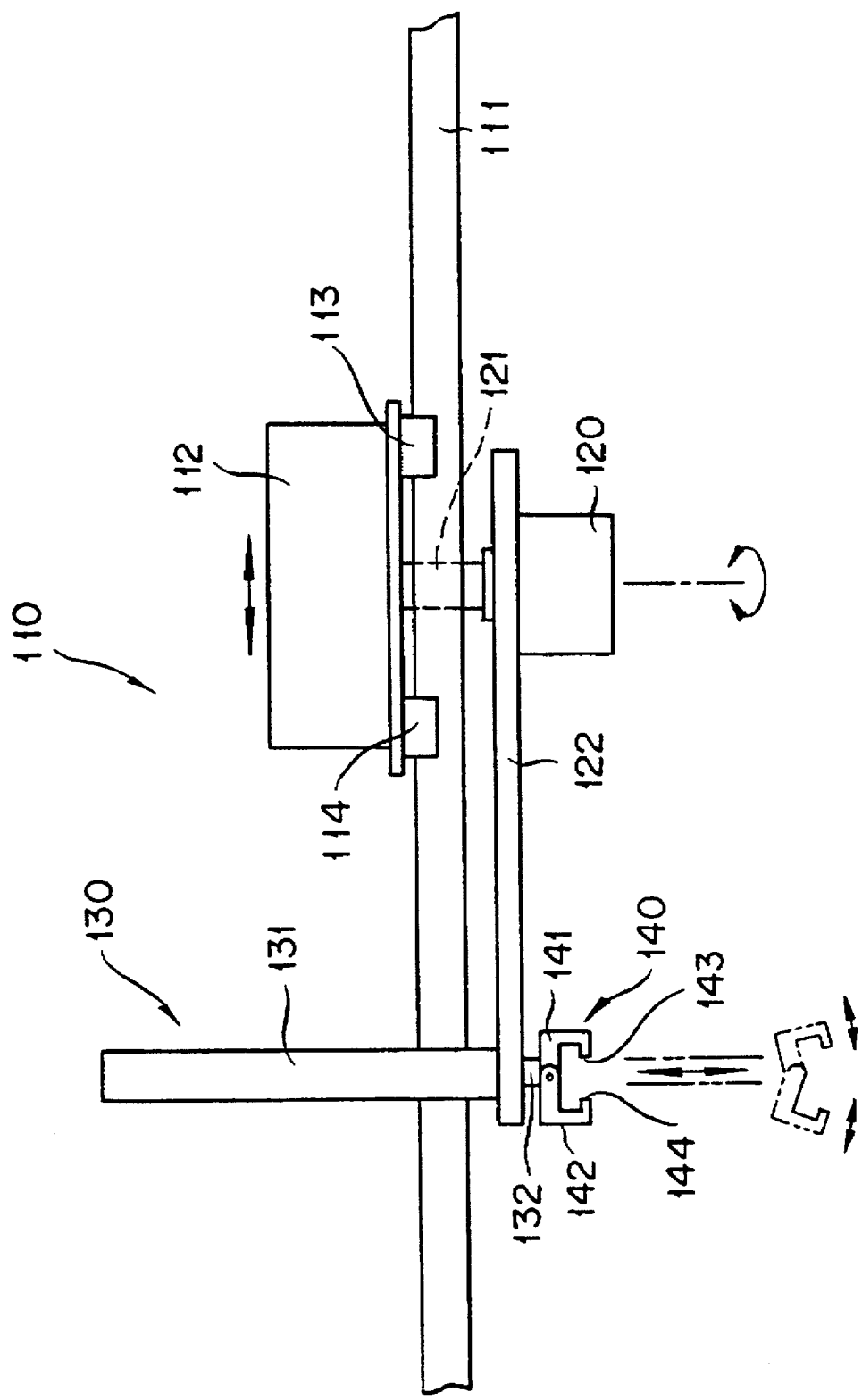
FIG. 2 is a side view illustrating a cup conveying mechanism.

FIG. 2 is a side view illustrating the cup conveying mechanism 110. As illustrated in this diagram, the cup conveying mechanism 110 comprises conveying rails 111, a moving member 112, a rotary transferring device 120, an elevation driving device 130, and a handling device 140. The conveying rails 111 are laid over the rotary conveying device 101, the containing gathering part 10, and the centrifuge 20 in the substantially central part of the area for conveyance of the cups 4.

The moving member 112 is mounted on the conveying rails 111 and reciprocated along the conveying rails 111. On the moving member 112, two pairs of rollers 113 and 114 for chucking the conveying rails 111 and a motor (not shown) for rotating these rollers 113 and 114 are installed. This motor can be normally and reversely rotated. When the rollers 113 and 114 are rotated by the action of the motor, the moving member 112 is moved within a prescribed range on the conveying rails 111.

The rotary transferring device 120 is disposed on the underside of the moving member 112. The rotary transferring device 120 is provided with a rotary driving motor. A rotary shaft 121 of this motor is projected upwardly and connected to the bottom part of the moving member 112. To the basal end part of the rotary shaft 121, the basal end part of a rotary arm 122 is fixed.

In the leading end part of the rotary arm 122, an elevation driving device 130 is installed. The elevation driving device 130 is provided with an air cylinder or a cylinder 131 such as a hydraulic cylinder disposed in the vertical direction and a piston rod 132. By the action of the cylinder 131, the piston rod 132 is expanded or contracted, namely moved in the direction of Y (vertical direction) in the bearings of FIG. 1.

The handling device 140 is disposed at the lower end of the piston rod 132. The handling device 140 is provided with a pair (possibly three or more) handling members 141 and 142. In the lower end parts of the handling members, claws 143 and 144 which thrust inwardly are disposed. These handling members 141 and 142 are pivotally supported in a freely openable state in the leading end part of the piston rod 132 and selectively opened and closed by an unshown open-close driving means. As concrete examples of the open-close drive means, a servomotor, a solenoid, and a wire drawing device may be cited.

When the handling device 140 is made to take hold of the cup 4, the handling members 141 and 142 in an opened state are closed and their claws 143 and 144 thrust under the rib 5 of the cup 4. As the handling device 140 ascends, the claws 143 and 144 come into fast contact with the rib 5 and then suspend the cup 4. The drive sources for the moving member 112, the rotary transferring device 120, the elevation driving device 130, and the handling device 140 are severally connected electrically to the control means 30 which will be described specifically hereinbelow. Thus, the control means 30 control their drive.

In the cup conveying mechanism 110 constructed as described above, the handling device 140 can be moved to a desired position within the area of conveyance of the cup 4 in consequence of the motion of the moving member 112 on the conveying rails 111 and the rotational drive of the rotary transferring device 120.

By suitably combining the motion of the moving member 112 with the rotation of the rotary transferring device 120, the handling device 140 is moved to the target position directly above the cup 4 seated on the tray 11 of the container gathering case 10 and the handling members 141 and 142 are opened. Then, the handling members 141 and 142 in an opened state are lowered by the action of the elevation driving device 130. When the handling members 141 and 142 reach the position below the rib 5 of the cup 4 now held in place by the claws 143 and 144, they are closed by the open-close drive means and enabled to chuck the cup 4 to be conveyed.

After the handling members 141 and 142 have taken fast hold of the cup 4, the elevation driving device 130 is again operated to elevate the handling device 140 and make it to suspend the cup 4. After the handling device 140 now suspending the cup 4 has reached a height enough for the cup 4 to avoid touching other devices, the moving member 112 and the rotary transferring device 120 are simultaneously or sequentially driven to move the cup 4 now in a retained state to a point above the cup retaining member 103 positioned on the centrifuge 20 side of the rotary conveying mechanism 101.

Then, the elevation driving device 130 is actuated to lower the cup 4 retained in place by the handling device 140 until the cup 4 fits into the notch 105 of the cup retaining member 103 from above. After completion of the loading of the cup 4 in the notch 105, the handling members 141 and 142 are opened to release the cup 4 and the handling device 140 is further elevated. As a result, the conveyance of the cup 4 is completed.

The handling device 140 is provided with direction detecting means (not shown) which serves the purpose of detecting the direction of the blood bag 2 accommodated in the cup 4. When the cup 4 is loaded in the rotary conveying device 101, it is set infallibly in a posture facing in a prescribed direction. This direction detecting means, for example, may be so constructed as to effect the detection for the direction of the blood bag 2 indirectly on the principle that a mark indicating the direction of the bag 2 is placed in advance on the cup 4 and a sensor is used to detect this mark.

In this invention, the first container conveying device 100 does not need to be limited to the type which conveys the blood bag 2 as held in the cup 4 but may be adapted to convey the blood bag 2 itself directly instead. The mechanism of conveyance in the first container conveying device 100 may be in such a construction that the blood bag 2 will be conveyed as suspended with a hook or in such a construction that the blood bag 2 will be conveyed as mounted on a moving bed or a conveyor, for example.

[Blood component transferring device 150]

In the neighborhood of the rotary conveying mechanism 101 of the first container conveying device 100, two blood component transferring devices 150 adapted to transfer the blood components in the blood bag 2 to the blood component bag through the interconnected tubes 3, 7 are installed. These blood component transferring devices 150 each serve the purpose of expelling the blood components in the blood bag 2 by exerting pressure on the blood bag 2 and, at the same time, inducing aspiration of the blood components. They are each composed of a pair of bag pressing devices 151 and a pair of roller pumps 160 as aspirating means.

Figure 3:
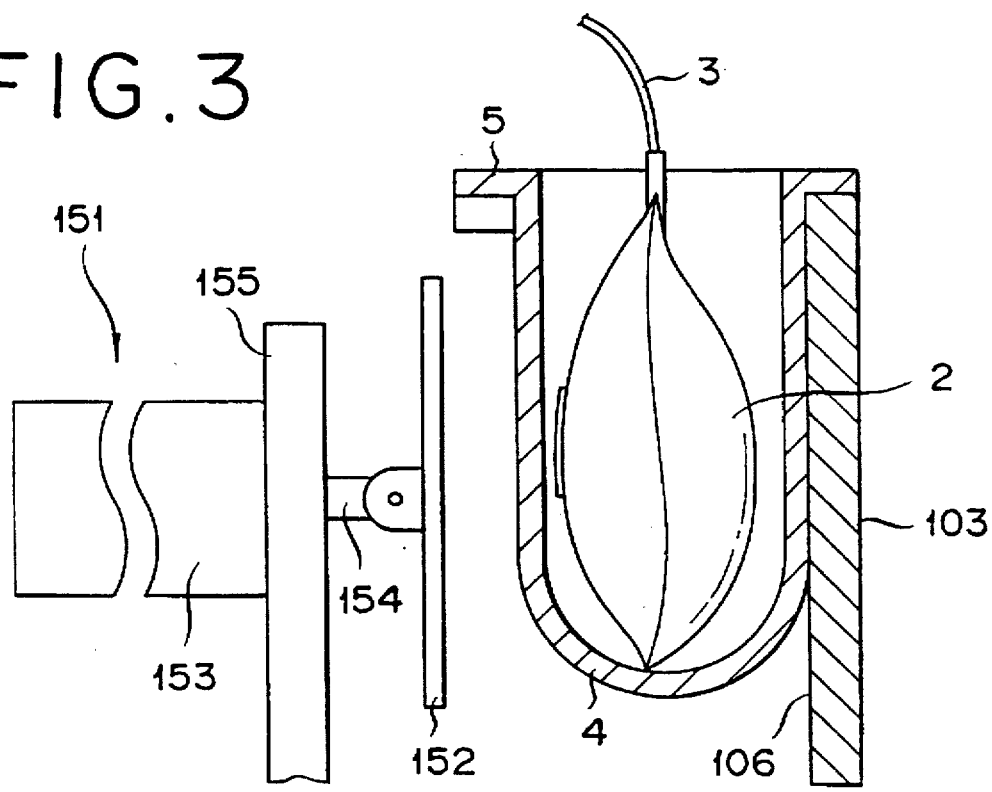
FIGS. 3 and 4 are partially sectioned side views each illustrating a bag compression device.
Figure 4:
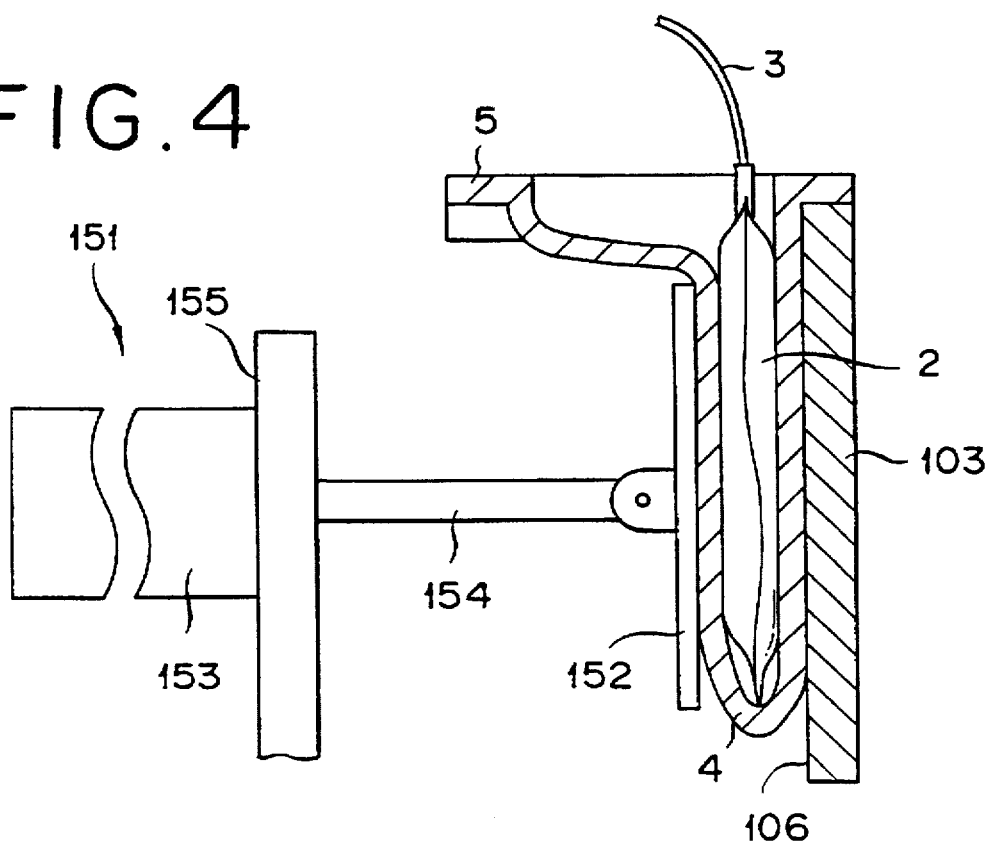

The bag pressing device 151, as illustrated in FIGS. 3 and 4, is composed of a pressing plate 152 disposed opposite a vertical surface 106 of the cup retaining member 103, drive means 153 for moving the pressing plate 152 in the direction of X, and a supporting member 155 adapted to fix the driving means 153 to the main body 15 of the apparatus. As a concrete example of the driving means 153, a hydraulically or pneumatically operating cylinder or a solenoid magnet may be cited.

When the driving means 153 is not in operation as shown in FIG. 3, a rod 154 is a contracted state and the pressing plate 152 assumes a position not in contact with the cup 4 which is retained in place by the cup retaining member 103. When the driving means 153 is actuated as shown in FIG. 4, the rod 154 extends and the pressing plate 152 moves in the direction of approaching the cup retaining member 103 and exerts pressure on the lower half of the cup 4. Since the cup 4 is made of a soft material, it deforms under the pressure and the blood bag 2 held in the cup 4 succumbs to the pressure together with the cup 4.

Incidentally, in the illustrated construction, the pressing plate 152 produces a translation. The behavior of the pressing plate 152 does not need to be limited to this construction. The pressing plate 152 may be otherwise constructed so as to be revolved around the upper end part, the central part, or the lower end part thereof. Alternatively, this pressing plate 152 may be composed of a plurality of mutually independent or mutually connected plate pieces. In this case, the different parts of the blood bag 2 may be severally pressed in an overall pattern fir for the discharge of the blood components by causing the individual plate pieces to produce different motions.

The roller pump 160, as shown in FIG. 38, serves the purpose of moving a liquid in the tube 3 disposed along an arcuately curved surface 163 of a head 162 by causing a plurality of rollers 161 each capable of both rotation and revolution to press and squeeze the tube 3 in cooperation of the curved surface 163. In this case, the head 162 and the rotor possessed of the three rollers 161 are detachably constructed. They assume a mutually separated state while the tube in set in place.

When the tube 3 connected to the blood bag 2 is set in place around the roller pump 160 and then the roller pump 160 is set rotating counterclockwise, negative pressure arises inside the part of the tube 3 intervening between the roller pump 160 and the blood bag 2 and the blood components in the blood bag 2 are aspirated.

The driving means 153 and the roller pump 160 are severally connected electrically to the control means 30 which will be described specifically hereinbelow. Thus, the control means 30 controls the drive of these component parts.

Thus, the blood component transferring device 150 in the present working example is enabled to transfer the blood components quickly without disturbing the boundaries of the separated blood components by simultaneously utilizing the pressure exerted by the bag pressing device 151 on the blood bag 2 and the aspiration produced by the roller pump 160. In this invention, the blood component transferring device 150 may be optionally provided only with either such a mechanism as the aforementioned bag pressing device 151 which presses the blood bag 2 or such aspirating means as the roller pump 160 which aspirates blood components.

The bag pressing device 151 is not always required to be so constructed as to press the bag with the pressing plate 152. It may be otherwise constructed so as to press the blood bag 2 by use of a bag-shaped cuff which is inflated by the introduction of a fluid. The aspirating means does not need to be limited to the roller pump 160 but may be a decompression chamber adapted to accommodate the blood component bag 6 to which the blood components are transferred.

In the blood component transferring device 150, the numbers of bag pressing devices 151 and roller pumps 160 are not always required to be 2 as illustrated in the diagrams. For example, two blood component transferring lines may be concurrently served by one bag pressing device 151 or roller pump 160. In this case, the bag pressing device 151 or the roller pump 160 is installed so as to be moved in the direction of Z.

The blood component transferring device 150, through not shown in the diagram, may further comprise boundary detecting means which serves the purpose of detecting the interfacial boundaries of the separated blood components in the blood bag 2. This boundary detecting means, for example, is provided with a light source and a light receiving element (light sensor) which are opposed to each other across the blood bag 2 and, therefore, is enabled to detect the boundaries based on changes in the amount of light impinging on the light receiving element by virtue of the principle that the blood components show different degrees of transmittance to the light. The information obtained by the boundary detecting means of this operating principle is injected into the control means 30 and utilized for controlling the start/stop of the operations of the bag pressing device 161 or the roller pump 160, for example. The yields of the blood components (ratios of removal of other components) can be improved by carrying out this control.

The blood component transferring device 150 may further comprise flow-path switching means which serves the purpose of pressing the tube and temporarily blocking the inner flow path of the tube 3. In this case, the flow path switching means may be formed exclusively for the purpose just mentioned. It is optional to utilize a pair of claws 212 of the tube pickup device 200 which will be specifically described hereinbelow and a switch mechanism thereof instead of using the flow path switching means.

[First container recovering case 250]

Within the area of conveyance of the first container conveying device 100 described above, the first container recovering case 250 for recovering the blood bag 2 which remains after the transfer of the blood components is disposed opposite the cup retaining member 103 disposed on the front side of the apparatus 1 for the manufacture of blood products as shown in FIG. 1. The first container recovering case 250 is composed of a shooter 251 and chucking means adjustable frame adapted to chuck the cup 4 retained in place by the cup retaining member 103 and guide it to the shooter 251.

The chucking means 252 is composed of a chuck 253 and driving means 254 for moving the chuck 253 in the direction of Z in the bearings of FIG. 1. The chuck 253 is provided with three claws which are made to take hold of two cups 4 simultaneously when the two outer claws are caused to approach the central claw by use of such drive source as a solenoid magnet (not shown).

The drive sources for the driving means 254 and the chuck 253 are severally connected electrically to the control means 30 which will be specifically described hereinbelow. This control means 30, therefore, controls the drive of these component parts.

In the chucking means 252 constructed as described above, the cup 4 retained in place by the cup retaining member 103 positioned on the front side of the apparatus 1 for the manufacture of blood products is chucked by the chuck 253. The driving means 254 moves the chuck 253 in the direction of the front side of the apparatus 1 to effect removal of the cup 4 from the cup retaining member 103, brings the chuck 253 to a stop above the upper opening of the shooter 251, and causes the chuck 253 to release the blood bag 2 and allow the blood bag 2 to fall together with the cup 4 into the shooter 251. The blood bags 2 recovered and gathered in the shooter 251 are then extracted through an outlet 255 which is formed in the front wall of the apparatus 1 for the manufacture of blood products.

In the place of the chucking means 252 provided for the first container recovering case 250, the cup conveying mechanism 110 mentioned above may be utilized for extracting the cup 4 retained in place by the cup retaining member 103 and causing the cup 4 to fall into the shooter 251.

[Tube pickup device 200]

The tube pickup device 200 is a tool for conveying the leading end part of the tube 3 retained in place in the upper end part of the cup 4 to a gap between two rollers 312 of the tube conveying device 300 and facilitating connection of the tube 3 to a tube 7. The tube pickup device 200, as illustrated in FIGS. 5 to 9, is provided with tube conveying means 210, tube fixing means 220, and tube guiding means 230.

The tube conveying means 210 comprises a moving member 211, a pair of claws 212 protruding downwardly from the moving member 211, and a moving mechanism (not shown) for the moving member 211. The distance between the two claws 212 can be varied by an unshown switching mechanism. The two claws 212 are enabled to chuck the tube 3 therebetween by the adjustment of this distance. The switching mechanism for the claws 212 may be the same as what is formed by chucks 353 and 354 of the tube loading device 350 which will be specifically described hereinbelow.

The moving member 211 can be moved in the range from the neighborhood of the rib 5 of the cup 4 to roller 312 in the tube conveying device 300 which will be described specifically hereinbelow. The moving mechanism for the moving member 211 is not specifically illustrated in the drawing. The moving member 211 may be so constructed as to be moved three-dimensionally with a shaking arm composed of a plurality of links or so constructed as to be moved two-dimensionally in the directions of X and Y in the diagram by the combination of vertical rails and horizontal rails, for example.

Figure 6:
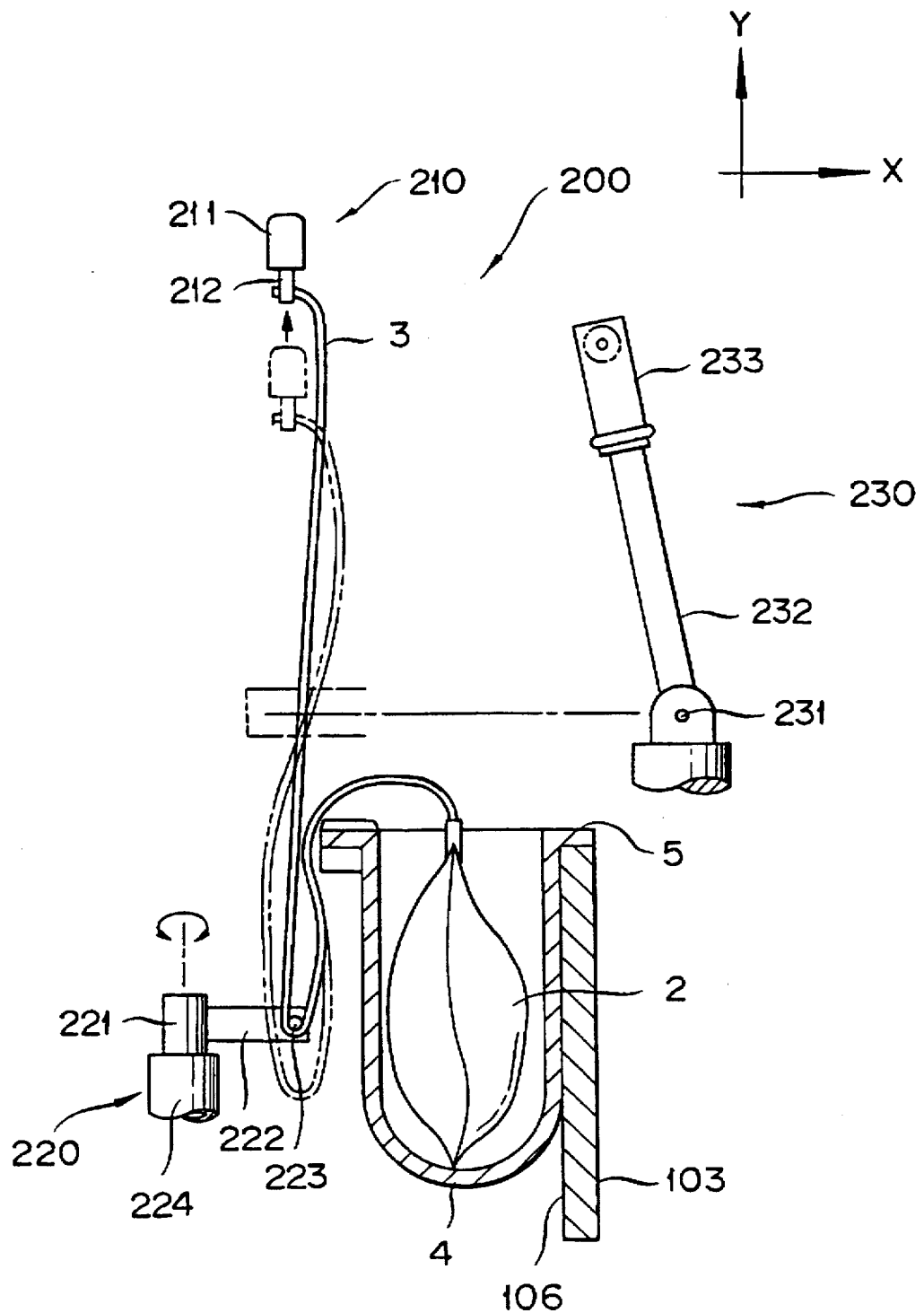

The tube fixing means 220 comprises a rotary shaft 221, an arm 222 projecting from the rotary shaft 221 in the radial direction of the rotary shaft 221, a pin 223 projecting from the leading end of the arm 222 in a direction perpendicular to the arm 222, and a drive source 224 for rotating the rotary shaft 221. Owing to the drive of the drive source 244, the rotary shaft 221 rotates and the arm 222 consequently rotates the pin 223 changes its position. The pin 223 serves the purpose of colliding against the tube 3 having down from the edge of the cup 4 and imparting tension to the tube 3 which is pulled up by the tube conveying means 210 as shown in FIG. 6.

Figure 9:
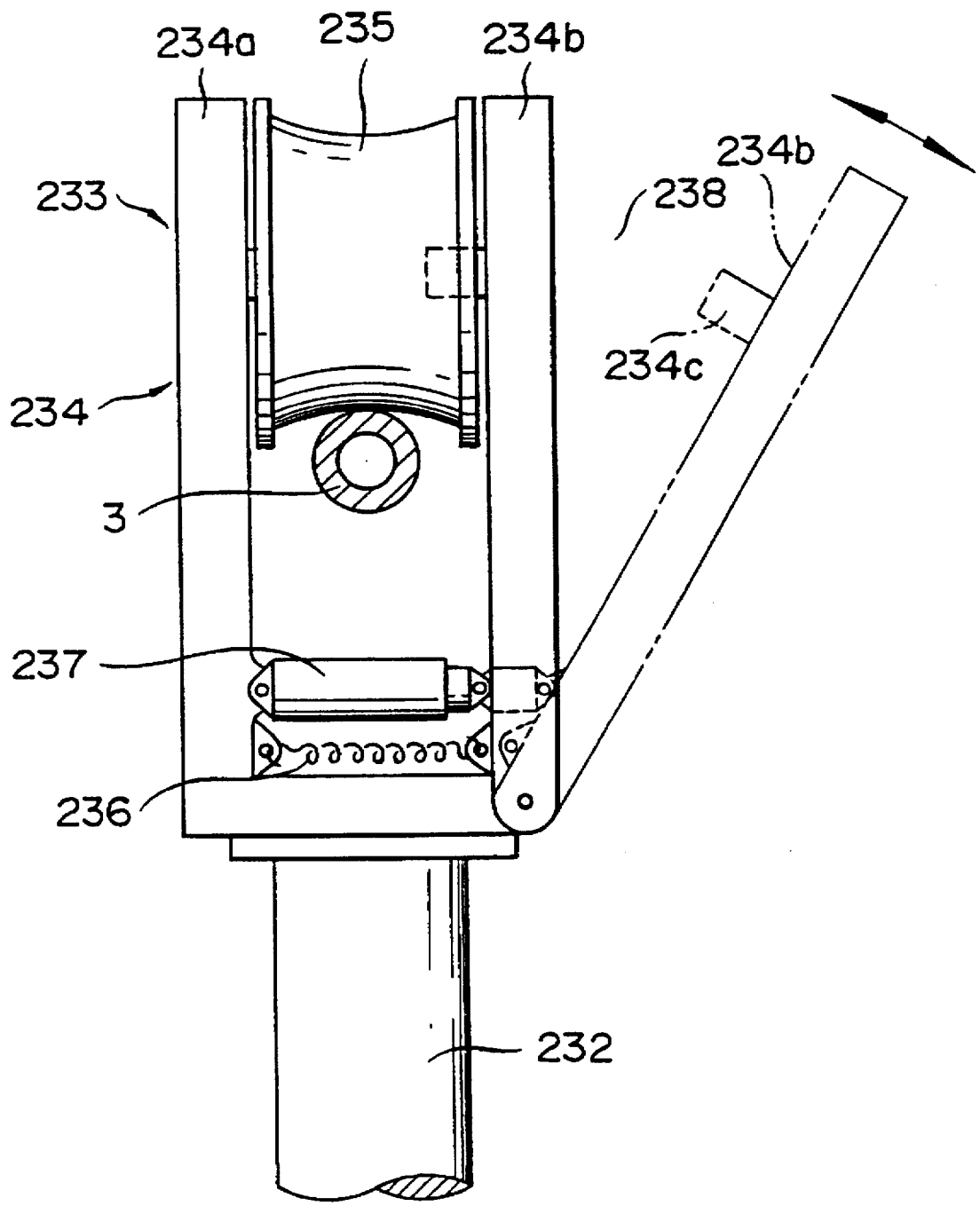
FIG. 9 is a plan view illustrating a tube guiding part on a magnified scale.

The tube guiding means 230 assumes its position near the rotary conveying mechanism 101 and comprises an arm 232 allowed to rotate round a fulcrum 231, a tube guiding part 233 provided at the leading end of the arm 232, and a drive source (not shown) adapted to rotate the arm 232 in the range of a prescribed angle. The tube guiding part 233, as illustrated in FIG. 9, comprises a frame 234 formed in the shape of three sides of a square, a guide roller 235 pivotally supported on the open end side (upper side in the bearings of FIG. 9) in the frame 234, an urging member 236, and opening means 237. The frame 234 is composed of an L-shaped fixed frame 234a and an adjustable frame 234b rotatably connected to the basal end side (lower side in the diagram) of the fixed frame 234a.

The frame 234 of the shape of three sides of a square is so constructed that the interval between the opposed sides of the square on the open end side of the frame 234 is widened or narrowed by the oscillation of the adjustable frame 234b. The guide roller 235 is rotatably disposed between the fixed frame 234a and the adjustable frame 234b. This guide roller 235 is supported on the fixed frame 234a side. From the inside wall of the adjustable frame 234b, a pin 234c which is inserted in a hole at the center of the guide roller 235 when the adjustable frame 234b is closed (as indicated by a solid line in FIG. 9) is raised.

Between the fixed frame 234a and the adjustable frame 234b which are constructed as described above, switching means is provided on their basal end sides. The switching means is composed of the urging member 236 and the switching member 237. The urging member 236 and the switching member 237 are set in place independently between the fixed frame 234a and the adjustable frame 234b. The urging member 236 is formed of a spring as shown in the diagram and adapted to pull the adjustable frame 234b toward the fixed frame 234a, namely to bring the adjustable frame 234b to its closing position.

The switching member 237 is formed of a solenoid which comprises a coil capable of generating a magnetic field and a plunger capable of reciprocating in the axial direction inside the coil. When the solenoid is powered, the plunger extends in spite of the urging force of the urging member 236 and causes the adjustable frame 234b to open (indicated by a two-dot chain line in FIG. 9). When the solenoid is de-powered, the urging member 236 exerts an action to close the adjustable frame 234b (indicated by a solid line in FIG. 9).

The guide roller 235 is supported on the adjustable frame 234b side and is so constructed as to have a pin raised from the inside wall of the fixed frame 234b similarly to the pin 234c mentioned above.

The drive sources for the moving mechanism of the moving member 211 and the switching mechanism of the claws 212, the drive source 224 for the tube fixing means 220, the drive source for rotating the arm 232, and the switching member 237 are severally connected electrically to the control means 30 which will be specifically described hereinbelow. The control means 30 controls the drive of these component parts.

Now, the operation of the tube pickup device 200 which is constructed as described above will be explained below. The leading end part of the tube 3 retained by the rib 5 of the cup 4 is chucked by the two claws 212 of the tube conveying means 210 and pulled upwardly by elevating the moving member 211 as shown in FIG. 5. As a result, the tube 3 held inside the cup 4 is wholly pulled out of the cup 4 (as indicated by a two-dot chain line in FIG. 5).

When the moving member 211 is subsequently lowered, the tube 3 which has been pulled out forms a sag beneath the rib 5. At this time, the rotary shaft 221 of the tube fixing means 220 is rotated to induce insertion of the pin 223 in a loop produced by the sag of the tube 3 mentioned above. When the moving member 211 is then elevated again, the tube 3 gets caught on the pin 223 and stretches taut between the moving member 211 and the pin 223 (as indicated by a solid line in FIG. 6). This tension of the tube 3 results in fixing the position of the tube 3.

Then, the arm 232 of the tube guiding device 200 which has remained in an erect state is laid down and the tube guiding part 233 is moved to the position at which the tube 3 is stretched taut (as indicated by a two-dot chain line in FIG. 6). At this time, the tube guiding part 233 shakes the adjustable frame 234b and opens the frame 234 owing to the action of the switching member 237 as indicated by a two-dot chain line in FIG. 6. Then, the tube 3 is drawn into the tube guiding part 233 through the opening part 238 now in an opened state and the adjustable frame 234b is returned to the home position to set the frame 234 in a closed state. As a result, the tube 3 is passed through an empty space which is enclosed with the frame 234 of the shape of three sides of a square and the guide roller 235.

Figure 7:
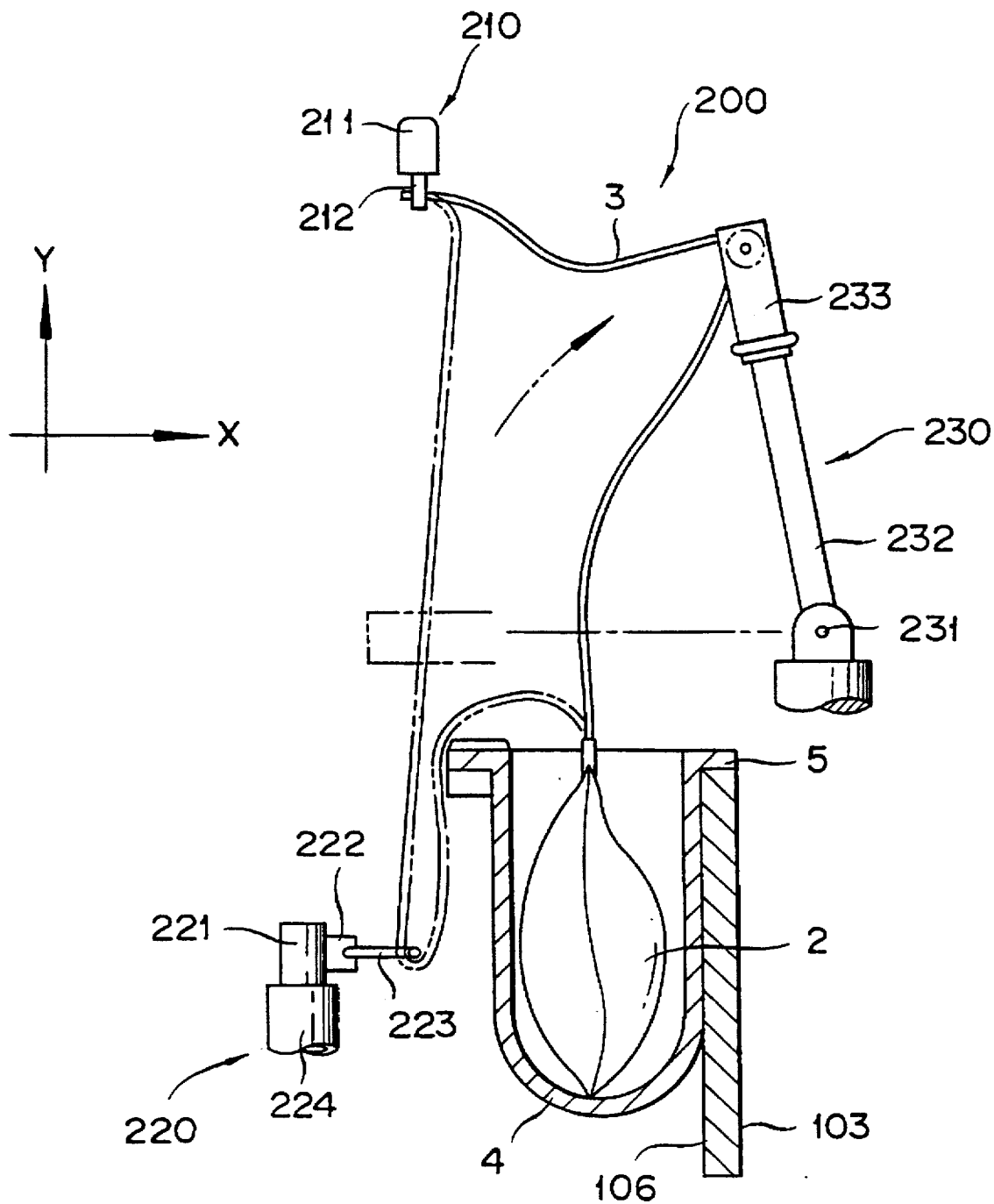

Subsequently, the rotary shaft 221 of the tube fixing means 220 is rotated in the direction opposite to the aforementioned direction to release the pin 223 from inside the loop of the tube 3. When the arm 232 is given an erected state as shown in FIG. 7, the downward sag of the tube 3 ceases to exist and the tube 3 assumes a stretched state between the moving member 211 and the tube guiding part 233.

Figure 8:
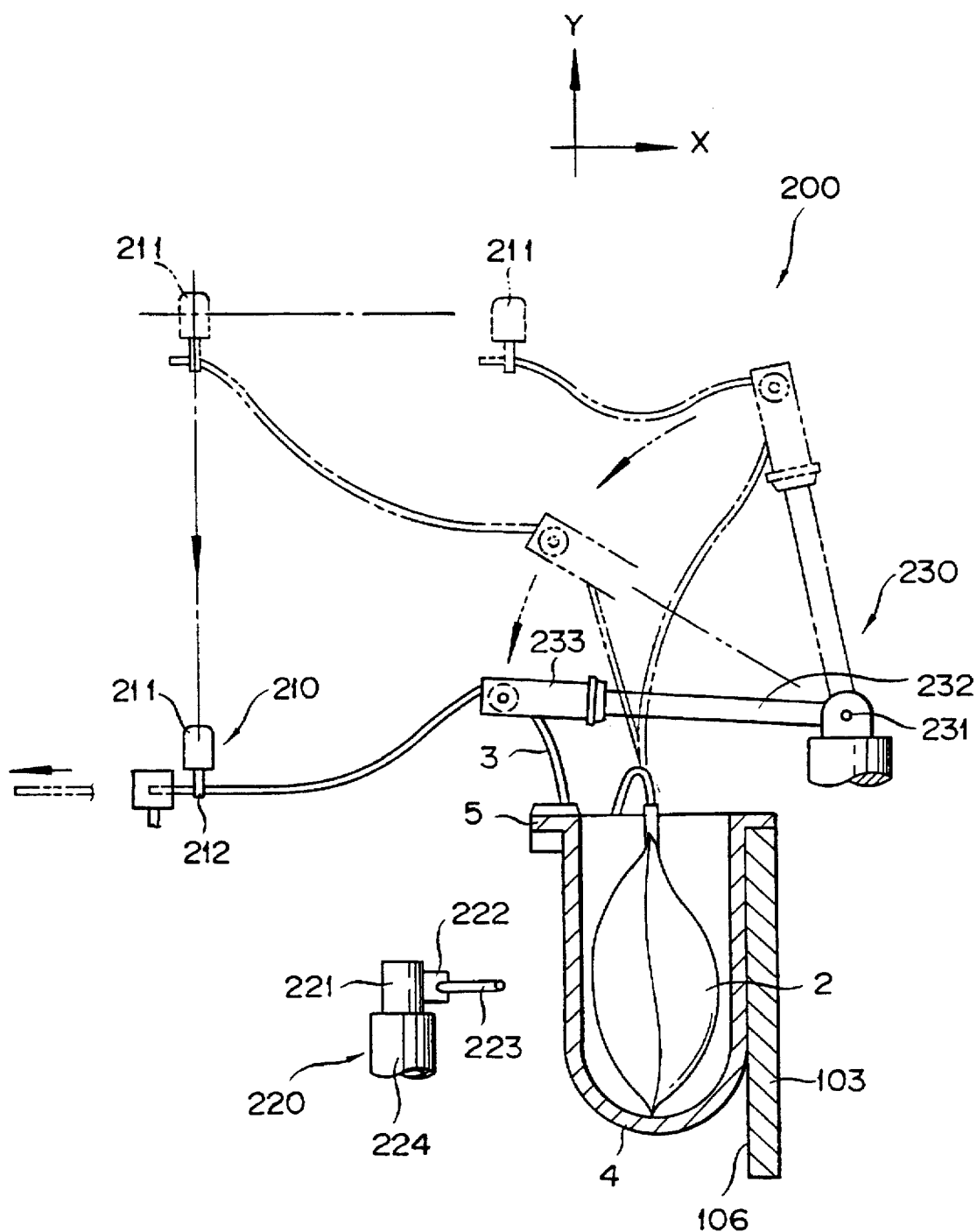

Now, the moving member 211 is moved along a locus indicated by a two-dot chain line in FIG. 8 to advance the leading end of the tube 3 chucked by the two claws 212 to a gap between the pair of rollers 312. In this case, the arm 232 is the erected state is laid down gradually so that the stretched state of the tube existing between the moving member 211 and the tube guiding part 223 will be kept intact.

By keeping the stretched state of the tube 3 between the moving member 211 and the tube guiding part 233 intact during the conveyance of the tube 3, the tube 3 can be prevented from sagging down and getting caught on any of other devices located between the route of conveyance and, therefore, can be smoothly conveyed.

When the two claws 212 are relaxed to let go the tube 3 and the roller 312 is set rotating after the leading end of the tube 3 has been inserted between the rollers 312, the tube 3 is conveyed along the prescribed path of conveyance in the tube conveying device 300 which will be specifically described hereinbelow.

After the tube 3 has been conveyed to the target position, the component parts of the tube pickup device 200 are returned to their home positions and kept there to await the conveyance of the next tube 3.

The tube pickup device 200 constructed and operated as described above may be used either concurrently for two transfer lines for blood components or exclusively for each transfer line for blood components.

[Tube conveying device 300]

Figure 10:
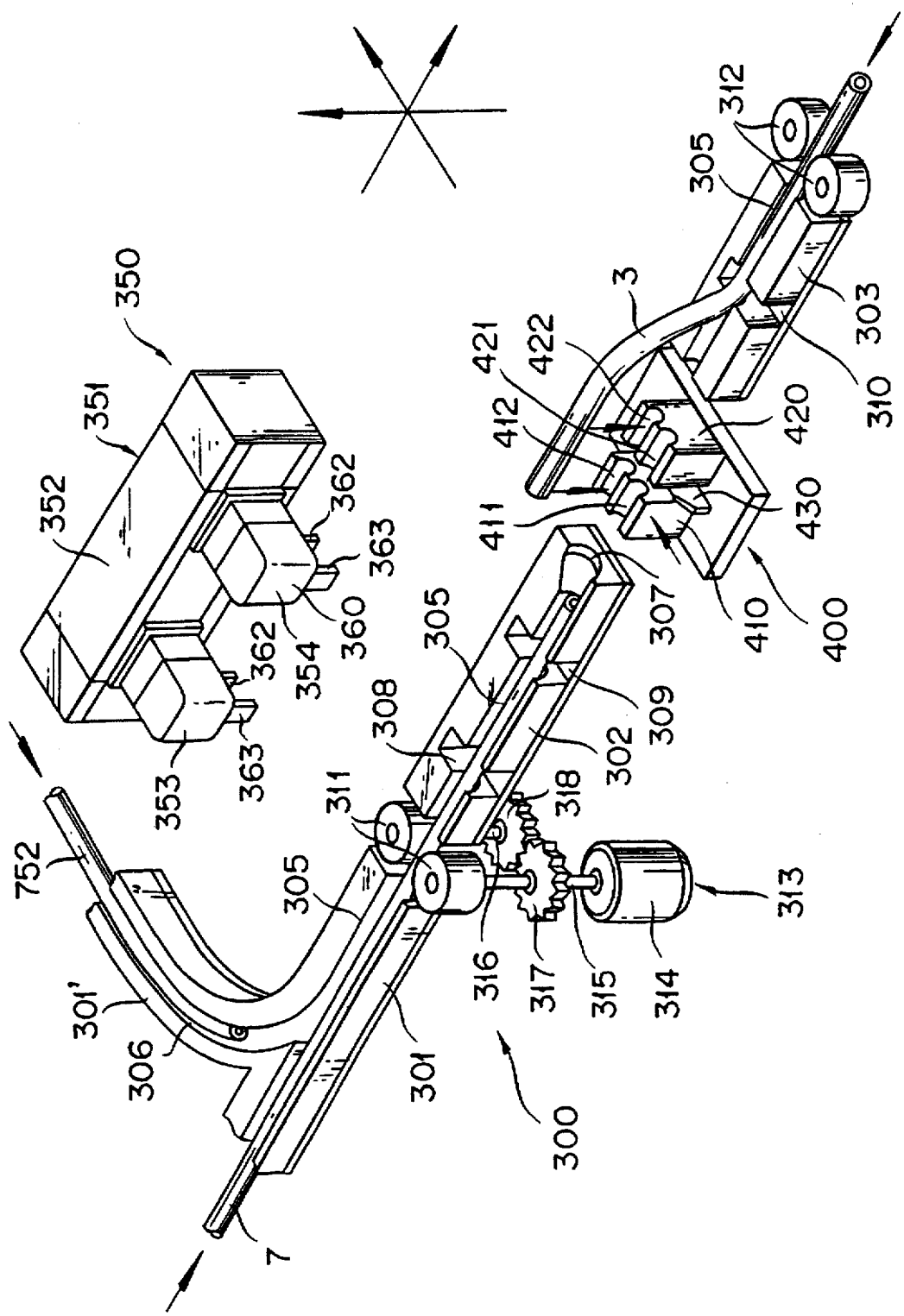
FIG. 10 is a perspective view illustrating a tube conveying device and a tube loading device.

The tube conveying device 300, as illustrated in FIG. 10, is a tool for moving the tube of flexible material in the longitudinal direction thereof. It is composed of conveying rails 301, 302, and 303 defining a path for the conveyance of the tube, at least one pair of rollers 311 and 312 disposed between the adjacent conveying rails or in the end parts of the conveying rails, and driving means 313 for rotating the rollers.

Specifically, in the construction shown in FIG. 10, the conveying rails 301, 302, and 303 are sequentially disposed in the order mentioned from the upstream side of the direction of conveyance of the tube 7 (direction of +X) (hereinafter referred to simply as "upstream side") to the downstream side of the direction of conveyance of the tube 7 (hereinafter referred to simply as "downward side").

In these conveying rails 301 to 303, a groove 305 having a U-shaped cross section, for example, is formed as a route for passing the tube. A branched rail 301' is formed in the conveying rail 301. In the branched rail 301', a groove 306 resembling the groove 305 and meeting this groove 305 is formed as a path for passing a third tube 752 connected to a chemical solution container 751 of the chemical solution feeding device 750 which will be specifically described hereinbelow. These grooves 305 and 306 have a width slightly larger than the outer diameter which the tube to be conveyed assumes in its no-load state.

In the tube connecting device 400 which will be specifically described hereinbelow, an end part 307 on the downstream side of the groove 305 formed in the conveying rail 302 is flared to counter a possible deviation of the tube in the direction of Z due to the motion of a holder 410 during the union of tube ends. In the midway of the conveying rail 302, a recess 308 for admitting chucking members 362 and 363 of the chuck 353 in the tube loading device 350 which will be specifically described hereinbelow and a recess 309 for admitting the chucking members 362 and 363 of the chuck 354 are formed.

Further, in the midway of the conveying rail 303, a recess 310 for admitting the chucking members 362 and 363 of the chuck 354 are formed.

The paired rollers 311 are opposed to each other across the path of conveyance of the tube between the downstream side end part of the conveying rail 301 and the upstream side end part of the conveying rail 302. During the conveyance of the tube, the tube is kept chucked by the two rollers 311 which are kept rotating in the meantime.

The peripheral surfaces of the rollers 311 are desired to be formed of a rubber material such as, for example, natural rubber, isoprene rubber, butadiene rubber, silicone rubber, nitrile rubber, propylene rubber, or urethane rubber or an elastic material such as, for example, polyurethane or a thermoplastic elastomer (of the styrene type, olefin type, urethane type, ester type, etc.). The rollers 5 may contain convexo-concave ribs extending in the direction of the axis of rotation thereof on their surfaces. Owing to the arrangement, the rollers are prevented from slipping on the tube and enabled drive to draw and convey the tube infallibly.

The rollers 311 so constructed are rotated by the driving means 313. This driving means 313 is composed of a motor 314 as a drive source, a rotary shaft 315 of the motor, a driven shaft 316, a toothed wheel 317 fixed in the midway of the rotary shaft 315, and a toothed wheel 318 fixed in the lower end part in the bearings of illustration of the driven shaft 316 and meshed with the toothed wheel 317. The rollers 311 are severally fixed in the upper end parts in the bearings of illustration of the rotary shaft 315 and the driven shaft 316.

When the motor 341 is set rotating, one of the rollers 311 is rotated in a prescribed direction through the rotary shaft 315 and, at the same time, the other roller 311 is rotated in the direction opposite to the direction mentioned above owing to the transfer of the force of rotation of the first roller 311 to the toothed wheels 317 and 318 and to the driven shaft 316. When the two rollers have an equal external diameter, the toothed wheels 317 and 318 are desired to have an equal number of teeth so that the two rollers 311 will rotate at an equal speed.

The paired rollers 311 may be so constructed that the distance separating them will be varied as occasion demands. One of the paired rollers 311 may be a freely rotating roller (idle roller).

In the downstream side end part of the conveying rail 303, the roller 312 resembling the aforementioned roller 311 and the driving means 313 (omitted from illustration) similar to the aforementioned driving means are installed.

Further, as illustrated in FIG. 1, a pair of rollers 320 resembling the aforementioned rollers 311 are disposed in the upstream side end part of the conveying rail 301 and a pair of rollers 321 resembling the rollers 311 are disposed in the upstream side end part of the branched rail 301'. These rollers 320 and 321 are likewise provided with the driving means 313 (not shown). The pair rollers 320 may be so constructed that the distance separating them will be varied as occasion demands.

The conveyance of the tube of this nature to the target position may be accomplished by a method of controlling the driving time (drive timing) of the motor 314 of the driving means 313 by use of the control means 30 with a built-in timer or a method of controlling the start/stop status of the rollers 311 and 312 based on the result of detection by use of an unshown sensor (tube position detecting means) such as, for example, a photosensor, magnetic sensor, or tough switch which is capable of detecting the position of the leading end of the tube and which is installed on the path for conveyance of the tube.

The tube connecting device 400 which will be specifically described hereinbelow is installed between the downstream side end part of the conveying rail 302 and the upstream side end part of the conveying rail 303.

[Tube loading device 350]

The tube leading device 350 is a tool for loading the tube conveyed by the tube conveying device 300 into the tube connecting device 400. The tube loading device 350, as illustrated in FIG. 10, is provided with a head 351 which is composed of a blocklike base 352, two chucks 353 and 354 disposed on the base 352 and adapted to chuck the tube, and driving means 370 (as illustrated in FIG. 11) for moving the chuck 354.

The chucks 353 and 354 are disposed on the front side of the base 352 as separated by a prescribed distance. The chuck 353 is stationarily disposed relative to the base 352 and the chuck 354 is disposed movably in the direction of X in FIG. 10 relative to the base 352. The motion of the chuck 354 varies the distance which intervenes between the two chucks 353 and 354.

Figure 11:
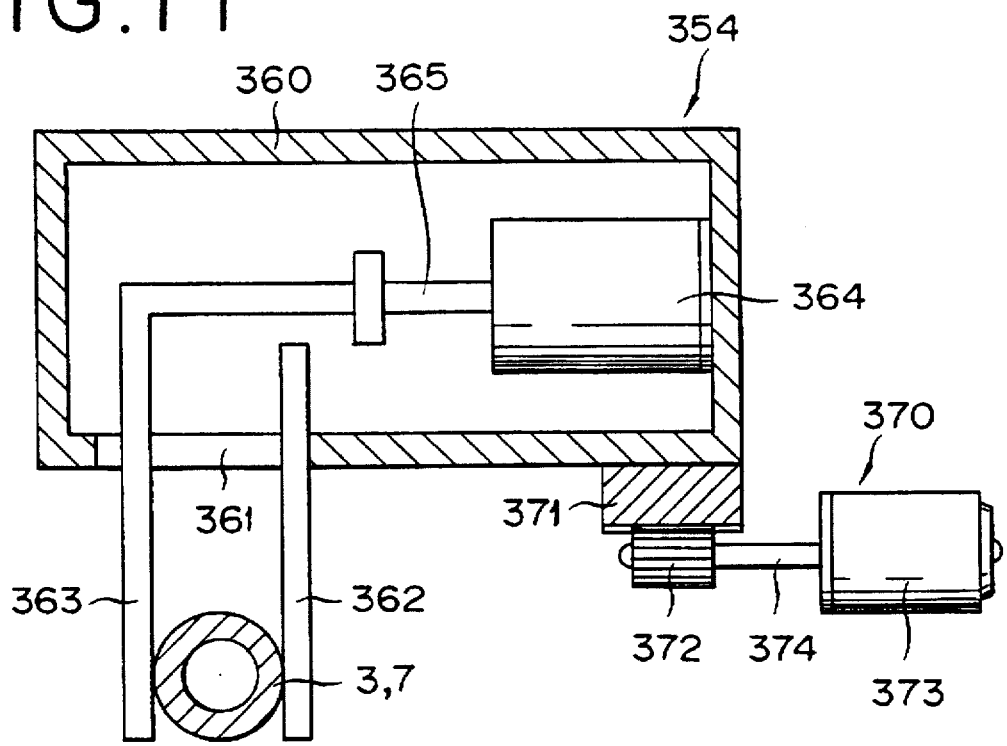
FIGS. 11 and 12 are partially sectioned side views each illustrating a tube loading device.
Figure 12:
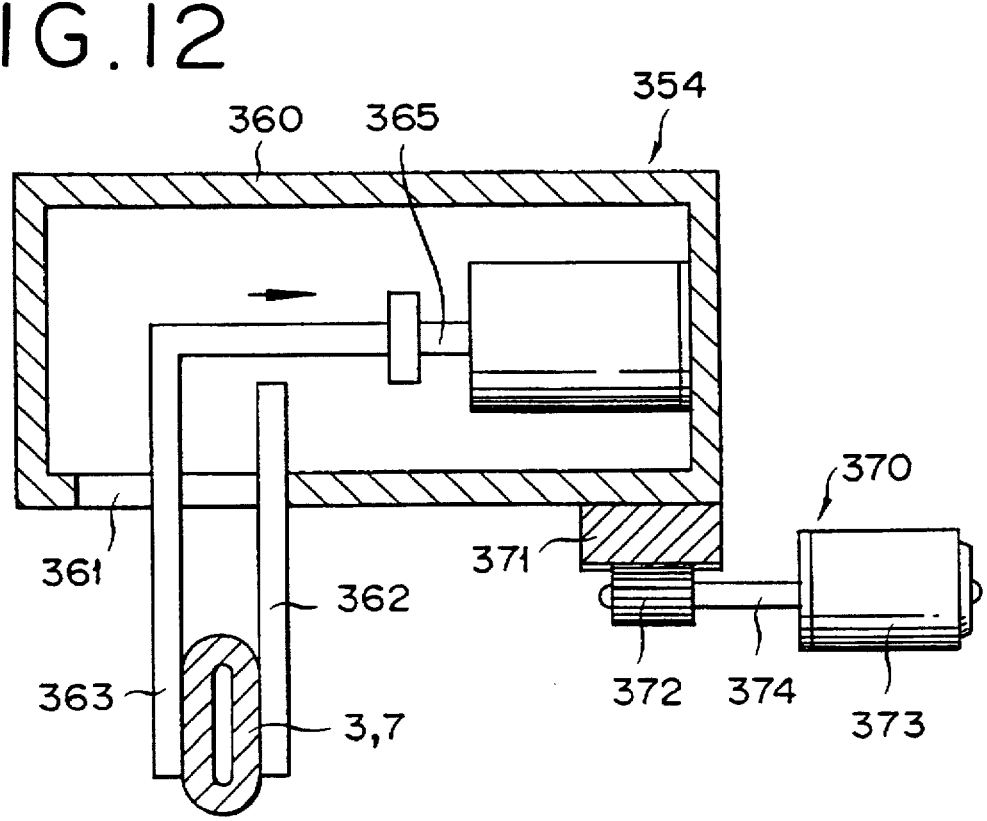

FIG. 11 and FIG. 12 are each a partially sectioned side view illustrating the chuck 354. The chuck 354, as shown in these diagrams, comprises a casing 360 containing an opening 361, a pair of platelike chucking members 362 and 363 adapted to chuck the tube, and a drive mechanism for the chucking member 363. The chucking members 362 and 363 protrude from the casing 360 through the opening 361.

The chucking member 362 is stationarily disposed relative to the casing 360 and the chucking member 363 is disposed movably in the direction of Z. The basal end (upper end in the bearings of FIG. 11) of the chucking member 363 is bent in the shape of the letter L and connected to the leading end of a plunger 365 of a solenoid 364 disposed stationarily inside the casing 360.

When the solenoid 364 is not in action as illustrated in FIG. 11, the plunger 365 is left in a stretched state and the two chucking members 362 and 363 are separated with an interval enough to admit the tubes 3, 7.

When the solenoid 364 is in action as illustrated in FIG. 12, the plunger 365 withdraws, the chucking member 363 moves toward the chucking member 362 consequently, and the tube 3 and a similar part are chucked between the two chucking members 362 and 363.

The pressure with which the chucking members 362 and 363 chuck such parts as the tube 3 are desired to be such that when the tube 3 is chucked and elongated at the aformentioned ratio of stretching, the chucking members 362 and 363 will neither slip on the tube nor inflict injuries such as rupture and tear on the tube or impart irrecoverable deformation thereto.

A driving means 370 for moving the chuck 354 is composed of a rack gear 371 stationarily disposed in the lower part of the casing 360, a motor 373, and a pinion gear 372 fixed to the leading end part of the rotary shaft 374 of the motor 373 and meshed with the rack gear 371 mentioned above. When the motor 373 is set rotating, the pinion gear 372 rotates in a prescribed direction and, in consequence of this rotation, the rack gear 371 moves in the longitudinal direction thereof, namely in a direction perpendicular to the plane of paper of FIG. 11 (the direction of X indicated in FIG. 10). As a result, the chuck 354 moves in the same direction.

The motor 373 can be operated reversibly and consequently the chuck 354 can be reciprocated in a direction perpendicular to the plane of paper of FIG. 11 (the direction of X indicated in FIG. 10).

The construction of the chuck 353 is identical with that of the chuck 354 described above excepting it lacks the driving means 370.

The constructions of the chucks 353 and 354 are not always required to be limited to those described above. For example, the chucking member 363 may be actuated by use of such a driving source as an air cylinder or a hydraulic cylinder instead of the solenoid mentioned above. The same remarks hold good for the driving source and the driving mechanism which serve the driving means 370 for moving the chuck 354.

In the illustrated construction, the chuck 354 alone is moved. The construction, when necessary, may be modified so as to attain the variation of the distance between the two chucks by moving both the chucks 353 and 354.

Figure 13:
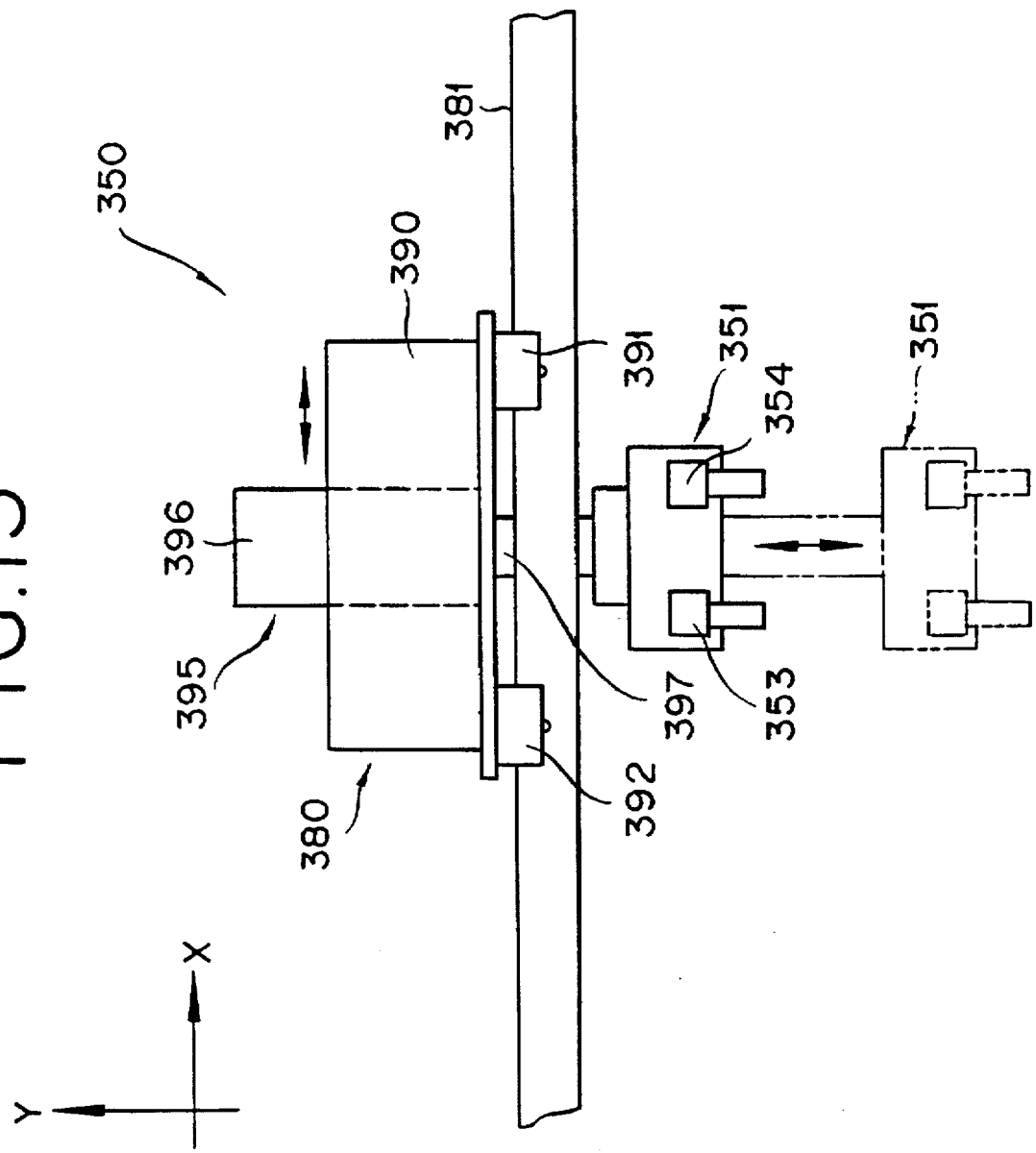
FIG. 13 is a front view illustrating the tube loading device.

The head 351 which is composed of the base 352, the chucks 353 and 354, and the driving means 370 as described above is disposed so as to be moved in two-dimensional directions, namely in the direction X indicated in FIG. 1 and the direction Y perpendicularly intersecting the direction X, by means of a moving mechanism 380 constructed as shown in FIG. 13.

The moving mechanism 380 comprises a conveying rail 381, a moving member 390, and an elevating device 395. The conveying rail 381 is disposed parallel to the longitudinal direction of the tube in the line of transfer of blood components, namely in the direction of X.

The moving member 390 is mounted on the conveying rail 381 and reciprocated along the conveying rail 381. The moving member 390 is provided with two pairs of rollers 391 and 392 for chucking the conveying rail 381 and a motor (not shown) for rotating these rollers 391 and 392. This motor can be reversibly rotated. When the rollers 391 and 392 are rotated by the action of the motor, the moving member 390 is moved on the conveying rail 381 within a prescribed range.

The moving member 390 is provided with the elevating device 395. This elevating device 395 is provided with a cylinder 396 such as an air cylinder or a hydraulic cylinder disposed in the vertical direction and a piston rod 397 which can be moved by the action of the cylinder 396. To the lower end of the piston rod 397, the head 351 is fixed.

By the moving mechanism 380 constructed as described above, the head 351 is moved in the direction of X in FIG. 1 in consequence of the motion of the moving member 390 and then moved in the direction of Y (the vertical direction) indicated in FIG. 1 in consequence of the movement of the piston rod 397.

The solenoid 364 serving the two chucks 353 and 354, the motor 373 serving the driving means 370, and the driving sources serving the moving member 390 and the elevating device 395 are severally connected electrically to the control means 30 which will be specifically described hereinbelow. This control means controls the operations of the component parts so connected thereto.

In the working example described thus far, the moving mechanism 380 mentioned above is only required to be movable two-dimensionally in the directions of X and Y because the tube connecting device 400 is so constructed as to be moved in the direction of Z to load the two tubes subjected to connection in desired grooves of holders 410 and 420. This arrangement is not critical for this invention. Optionally, the moving mechanism 380 may be so constructed as to be movable three-dimensionally in the directions of X, Y, and Z. In this case, moving means for moving in the direction of Z may be provided at the leading end of the piston rod 397 and the head 351 may be disposed on the underside of the moving means.

The tube loading device 350 constructed and operated as described above may be utilized concurrently for two lines of transfer of blood components or may be disposed for use by each line of transfer of blood components.

Figure 14:
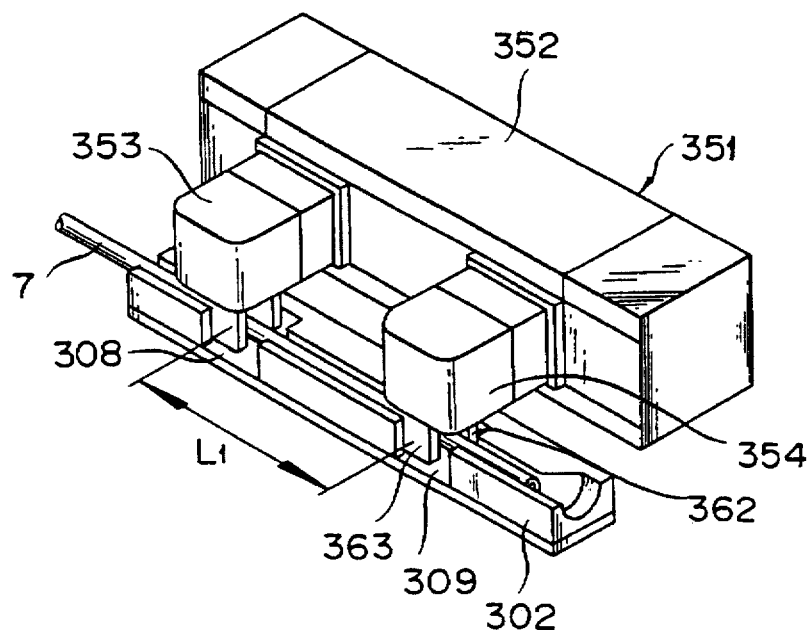
FIGS. 14 to 16 are perspective view each illustrating a step of loading a tube by use of a tube loading device.
Figure 15:
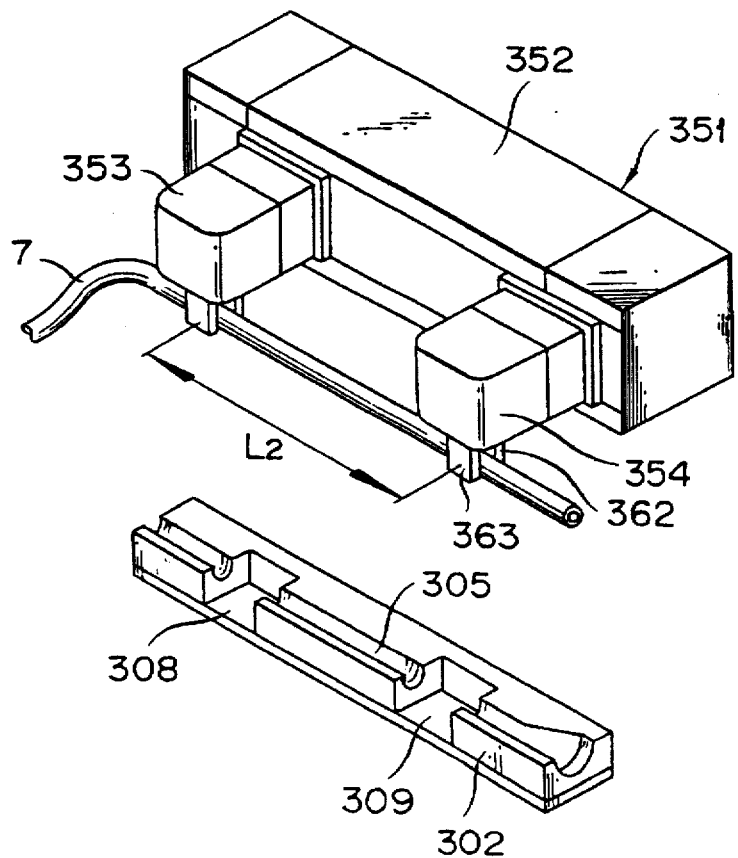
Figure 16:
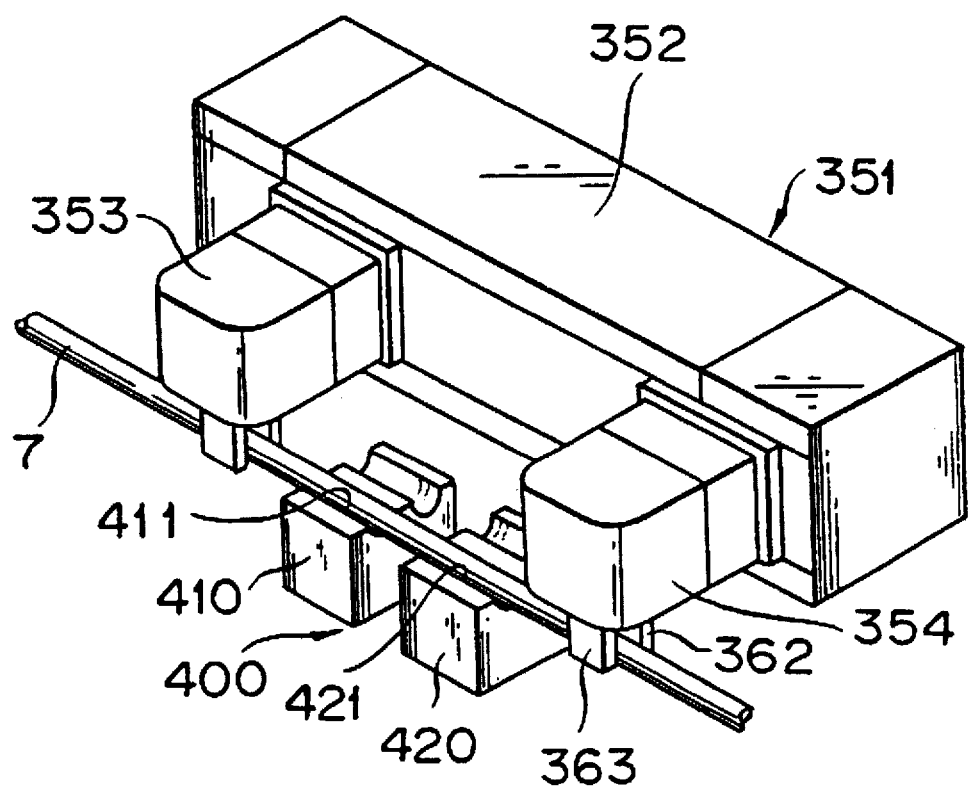

Now, the method for loading the tube by use of the tube loading device 350 will be described below. FIGS. 14, 15, and 16 are perspective views severally illustrating component steps of a process for loading the tube by use of the tube loading device 350.

The tube conveying device 300 is operated to convey the tube 7 in the direction of X from the upstream to the downstream side until the leading end of the tube 7 passes the recess 309 and, at the same time, convey the tube 3 in the direction of X from the downstream to the upstream side until the leading end of the tube 3 protrudes to a prescribed length from the upstream side end face of the conveying rail 303.

The moving member 390 and the elevating device 395 of the moving mechanism 380 are operated to position the head 351 above the conveying rail 303 and bring the two chucks 353 and 354 into a closely approximating state (the distance separating the chucks=$L_1$) and, at the same time, and move the chucking members 362 and 363 of the two chucks 353 and 354 away from each other enough to admit the tube 7.

Then, the elevating device 395 is operated to lower the head 351 as shown in FIG. 14 and insert the chucking members 362 and 363 of the two chucks 353 and 354 into the corresponding recesses 308 and 309. As a result, the tube 7 is inserted between the chucking members 362 and 363 of the two chucks 353 and 354.

By the operation of the solenoids 364 built in the two chucks 353 and 354, the two chucking members 362 and 363 are actuated to chuck the tube 7 at two different points. By the operation of the elevating device 395, the head 351 is elevated to its home position and the tube 7 is consequently lifted.

Now, while the two chucks 353 and 354 are still in the state of keeping the tube 7 chucked, the driving means 370 is operated to move the chuck 354 away from the chuck 353 to a prescribed distance (the distance separating the chucks 353 and 354=$L_2$). As a result, the tube intervening between the two chucks 353 and 354 is elongated with a decrease of the external diameter thereof.

The relation of $L_1$ and $L_2$ is desired to be such that the ratio $L_2/L_1$ will fall in the approximate range of 102 to 130%, preferably 105 to 115%. Thus, the ratio of decrease of the external diameter of the tube 7 (the external diameter in the elongated state/the original external diameter) falls in the approximation range of 75 to 98%, preferably 85 to 95%. The tube, therefore, can be easily and infallibly loaded in the tube connecting device 400.

Now, the tube 7 is kept in the elongated state and the moving member 390 and the elevating device 395 are operated to move the head 351 in the direction of X and the direction of Y (in the downward direction in the bearings of the diagram) and induce the insertion of the tube 7 held between the two chucks 353 and 354 into grooves 411 and 421 of the holders 410 and 420 as shown in FIG. 16. At this time, the tube 7 held between the two chucks 353 and 354 is easily inserted into the grooves 411 and 421 without encountering any resistance and is not allowed to float up because the tube 7 has the external diameter thereof decreased to the degree mentioned above.

Then, the chucking members 362 and 363 of the two chucks 353 and 354 are relaxed to let go the tube 7. As a result, the elongated tube 7 is allowed to resume its original state by virtue of its own elasticity. Owing to this resumption of the original state, the tube 7 inside the grooves 411 and 421 grows in external diameter, with the result that the tube 7 will be fixed infallibly and tightly in the grooves 411 and 421.

The head 351 is moved in the direction of Y (the upward direction in the diagram) and in the direction of X and positioned above the conveying rail 303 and, at the same time, the driving means 370 is actuated in the direction opposite to the direction mentioned above to move the chuck 354 toward the chuck 353 to a prescribed distance and put the two chucks 354 and 353 in the former state (the distance separating the chucks 353 and 354=$L_1$).

Thereafter, the procedure described thus far is repeated so that the tube 3 held theretofore in the groove 305 of the conveying rail 303 will be loaded in the grooves 412 and 422 of the holders 410 and 420 (FIG. 10). Preparatorily to the insertion of the tube 3 into the grooves 412 and 422, the tube connecting device 400 is moved in the direction of Z to a distance equivalent to the center-to-center distance of the grooves 411 and 412 so that the grooves 412 and 422 will be positioned directly below the tube 3 which is kept chucked by the two chucks 353 and 354.

When a tube 752 which will be specifically described hereinbelow and the tube 3 are to be loaded in the tube connecting device 400 in order to be interconnected therein, the same method of loading as described above is adopted.

[Tube connecting device 400]

Figure 17:
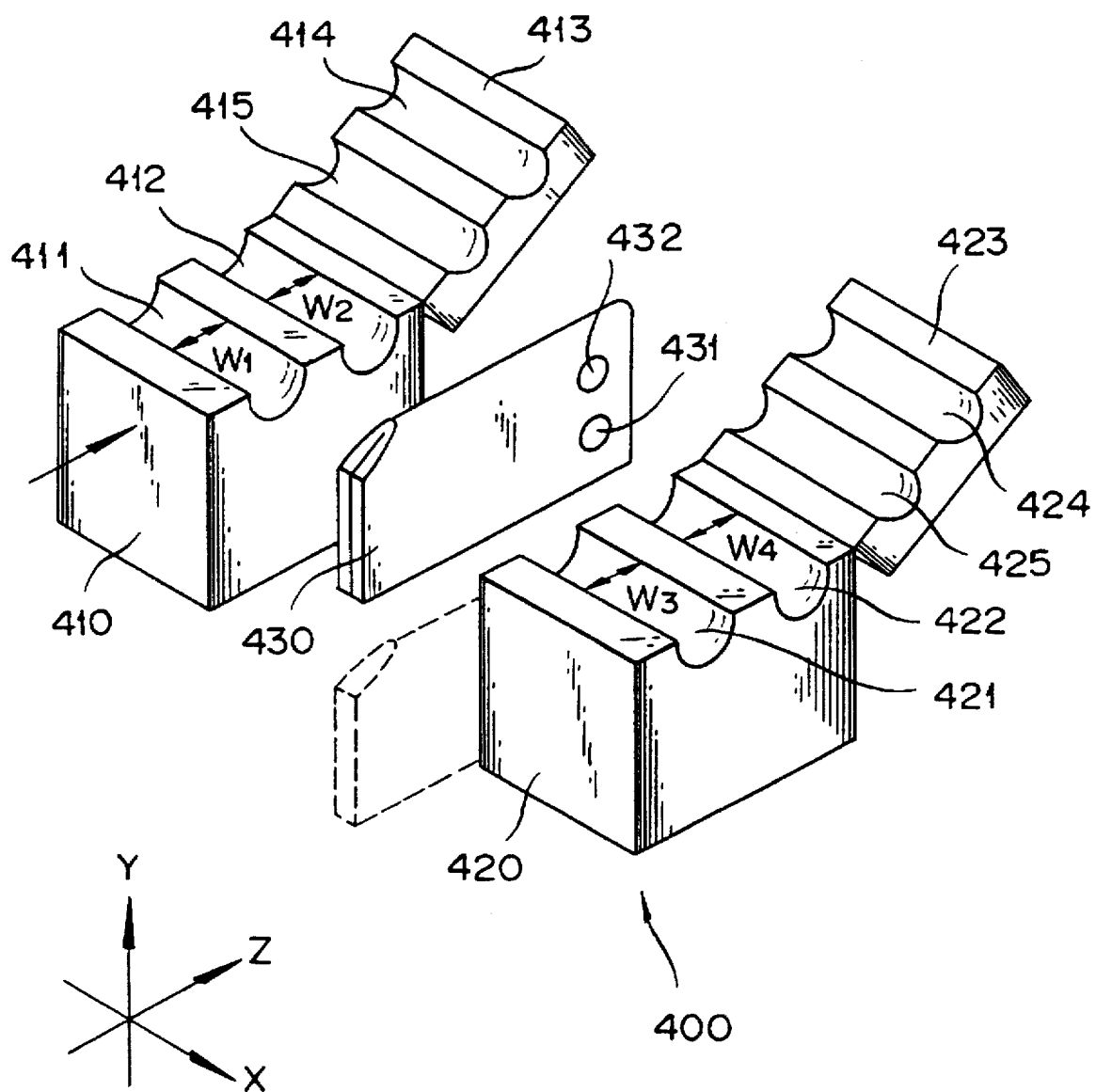
FIG. 17 is a perspective view illustrating the essential part of a tube connecting device.

FIG. 17 is a perspective view illustrating the essential parts of the tube connecting device 400. As illustrated in this diagram, the tube connecting device 400 comprises the paired holders 410 and 420 disposed along the direction of conveyance of the tube, a wafer (platelike heating element) 430 interposed between the two holders 410 and 420, moving means (not shown) serving the holder 410, moving means (not shown) serving the wafer 430, and electric power supplying means (not shown) serving the wafer 430.

The holder 420 is stationarily disposed relative to the tube connecting device 400 and the holder 410 is disposed so as to be moved in the direction of Z by use of unshown driving means.

On the upper side in the bearings of FIG. 17 of the holder 410, grooves 411 and 412 each of a U-shaped cross section are parallel formed. On the upper side in the bearings of FIG. 17 of the holder 420, grooves 421 and 422 each of the U-shaped cross section are parallel formed.

Incidentally, before the tube is loaded, the grooves 411 and 421 are disposed coaxially with the groove 305 formed in the conveying rail 302 and the grooves 412 and 422 are disposed coaxially with the groove 305 formed in the conveying rail 303.

The widths $W_1$ and $W_3$ of the grooves 411 and 421 are desired to be smaller than the external diameter of the tube 3 held in the no-load state thereof and larger than the external diameter of the tube 3 held in the state elongated by the chucks 353 and 354. Likewise, the widths $W_2$ and $W_4$ of the grooves 412 and 422 are desired to be smaller than the external diameter of the tube 7 or 752 held in the no-load state thereof and larger than the external diameter of the tube 7 or 752 held in the elongated state.

Above the holders 410 and 420, lids 413 and 423 are revolvably disposed. On the insides of these lids 413 and 423, grooves 414, 415, 424, and 425 which correspond respectively to the grooves 411, 412, 421, and 422 mentioned above are formed. The cross-sectional shapes of the grooves 411, 412, 421, 422, 414, 415, 424, and 425 are not limited to the letter U. They may be in the shape of three sides of a square or the shape of the letter V, for example.

The lids 413 and 423 may be so constructed as to be opened and closed automatically by use of a switching mechanism provided with a prescribed driving source.

Between the two holders 410 and 420, the wafer 430 which can be moved at least in the direction of Y (the vertical direction) in the bearings of FIG. 10 by use of wafer moving means is exchangeably disposed. This wafer 430 is constructed by doubling a sheet of such metal as copper over itself and forming on the inner surface thereof a heat-generating resistor (not shown) of a desired pattern through an insulating layer. Electric terminals 431 and 432 at the opposite ends of the resistor are severally exposed through openings formed in the metal sheet.

When the wafer 430 is powered through the two electric terminals 431 and 432 by used of electric power supplying means, it is heated to a temperature in the approximate range of 260° to 320° C., for example. This wafer 430 is desired to be of such type that it will deserve to be discarded after a single use in the connection of tubes. In this case, exchange of wafers 430 can be attained automatically by use of exchange means which is provided with a suitable driving source.

On the wafer 430 side end parts of the holders 410 and 420, tube chucking parts so adapted as to press the tube 3 and block the interior thereof when the lids 413 and 423 are closed may be provided, though not illustrated in the diagram.

The driving means for the holder 410, the driving means for the wafer 430, the electric power supplying means for the wafer 430, the driving sources for the wafer-exchange means and the lid-switching mechanism, and the moving means for a moving base 440 which will be specifically described hereinbelow are severally connected electrically to the control means 30 which also will be specifically described hereinbelow. The control means 30 controls the drive of the relevant component parts mentioned above.

By use of the tube loading device 350 mentioned above, the neighborhood of the downstream side end part of the tube 7 is loaded in the grooves 411 and 421 of the holders 410 and 420 and the neighborhood of the upstream side end part of the tube 3 is loaded in the grooves 412 and 422 of the holders 410 and 420. Now, the lids 413 and 423 are closed and then the tube connecting device 400 constructed as described above is operated to power the wafer 430 through the electric terminals 431 and 432 and heat it to a prescribed temperature, elevate the heated wafer 430 to fuse and out the two tubes, move the holder 410 in the direction of Z to a distance equivalent to the center-to-center distance of the grooves 411 and 412, match the cut surfaces of the two tubes 3, 7, lower and remove the wafer 430, and join the tube 3 and the tube 7 by fusion. Thus, the two tubes are airtightly connected.

According to the tube connecting device 400 of this operating principle, the connection of the two tubes 3, 7 can be aseptically accomplished because the downstream side end part of the tube 7 and the upstream side end part of the tube 3 are sealed by fusion prior to their connection and the inner cavities of the two tubes 3, 7 are never exposed to the ambient air during the course of the connection.

Short tube pieces (not shown) remain one each in the groove 412 of the holder 410 and the groove 421 of the holder 420 after the connection of the tubes 3, 7 is completed. Since these tube pieces are useless, they may be chucked, conveyed, and dumped into a separately installed waste recovery box (not shown) by the tube loading device 350. The wafer 430 which has fulfilled its role is likewise recovered in the waste recovery box.

In FIG. 1, the tube connecting device 400 is depicted to be so constructed that it will be disposed on a moving base 440 capable of being moved in the direction of Z by unshown moving means and then will be selectively positioned on the two tube conveying paths (the lines for transfer of blood components). This tube connecting device 400, when necessary, may be disposed exclusively to serve each line of transfer of blood components.

[Tube shape retention device 450]

Two tube shape retention devices 450 are disposed to serve each line of transfer of blood components, though not illustrated in FIG. 1, between the tube connecting device 400 and the container loading base 700 which will be specifically described hereinbelow or between the tube connecting device 400 and the tube sealing device 550 which also will be specifically described hereinbelow, for example. The parts of the tubes connected by the tube connecting device 400 are deformed into a flattened shape during the union by thermal fusion and the inner surfaces of the flattened tubes are bound possibly to the extent of blocking the inner flow paths of the tubes or decreasing the cross-sectional areas of the flow paths and consequently preventing the connected tubes from permitting ample flow of fluid. The tube shape retention device 450 is a tool for correcting the deformed joined parts of tubes and enabling the connected tubes to secure a normal flow path therein.

Figure 18:
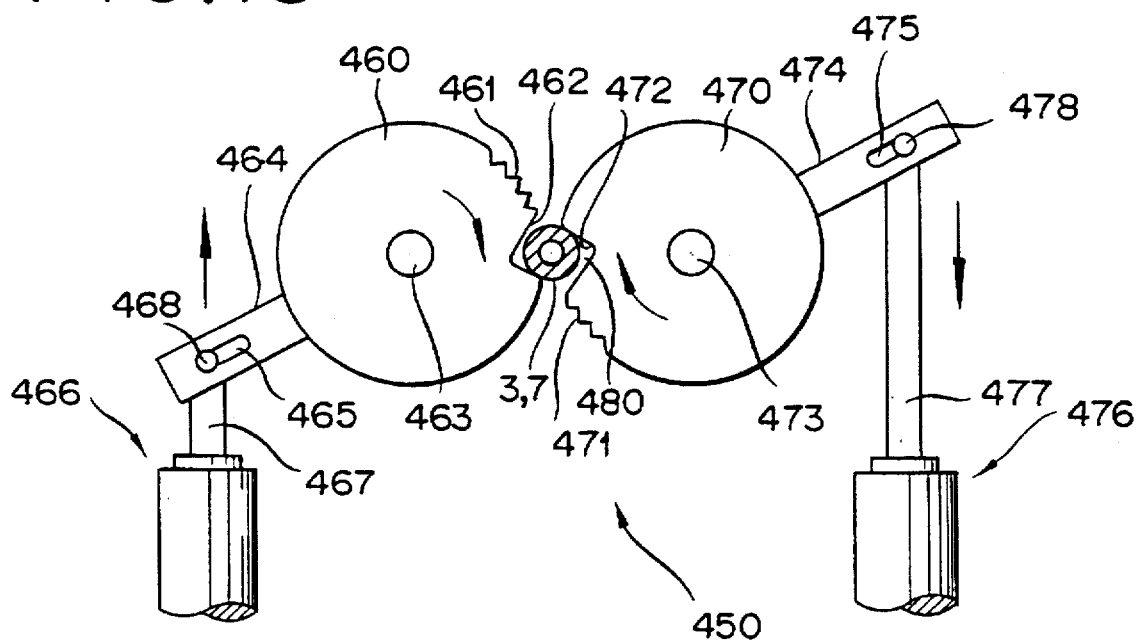
FIGS. 18 to 19 are side view each illustrating a tube shape retention device.
Figure 19:
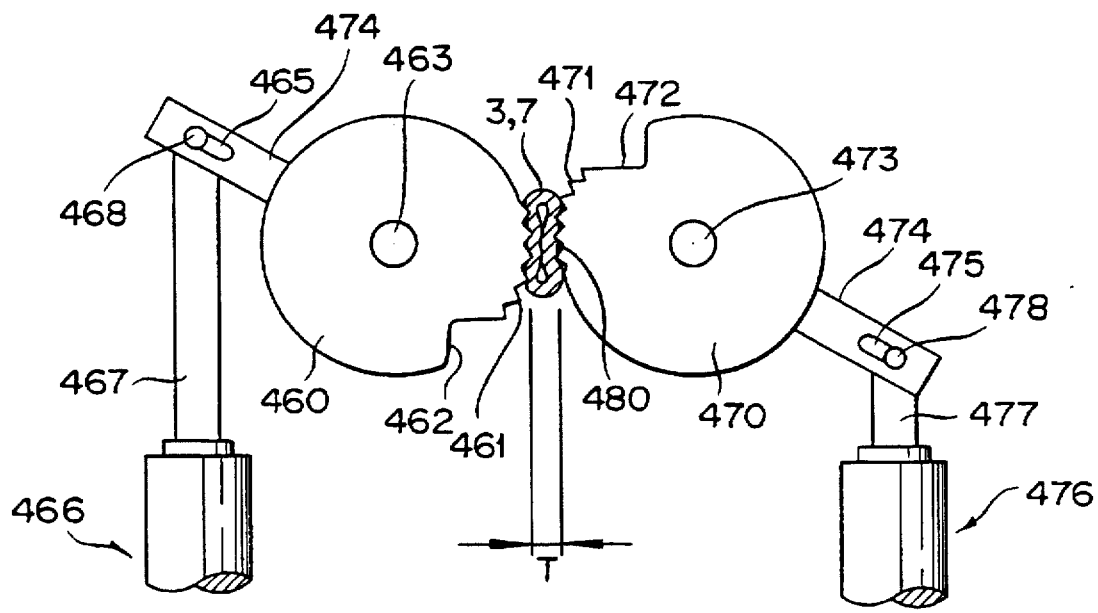

FIG. 18 and FIG. 19 are each a front view illustrating the tube shape retention device 450. This tube shape retention device 450 comprises a pair of pressing rollers 460 and 470 and are provided as members for pressing tubes, shaking arms 464 and 474, and reciprocating mechanisms 466 and 476 intended as driving means for rotating the pressing rollers 460 and 470 through the shaking arms 464 and 474.

The pressing rollers 460 and 470 are cylindrical in shape and are pivotally supported in mutually parallel positions by rotary shafts 463 and 473 which are mutually parallel supported in place. A prescribed gas is interposed between the pressing rollers 460 and 470.

On the peripheral surfaces of the pressing rollers 460 and 470, notches 462 and 472 each of the shape of a groove are formed as extended in the axial direction of the pressing rollers. By rotating the pressing rollers 460 and 470 severally in the same direction thereby moving the two notches 462 and 472 to the opposed positions as illustrated in FIG. 18, the notches 462 and 472 jointly define a tube-insertion path 480 for permitting passage of a tube between the pressing rollers 460 and 470. This tube-insertion path 480 has a size enough for allowing the tube to obtain easy passage while keeping the normal cross section thereof intact.

Pressing faces 461 and 471 having knurls formed thereon are provided on the peripheral surfaces of the pressing rollers 460 and 470 adjoining one side ends of the notches 462 and 472. These pressing faces 461 and 471 are curved at a ratio of curvature proportionate to the ratio of curvature of the peripheral surfaces of the pressing rollers 460 and 470. When the pressing rollers 460 and 470 are rotated in the same direction from the positions thereof opposite the tube-insertion path 480, the pressing faces 461 and 471 are opposed to each other. The spacing distance T which separates the pressing faces 461 and 471 which are held in the opposed state is desired to be slightly smaller than the difference between the external diameter and the internal diameter of the tube (=α) to be passed. Specifically, the spacing distance T is desired to be in the approximate range of 50 to 95%, preferably 70 to 90%, of α.

To the pressing rollers 460 and 470, shaking arms 464 and 474 adapted to shake (revolve) around the rotary shafts 463 and 473 are respectively fixed. The two shaking arms 464 and 474 are disposed as projected in the radial directions of the pressing rollers 460 and 470. In the projecting ends of the shaking arms 464 and 474, oblong holes 465 and 475 extending along the longitudinal directions of the shaking arms 464 and 474 are formed. Reciprocating mechanisms 466 and 476 are provided on the extensions of the directions in which the leading ends of the shaking arms 464 and 474 are shaken. A pneumatic actuator, for example, is used as the driving source for the reciprocating mechanisms 466 and 476 contemplated in the present example. From the leading ends of driving rods 467 and 477 for the pneumatic actuator, pins 468 and 478 are respectively projected. These pins 468 and 478 are inserted respectively in the oblong holes 465 and 475 of the shaking arms 464 and 474.

The reciprocating mechanisms 466 and 476 are not always required to be operated by the pneumatic actuator. Optionally, they may be constructed so as to be actuated by a hydraulic cylinder. Alternatively, displacing mechanisms adapted to effect necessary displacement by a cam mechanism or electrically driving means may be adopted instead of the reciprocating mechanisms 466 and 467. The driving sources for these reciprocating mechanisms 466 and 476 are severally connected electrically to the control means 30 which will be specifically described hereinbelow. The control means 30 controls the drive thereof. As other driving means for rotating the pressing rollers 460 and 470, the motor adopted for rotating the rotary shafts 463 and 473 may be used.

In the tube shape retention device 450 constructed as described above, while the notches 462 and 472 are in the mutually opposed state as illustrated in FIG. 18, the tube conveying device 300 is operated to convey the tubes 3, 7, and 752 until the deformed parts of the tubes produced in consequence of the union of tubes are positioned in the tube-insertion path 480.

Then, the reciprocating mechanisms 466 and 476 are actuated to induce at least one reciprocating motion of the pressing rollers 460 and 470. Specifically, owing to the withdrawal of the driving rods 467 and 477 in consequence of the presence or absence of the action of the pneumatic actuator, the shaking arms 464 and 474 are shaken around the rotary shafts 463 and 473 to rotate the pressure rollers 460 and 470 through the pins 468 and 478 and the oblong holes 465 and 475.

When the pressure rollers 460 and 470 are revolved as shown in FIG. 19, the tube is chucked and crushed by the pressing faces 461 and 471 and the inner surface of the crushed part of the tube is twisted as though it were rubbed against itself. The adhesion of the inner surfaces of the tube is undone by merely crushing the tube. When the tube is kept in the crushed state and then rotated in such a manner that the inner surface thereof will rub against itself, the fusion of the inner surface of the tube is infallibly undone. As a result, the tube resumes the original cross section or a shape approximating it and secures a normal flow path therein.

When the recovery of the shape of the tube preformed as described above is completed, the reciprocating mechanisms 466 and 476 are actuated to rotate the pressing rollers 460 and 470, cause the notches 462 and 472 to be opposed again to each other, and give rise to the tube-insertion path 480 and permit conveyance of the tube therethrough.

In this invention, the deformation in the connected parts of tubes may be corrected by normally/reversely rotating the roller 311 or 312 in the tube conveying device 300 or rollers 501 and 502 in the hereinbelow specified tube squeeze device 500 thereby inducing at least one reciprocating motion of the connected parts of the tubes between the relevant rollers instead of resorting to the tube shape retention device 450 which is intended exclusively for the purpose of the recovery.

[Tube squeeze device 500]

Between the tube sealing device 550 which will be specifically described hereinbelow and the Container loading base 700 or between the tube connecting device 400 and the tube sealing device 550, two tube squeeze devices 500 are installed, though not illustrated in FIG. 1, to serve each line of transfer of blood components.

Figure 21:
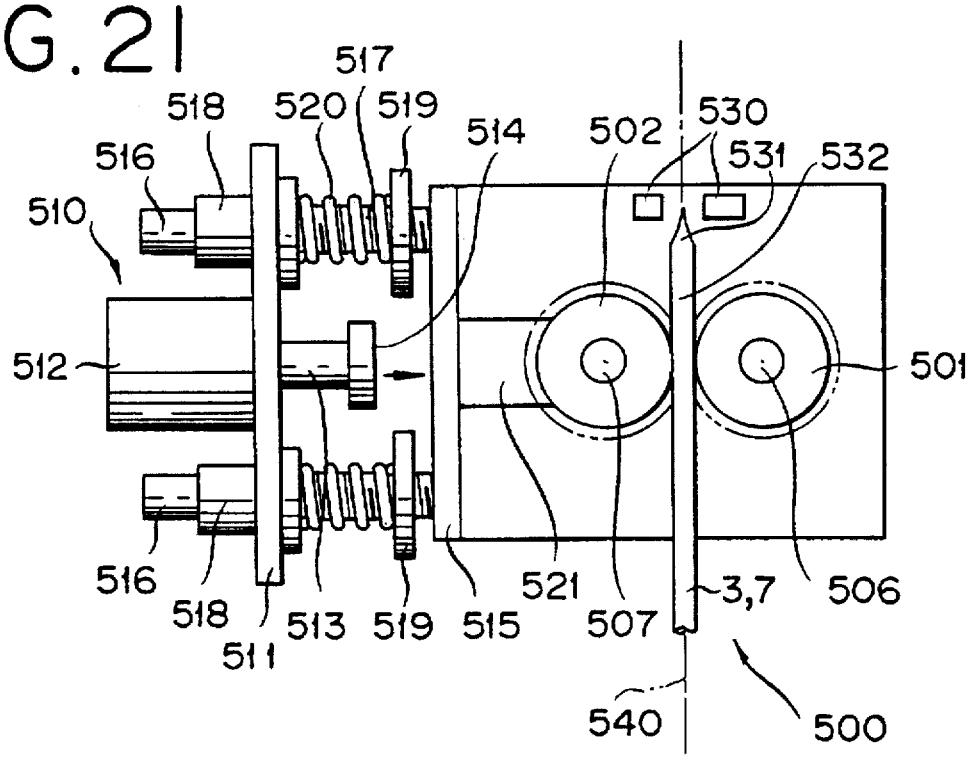
FIGS. 21 and 22 are front views each illustrating the tube squeeze device.
Figure 22:
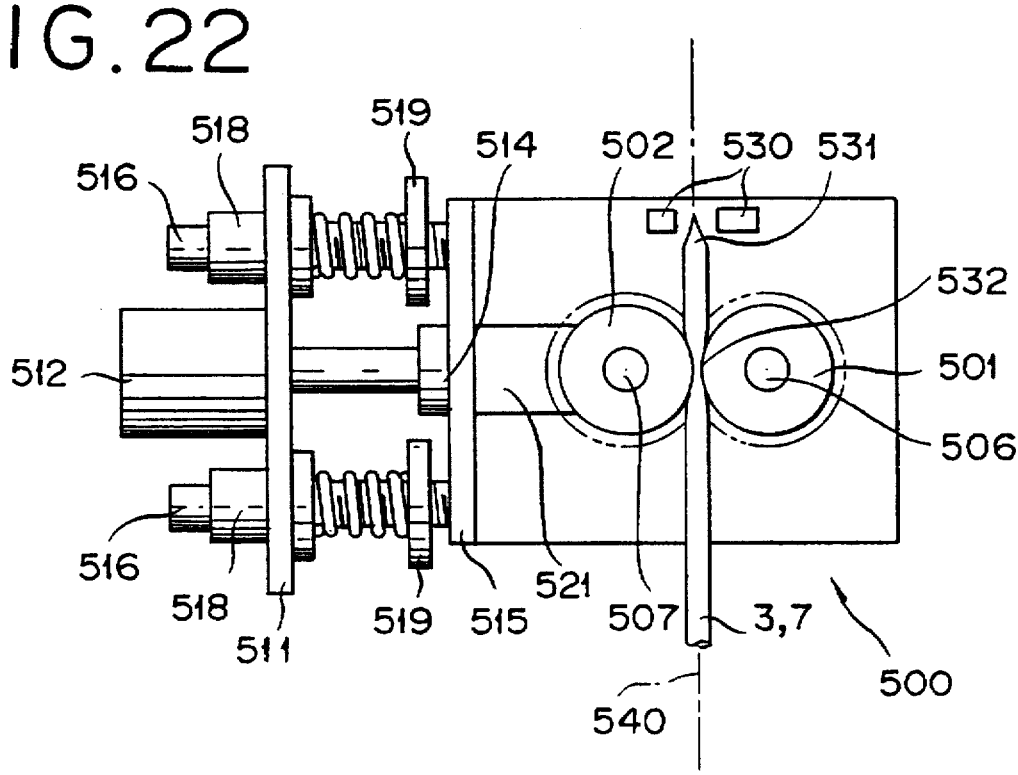

FIG. 2C is a front view illustrating the tube squeeze device 500. FIG. 21 and FIG. 22 are each a plan view of the tube squeeze device 500. As illustrated in these diagrams, the tube squeeze device 500 is composed of a pair of rollers 501 and 502 opposed to each other across a path 540 for conveyance of the tubes 3, 7, and 752, roller rotating means 503 for rotating at least the roller 501 in a prescribed direction, and displacing means 510 for varying the distance separating the two rollers 501 and 502.

In the present example, the roller 502 is employed as a counterpart for the roller 501. Some other counterpart (such as, for example, a plate member or a blocklike member) than the roller 502 may be used when necessary.

The rollers 501 and 502 may be identical or not identical with each other in shape, size (external diameter, width, etc.), and material, for example. In the present example, they are wholly identical in the factors mentioned above.

The roller rotating means 503 is composed of a motor 504 as a driving source, a reduction gear 505 for decelerating the rotation of the motor 504, a driving shaft 506 connected to the main shaft of the reduction gear 505, a driven shaft 507, a toothed wheel 508 fixed to the driving shaft 506, and a toothed wheel 509 fixed to the driven shaft 507 and allowed to be meshed with the toothed wheel 508 mentioned above. The roller 501 is fixed to the leading end part of the driving shaft 506 and the roller 502 is fixed to the leading end part of the driven shaft 509.

The motor 504 is desired to be capable of normal/reverse rotation. As concrete examples of the motor which answers this description, ordinary DC or AC motors (such as stepping motors, servomotors, CB motors, and speed-control motors) may be cited. It is permissible to use a pneumatic or hydraulic rotary drive or actuator instead.

In the roller rotating means 503 constructed as described above when the motor 504 is set rotating, this rotation is decelerated by the reduction gear 505 and transmitted to the driving shaft 506, with the result that the roller 501 will be rotated in the prescribed direction. When the toothed wheels 508 and 509 are in the mutually meshed state (in the state shown in FIG. 2), the rotating force of the driving shaft 506 is transmitted even to the driven shaft 507 through the toothed wheels 508 and 509, with the result that the roller 502 will be rotated in the direction opposite to that of the roller 501. In this case, for the purpose of causing the tube to advance straight, the toothed wheels 508 and 509 have an equal number of teeth and the rollers 501 and 502 are disposed so as to produced an equal revolution number.

The roller rotating means 503 is not always required to be constructed as illustrated in the drawing. For example, the rollers 501 and 502 may be severally driven by separate motors when necessary. Optionally, the roller 501 alone may be rotated.

Figure 20:
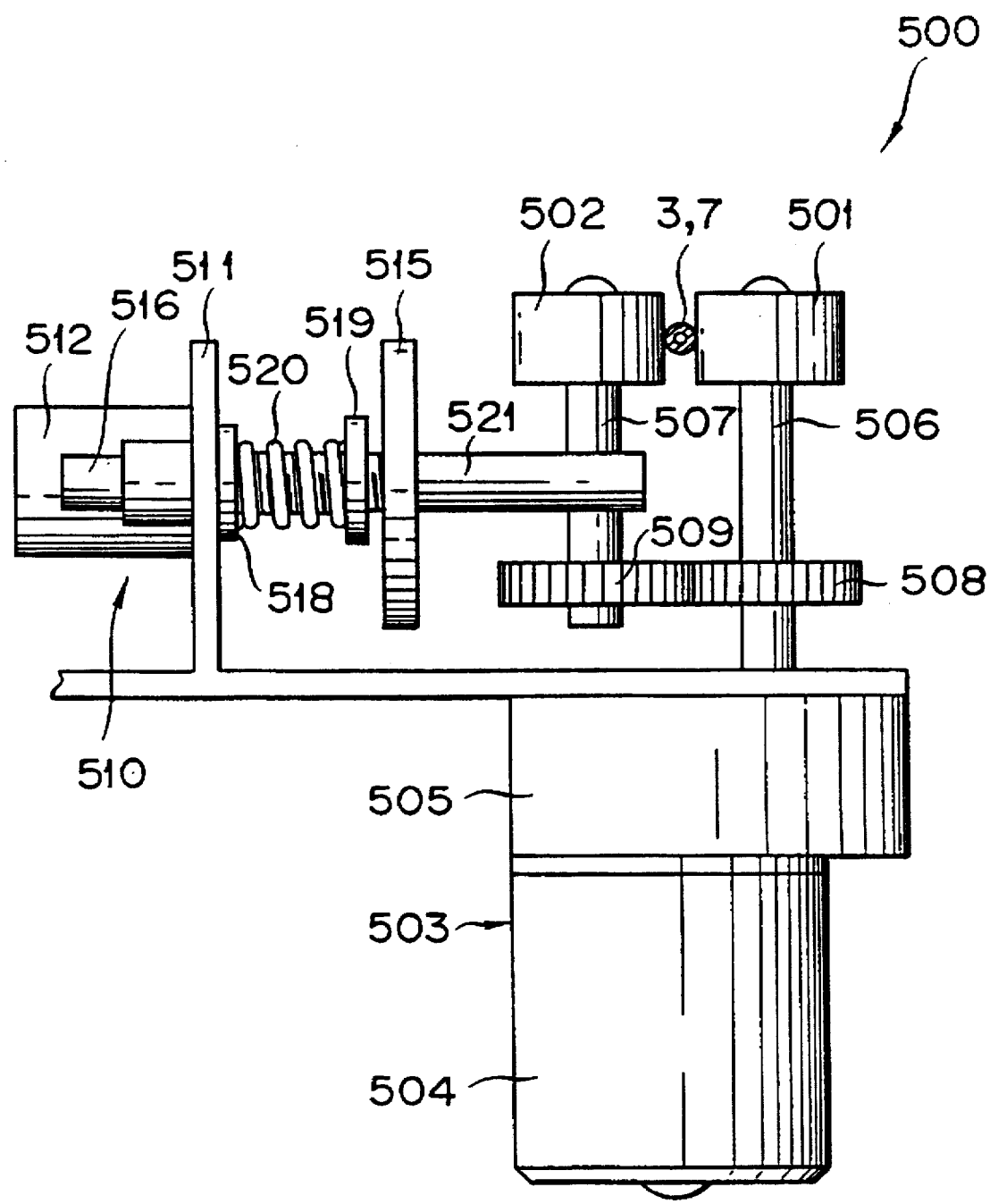
FIG. 20 is a side view illustrating a tube squeeze device.

The displacing means 510 is composed of a supporting base 511 disposed upright relative to the main body 15 of the apparatus, a cylinder 512 fixed to the left side in the bearings of FIG. 20 of the supporting base 511, a plunger 513 adapted to reciprocate in the vertical direction in the bearings of FIG. 21 relative to the cylinder 512, a pressing head 514 disposed on the upper end in the bearings of FIG. 21 of the plunger 513, a moving base 515, two rods 516 fixed substantially vertically relative to the moving base 515 on the left side in the bearings of FIG. 20 of the moving base 515, two guide members 518 supporting the two rods 516 so as to impart to the rods a sliding motion in the longitudinal directions thereof, two adjusting rings 519 adapted severally to be meshed with screws 517 formed on the right end part peripheral faces of the two rods 516, two springs 520 between the guide members 518 and the adjusting rings 519 on the peripheral parts of the two rods 516, and a supporting member 521 fixed on the right side in the bearings of FIG. 20 of the moving base 515 and rotatably supporting the driven shaft 507.

As a concrete example of the cylinder 512, a cylinder which is actuated pneumatically or hydraulically may be cited. It is permissible to use solenoid in the place of the cylinder.

The adjusting ring 519 is intended to adjust the pressure which the rollers 501 and 502 exert on the tube in chucking the tube without inducing blockage of the internal cavity of the tube. When this adjusting ring 519 is rotated relative to the rod 516, it moves on the rod 516 in the longitudinal direction thereof. The chucking pressure which the rollers 501 and 502 exert on the tubes 3, 7 increases in proportion as the distance between the adjusting ring 519 and the moving base 515 increases.

While the cylinder 512 is not in action and the plunger 513 is in the withdrawn state (with the pressing head 514 separated from the moving base 515) as illustrated in FIG. 20 and FIG. 21, the adjusting ring 519 is urged by the elastic force of the spring 520 toward the right in the bearings of FIG. 21 and consequently the rod 516, the moving base 515, the supporting member 521, and the roller 502 are urged toward the right in the bearings of FIG. 21. As a result, the two rollers 501 and 502 chuck the tubes 3, 7, for example, to the extent of causing no blockage of the inner cavities thereof (hereinafter referred to as a "chucked state"). In the chucked state, the toothed wheels 508 and 509 may be meshed feebly or may not be meshed at all. In the latter case, the roller 502 becomes an idle roller (free roller) which is capable of free rotation.

When the roller 501 or the rollers 501 and 502 are rotated in a prescribed direction by the roller rotating means 503 while the tube is in the chucked state mentioned above, the tube is conveyed along a conveying path 540.

When the plunger 513 is elongated by the action of the cylinder 512 as shown in FIG. 22, the pressing head 514 collides against the left side surface in the bearings of FIG. 22 of the moving base 515 and then pushes and moves the moving base 515 toward the right in the bearings of FIG. 22. As a result, the roller 502 approaches the roller 501 more closely and collapses the tubes 3, 7 to the extent of blocking the inner cavities thereof (hereinafter referred to as "collapsed state"). While the tubes 3, 7 are in the collapsed state mentioned above, the toothed wheels 508 and 509 are in a meshed state (which state constitutes itself no essential requirement).

When the rollers 501 and 502 are rotated in the prescribed direction by the roller rotating means 503 while the tubes are in the collapsed state mentioned above, the tubes 3, 7 as kept in the collapsed state are conveyed along the conveying path 540 while keeping the collapsed state intact. The tubes are squeezed as a result.

Figure 23:
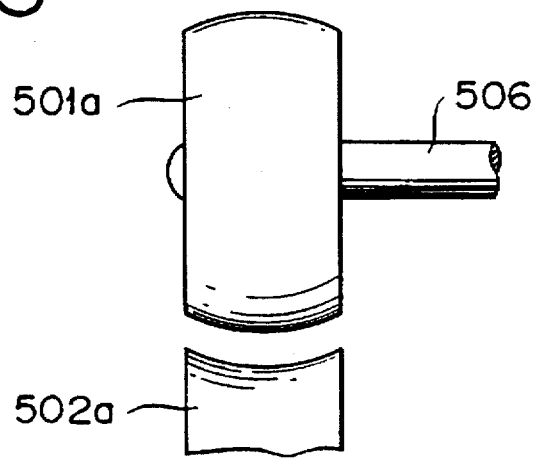
FIG. 23 is a side view illustrating another example of the roller in the tube squeeze device.
Figure 24:
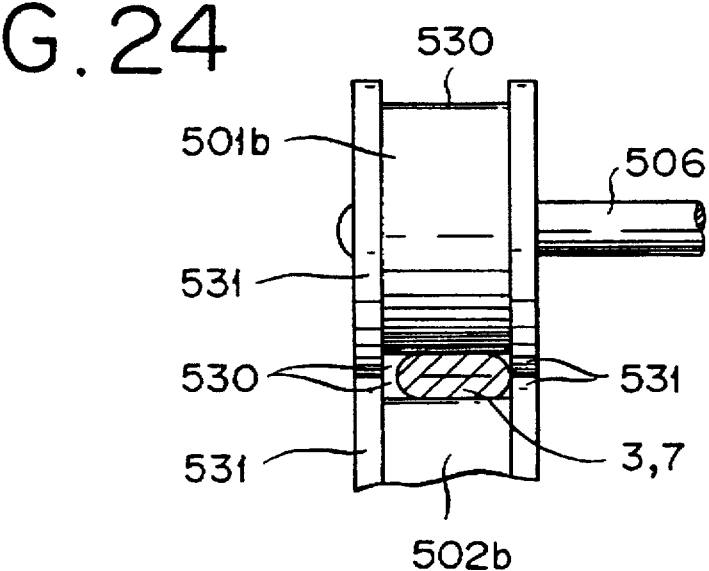
FIG. 24 is a front view illustrating still another example of the roller in the tube squeeze device.
Figure 25:
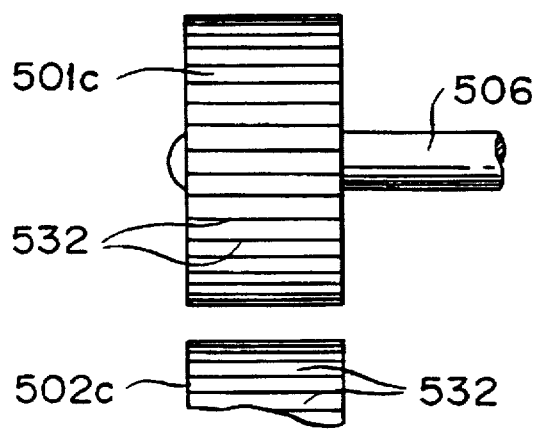
FIG. 25 is a front view illustrating yet another example of the roller in the tube squeeze device.

FIG. 23, FIG. 24, and FIG. 25 are each a front view illustrating an example of the other construction of rollers for squeezing the tubes 3, 7. Rollers 501a and 502a illustrated in FIG. 23 have the peripheral faces thereof curved outward or inward in the direction of width of the rollers, whereas the rollers 501 and 502 illustrated in FIG. 21 and FIG. 22 have flat peripheral faces in the direction of width (the direction of axis of rotation) of the rollers. The rollers 501a and 502a so constructed as described above can prevent the tubes 3,7 from slipping off the space intervening between the rollers when they engage in the work of squeezing the tubes 3, 7.

Rollers 501b and 502b illustrated in FIG. 24 severally have a groove 530 formed in the central part in the direction of width of the peripheral face thereof. Inside the grooves 530 of the two rollers, the tubes 3, 7 are chucked or collapsed. In this case, the depth of the groove 530 is so adjusted that the inner cavities of the tubes 3, 7 will be blocked when the opposite end parts in the direction of width of the two rollers 501b and 502b contact each other. The rollers 501b and 502b constructed as described above can effect the blockage of the inner cavities of tubes infallibly and uniformly without excessively pressing the tubes 3, 7 when the tubes 3, 7 are being squeezed.

Rollers 501c and 502c illustrated in FIG. 25 severally have convexo-concave ribs (knurl) 532 formed on the peripheral surfaces thereof as extended along the direction of width of the rollers. The rollers 501c and 502c thus constructed can prevent themselves from slipping on the tubes 3, 7 when they chuck and convey the tubes 3, 7 or when they squeeze the tubes 3, 7.

The rollers 501a, 501b, 501c, 502a, 502b, and 502c are not specifically limited to any particular material for their manufacture. For the purpose of enhancing their ability to convey the tubes 3, 7, however, they are desired to have at least the peripheral surfaces thereof formed of a varying rubber material such as, for example, natural rubber, isoprene rubber, butadiene rubber, silicone rubber, nitrile rubber, propylene rubber, or urethane rubber or an elastic material such as, for example, polyurethane or thermoplastic elastomer (of the styrene type, olefin type, urethane type, or ester type).

For use in the tube squeeze device 500, the displacing means does not need to be limited to the illustrated type which effects displacement of the roller 502 exclusively. It may be so adapted that both the rollers 501 and 502 will be severally displaced, for example.

In the tube squeeze device 500, an optical sensor (photo-interrupter) 530 which is composed of a light emitting element and a light receiving element opposed to each other across the conveying path 540 is installed as illustrated in FIG. 21 and FIG. 22 to serve as detecting means for detecting the positions at which the tubes 3, 7 begin to be squeezed. This optical sensor 530 is disposed at the position of the leading end 531 of the tube when the start position for squeezing of the tubes intervenes between the rollers 501 and 502. Thus, the start position 532 for squeezing of the tubes falls between the rollers 501 and 502 when the optical sensor 530 detects the leading end 531 of the tube.

The leading end 531 of the tube (sealed portion 75) of the tube, as illustrated in FIG. 21 and FIG. 22, assumes a flattened state (as shown in FIG. 33) because it has been sealed and out by the tube sealing device 550. It is optional to have the tube squeezed by the tube squeeze device 500 before it is sealed and cut by the tube sealing device 550.

The detecting means for detecting the start position 532 for squeezing of the tube does not need to be limited to the construction mentioned above. For example, it may be so constructed as to attain the detection in question by utilizing the amount of rotation of the roller 501 which is required for conveying the tube over a length equivalent to the distance from a prescribed position of the tube (for example, the leading end 531) to the start position 532 for squeezing or so constructed as to effect the detection by utilizing an optically, electrically, or magnetically discernible marker affixed at the start position 532 for squeezing of the tube or at a position separated by a prescribed distance from the start position 532 for squeezing.

The control means 30 which will be specifically described hereinbelow controls the drive timing, direction of rotation, speed of rotation, amount of rotation, and duration of rotation of the motor 504 and the timing of operation of the cylinder 512, etc. as occasion demands in response to the input from the operator console 40 or the signal of detection at the sensor 530.

The tube squeeze device 500 constructed and operated as described above is desired to be provided with detecting means capable of detecting the end position for squeezing of the tubes 3, 7. Now, examples of the construction of this detecting means will be described below.

When the length from the start position for squeezing of the tubes 3, 7 to the end position for squeezing (hereinafter referred to as "squeeze length") is known, the roller rotating means 503 is used to detect the amount of rotation of the roller 501 and, based on the detected amount of rotation, fixes the position for squeezing of the tubes 3, 7. Specifically, after the two rollers 501 and 502 have chucked and exerted tight pressure on the tubes 3, 7, the rotation of the roller 501 is stopped when the amount of rotation of the roller 501 required for conveying the tubes 3, 7 over the squeeze length is detected.

As concrete examples of the method for detecting the amount of rotation of the roller 501 operated by use of a stepping motor as the motor 504, for example, a method which resorts to the detection of the number of steps of the motor, a method which relies on the direct detection of the amount of rotation by means of an encoder incorporated in the motor 504 or the roller 501, and a method which consists in measuring and controlling the time for driving the motor 504 may be cited.

Figure 26:
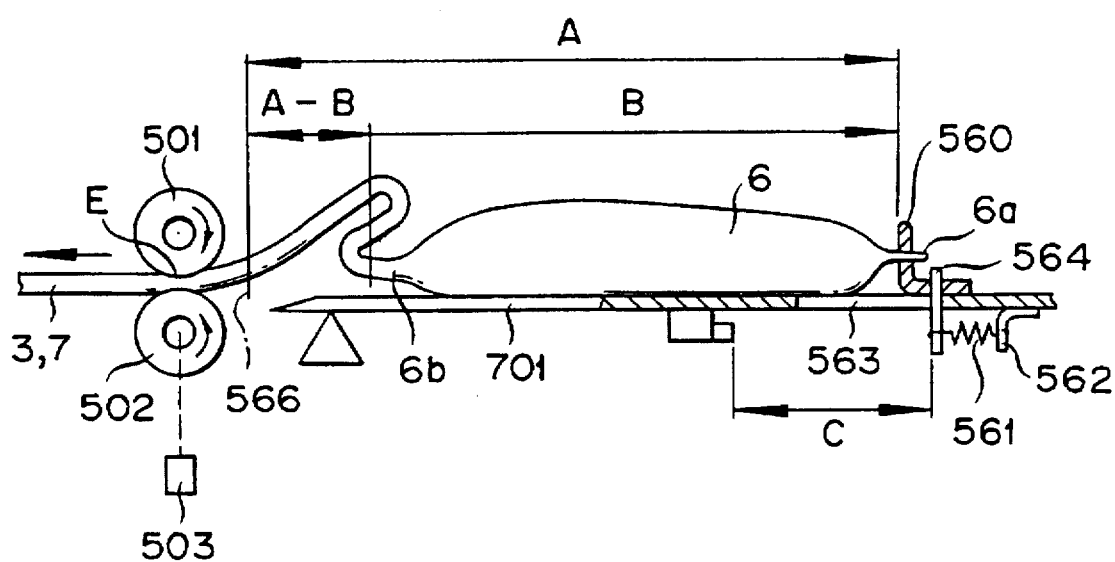
FIGS. 26 to 29 are side views each illustrating detecting means for detecting the position at which the tube squeeze device terminates the squeezing action thereof exerted on the tube.
Figure 27:
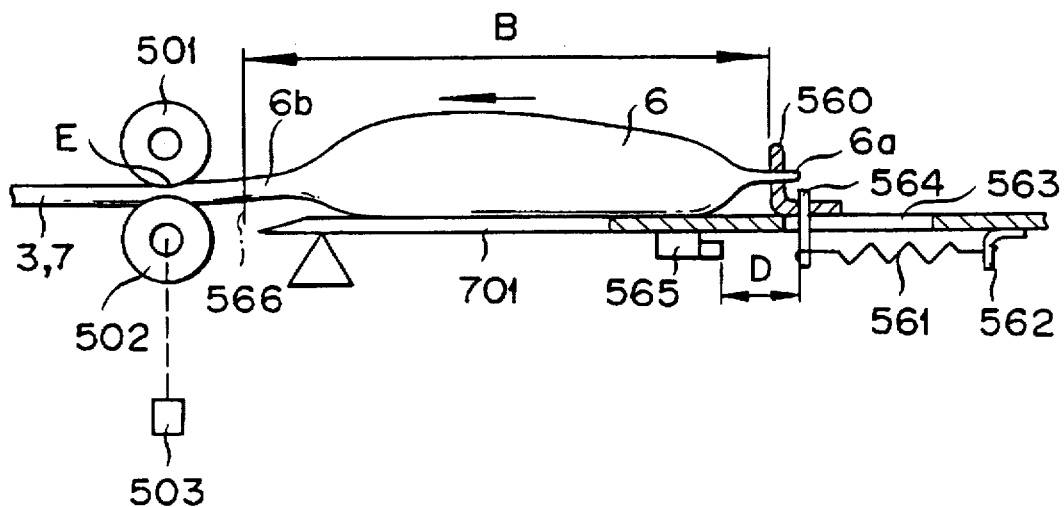

The squeeze length of the tubes 3, 7 is a matter of arbitrary decision. The detection means to be used when the total length of the bag 6 is already known may be constructed, for example, as illustrated in FIG. 26 and FIG. 27. In the rear end part (the right side in the bearings of the diagrams) of a loading board 701, a rear end part 6a of the bag 6 is fixed and, at the same time, a slider 560 slidable in the longitudinal direction of the bag 6 relative to the loading board 701 is disposed as illustrated in the diagrams. This slider 560 is kept urged by a spring 561 toward the rear end side (the right in the bearings of the diagrams) of the loading board 701. Specifically, one end of the spring 561 is fixed on the reverse surface side of the rear end part of the loading board 701 by use of a fixing member 562 and the other end of the spring 561 is fixed to a pin 564 raised from the slider 560, passed through an oblong hole 563 formed in the loading board 701, and projected on the reverse surface side of the loading board 701.

Besides, a sensor 565 which is capable of detecting the distance from the pin 564 (or the contact with or the approach of the pin 564) is disposed on the reverse surface of the loading board 701. The detection signal from this sensor 565 is input into the control means 30.

As concrete examples of the sensor 565, touch switches, optical sensors like a photo-interrupter, linear encoders, laser distance meters, and magnetic sensors may be cited.

Now, the method for detecting the end position for squeezing of the tubes 3, 7 by use of the detecting means just mentioned will be described below.

The position which the leading end of the bag 6 assumes when the squeezing of the tubes 3, 7 is terminated, namely when the end position E for terminating the squeezing of the tubes 3, 7 falls between the two rollers 501 and 501 as shown in FIG. 27, is designated as a reference position 566 and the length from this reference position 566 to the leading end of the slider 560 is denoted by A, the total length of the bag 6 by B, and the distance from the pin 564 to the sensor 565 by C respectively as shown in FIG. 26.

When the tubes 3, 7 are still intervening in a sagging state between the rollers 501, 502 and the bag 6 as shown in FIG. 26, the two rollers 501 and 502 are set rotating and exerting a squeezing action on the tubes 3, 7. Shortly, the tubes 3, 7 between the two rollers 501, 502 and the bag 6 cease to retain the sagging state. As the tubes 3, 7 are further conveyed by the rotation of the rollers 501 and 502, they draw the bag 6. The bag 6 and the slider 560 are consequently moved toward the leading end (the left in the bearings of the diagram) in spite of the resilient force of the spring 561.

In the meantime, the sensor 565 is operating to detect the distance between itself and the pin 564 from time to time. When this distance grows to D(=C−A+B) as shown in FIG. 27, the control means 30 concludes that the end position E for terminating the squeezing of the tubes 3, 7 falls between the two rollers 501 and 502 and then directs the roller rotating means 503 to stop rotating the rollers 501 and 502. When the sensor 565 happens to be a touch switch, it is set at a position indicated by the status C=A−B and is actuated to stop the rotation of the rollers 501 and 502 when the pin 564 collides against the contactor of the sensor 565, hence the status D=0.

Figure 28:
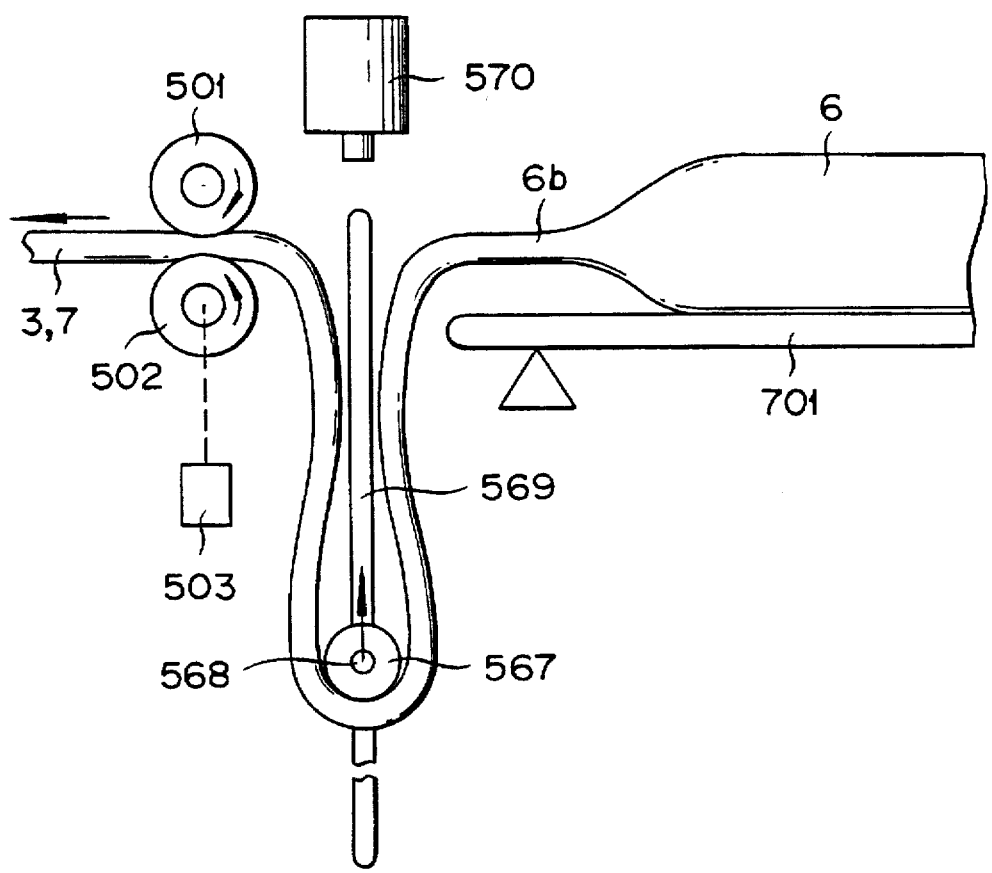
Figure 29:
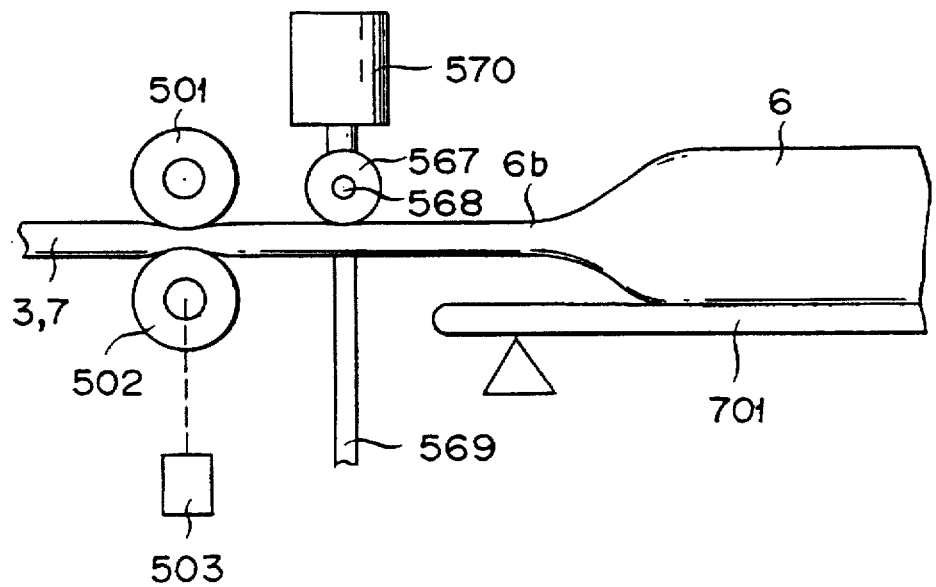

As detecting means which meets the conditions that the squeeze length of the tubes 3, 7 and the total length of the bag 6 are arbitrary, a device constructed as shown in FIG. 28 and FIG. 29 may be cited. A roller 567 for winding the tubes 3, 7 thereon is disposed between the rollers 501 and 502 and the leading end of the loading board 701 as shown in these diagrams. A shaft 568 of this roller 567 has the opposite ends thereof inserted severally in oblong holes 569 extended in the vertical direction in the bearings of the diagrams. Owing to this arrangement, the roller 567 is free to rotate about the shaft 568 as the center and move in the vertical direction along the oblong holes 569.

A sensor 570 for detecting the ascent of the roller 567 to a prescribed position is disposed above the roller 567. The signal of detection output from this sensor 570 is input into the control means 30. The sensor 570 illustrated in the diagram is a touch switch which is capable of sensing a touch of the roller 567. Optionally, a sensor similar to the sensor 565 mentioned above may be used instead.

The bag 6 seated on the loading board 701 has a rear end part 6a thereof fixed to the loading board 701. In this case, the position for fixing the bag 6 relative to the loading board 701 is so set that the end position E for terminating the squeezing of the tubes 3, 7 will fall between the two rollers 501 and 502 when the tubes 3, 7 intervening between the rollers 501, 502 and the bag 6 assume a straight taut state as shown in FIG. 29.

Incidentally, the end position E for terminating the squeezing of the tubes 3, 7 is desired to be in the neighborhood of the parts of the tubes 3, 7 connected to the bag 6. Thus, the squeeze length is both ample relative to the total length of the tubes 3, 7 and enough to attain effective discharge of liquid and gas from within the tubes 3, 7 into the bag 6.

Now, the method for detecting the end position E for terminating the squeezing of the tubes 3, 7 by use of the aforementioned detecting means will be described below.

When the tubes 3, 7 intervening between the rollers 501, 502 and bag 6 are still in the sagging state as shown in FIG. 28, the two rollers 501 and 502 are set rotating and exerting a squeezing action on the tubes 3, 7. As a result, the sag produced by the tubes 3, 7 which intervene between the two rollers 501, 502 and the bag 6 gradually dwindles and the roller 567 consequently ascends.

When the tubes 3, 7 intervening between the rollers 501, 502 and the bag 6 finally assume a straight taut state as shown in FIG. 29, a roller 539 collides against the contactor of the sensor 570. As a result, the control means 30 concludes that the end position E for terminating the squeezing of the tubes 3, 7 falls between the two rollers 501 and 502 and then directs the roller rotating means 503 to stop rotating the rollers 501 and 502.

The detecting means for detecting the end position for squeezing of the tubes 3, 7 is not limited to the varying construction described above. It is optional to construct the detecting means so as to effect the detection of the position under discussion by utilizing an optically, electrically, or magnetically discernible marker which is affixed at the end position E for terminating the squeezing of the tubes 3, 7 or at a position separated by a prescribed distance from the end position E mentioned above.

Figure 30:
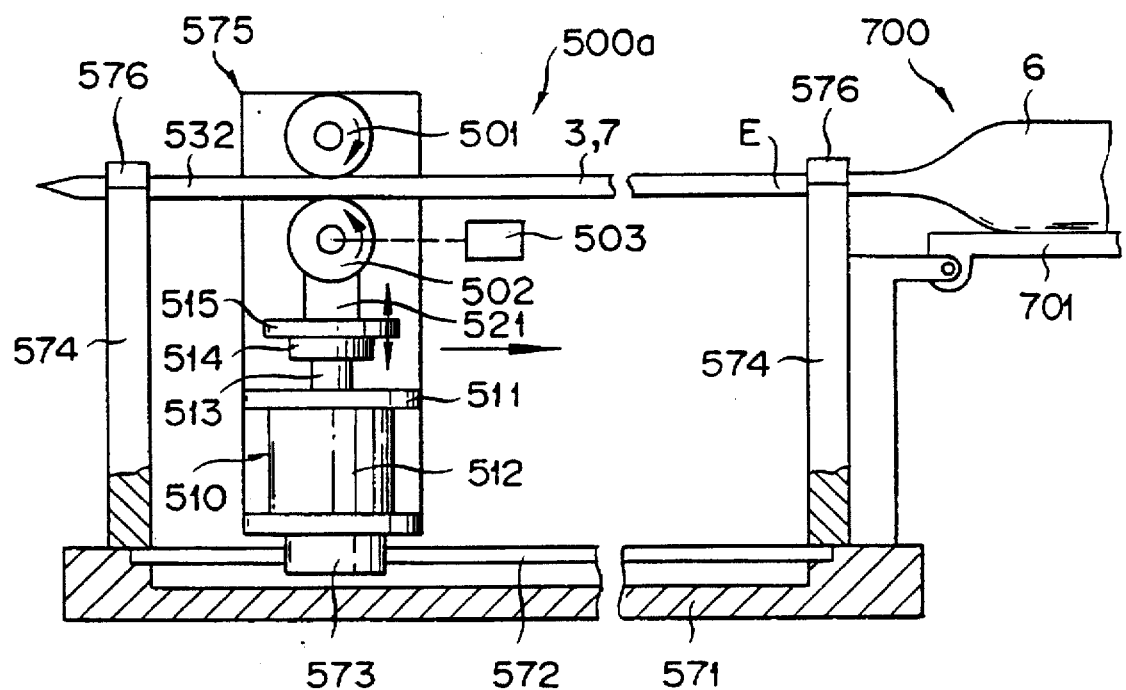
FIGS. 30 and 31 are partially sectioned side views each illustrating the tube squeeze part of the tube squeeze device.
Figure 31:
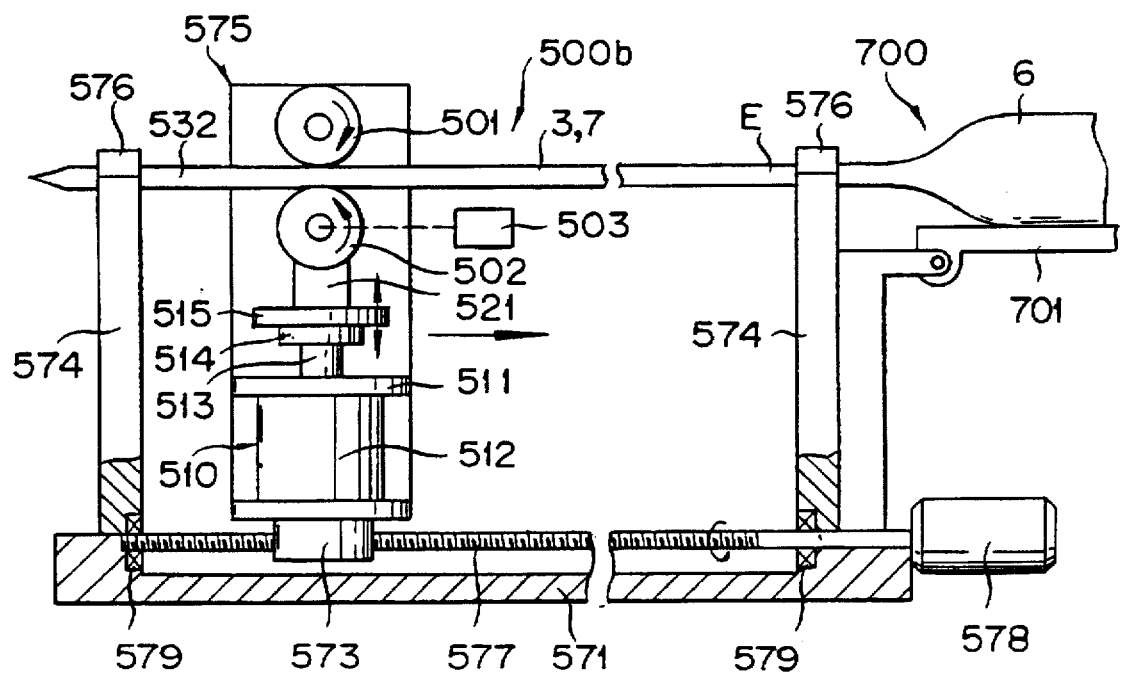

FIG. 30 and FIG. 31 are each a partially sectioned side view illustrating an example of the other construction of the tube squeeze device.

A tube squeeze device 500a illustrated in FIG. 30 is composed of a base 571, a guide bar 572 fixed to the base 571, a slider 573 adapted to slide on the guide bar 572, supporting members 574 severally erected on the opposite ends of the base 571, and a moving member 575 which comprises the same rollers 501 and 502 as mentioned above, the same roller rotating means 503 as mentioned above, and the displacing means 510 for vertically reciprocating the roller 502.

The slider 573 is fixed in the lower part of the moving member 574. The displacing means 510 is composed of the same supporting base 511 as mentioned above, the cylinder 512, the plunger 513, the pressing head 514, the moving base 515, and the supporting member 521.

In the upper end parts in the bearings of the diagram of the two supporting members 574, supporting parts 576 capable of detachably supporting (chucking) and fixing the tubes 3, 7 are severally formed.

In the tube squeeze device 500a constructed as described above, the moving member 575 is moved toward the right in the bearings of the diagram and enabled to squeeze the tubes 3, 7 by causing the two supporting pars 576 to support the tubes 3, 7 in a straight taut state, operating the cylinder 512 to elevate the roller 502 and impart a tightly pressed state to the tubes 3, 7, and meanwhile operating the roller rotating means 501 to set the roller 501 rotating clockwise in the bearings of the diagram.

In the tube squeeze device 500a, the tubes 3, 7 are set so that the interval between the start position 532 for starting and the end position E for terminating the squeezing of the tubes 3, 7 will be embraced within the range in which the rollers 501 and 502 move their positions in consequence of the motion of the moving member 575. Thus, the tube squeeze device 500a may be so constructed that the distance between the two supporting parts 576 will be rendered adjustable and the range of the motion of the moving member 575 will be consequently rendered variable.

The tube squeeze device 500b illustrated in FIG. 31 is composed of the base 571, a lead screw 577 rotatably supported relative to the base 571, a motor 578 for rotating the lead screw 577, the slider 573 adapted to move on the lead screw 577 in the longitudinal direction in consequence of the rotation of the lead screw 577, the supporting members 574 erected severally in the opposite ends of the base 571, and the moving member 575 which comprises the same rollers 501 and 502 as mentioned above and the displacing means 510 for vertically reciprocating the roller 502. Now, the points in which the tube squeeze device 500b differs from the tube squeeze device 500a mentioned above will be described below, with the similar points omitted from the description.

The lead screw 577 is rotatably supported in place by a pair of bearings 579 and has a helical male thread formed on the peripheral surface thereof. Inside the slider 573, a female thread to be meshed with the male thread of the lead screw 577 is formed.

When the motor 578 disposed at one end of the lead screw 577 is operated to rotate the lead screw 577, the slider 573 moves on the lead screw 577 in the longitudinal direction thereof and the moving member 575 fixed to the slider 573 is moved in the lateral direction in the bearings of the diagram.

The moving member 575 is devoid of the roller rotating means 503. The rollers 501 and 502 used in the moving member 575, therefore, are both idle rollers (free rollers) capable of free rotation.

The drive timing, direction of rotation, speed of rotation, amount of rotation, duration of rotation, etc. of the motor 578 are similarly controlled by the control means 30.

In the present tube squeeze device 500b as in the counterpart mentioned above, the moving member 575 is moved in the right direction in the bearings of the diagram, the two rollers 501 and 502 are consequently rotated, and the tubes 3, 7 are squeezed by causing the supporting part 576 to support the tubes 3, 7 in a straight taut state, operating the cylinder 512 to elevate the roller 502 and impart a tightly pressed state to the tubes 3, 7, and meantime operating the motor 578 to set the lead screw 577 rotating in a prescribed direction.

The tube squeeze device 500b is devoid of the roller rotating means 503 for directly rotating the roller 501. Since the motion of the moving member 575 results in rotating the two rollers 501 and 502, a mechanism for moving the moving member 575, namely roller rotating means, is composed of the lead screw 577, the slider 573, and the motor 578.

The examples of the construction illustrated in FIG. 30 and FIG. 31 represent the cases of using the Container loading base 700 which is stationary and the tube squeeze part side rollers 501 and 502 which are movable. The construction is not limited to these cases. The construction, when necessary, may be such that the Container loading base 700 alone or the rollers 501 and 502 and the container loading base both will be rendered movable.

With the tube squeeze device contemplated by this invention, the work of discharging the gas or liquid from within the tubes into the container and the work of replacing the gas or liquid within the tubes with the liquid in the container can be carried out easily and quickly without entailing any manual process and the discharge or replacement of the liquid within the tubes can be carried out with high efficiency.

Particularly when the tube squeeze device is provided with stirring means for stirring the fluid in the container, the composition of the liquid placed in the tube in consequence of the replacement and that of the liquid held in the container can be homogenized.

[Tube sealing device 550]

Two tube sealing devices 550 are installed to serve each line of transfer of blood components as illustrated in FIG. 1. The tube sealing devices 550 are each endowed with the function of sealing the tubes 3, 7 by fusion and cutting the sealed parts of the tubes. They are each furnished with a pair of heating heads 551 and 552 and unshown head moving means adapted to move the two heating heads 551, 552 toward/away from each other.

The two heating heads 551, 552 are made of a metal such as, for example, brass, aluminum, or stainless steel and heated by an unshown heat source to a desired temperature enough for fusing the tubes. In this case, the heating heads 551, 552 may be provided with temperature control means (not shown) which is adapted to adjust the temperature thereof to a preset level.

A tube chucking surface 553 of the one heating head 551 has a flat shape as shown in FIG. 32. A tube chucking surface 554 of the other heating head 552 likewise has a flat shape. Near the center of this flat tube chucking surface 554, a protuberance 555 having a triangular cross section and extending in the radial direction of tube is formed.

The driving source for the head moving means, the heat source for the heating heads 551, 552, the temperature control means, and independent cutting means which will be specifically described hereinbelow are severally connected electrically to the hereinbelow specified control means 30. The control means 30 controls the drive of the relevant component parts just mentioned.

In the tube sealing device 550 constructed as described above, the tube 7 is inserted between the separated heating heads 551, 552, the heating heads 551, 552 are kept heated to a prescribed temperature and meanwhile moved toward each other to chuck the tube, and the heating head 551 and 552 are again moved away from each other after the elapse of a prescribed time. As a result, the tube 7 assumes such a shape as shown in FIG. 33. More specifically, the midway of the tube 7 is sealed by thermal fusion and the sealed portion 75 consequently formed in the tube is completely cut or cut to the extent of leaving behind a thin-wall connecting portion 76 by virtue of the protuberance 555. The thin-wall connecting portion 76 can be easily torn with only slight tensile force.

The tube sealing device 550 does not need to be limited to the illustrated construction. Optionally, protuberances 555 may be formed one each on both the heating heads 551, 552. The shape of the protuberance 555 is not specifically limited. For example, the cross section of the protuberance 555 may be a trapezoid, a circle, or an ellipse. The protuberance 555 may otherwise be formed of two stepped parts projected from the tube chucking surface to different heights and an inclined surface connecting the stepped parts.

This invention permits use of a tube sealing device so constructed that both the heating heads 551, 552 are devoid of the protuberance 555. Since the tube sealing device of this construction is not endowed with the function of cutting the sealed portion 75 of the tube, such cutting means (not shown) as a cutter is separately provided and used to cut and separate the sealed portion 75 of the tube.

Optionally, the tube sealing device may be so constructed that two portions of the tube will be sealed by fusion and the length of the tube intervening between the two sealed parts will be cut off by the aforementioned cutting means.

The tube sealing device to be used for this invention may be so constructed that the tube will be sealed by high-frequency fusion or ultrasonic fusion.

The tube sealing device and the cutting means constructed as described above may be selectively or not selectively provided to serve concurrently two lines or solely one line of transfer of blood components.

[Container feeding device 600]

Figure 34:
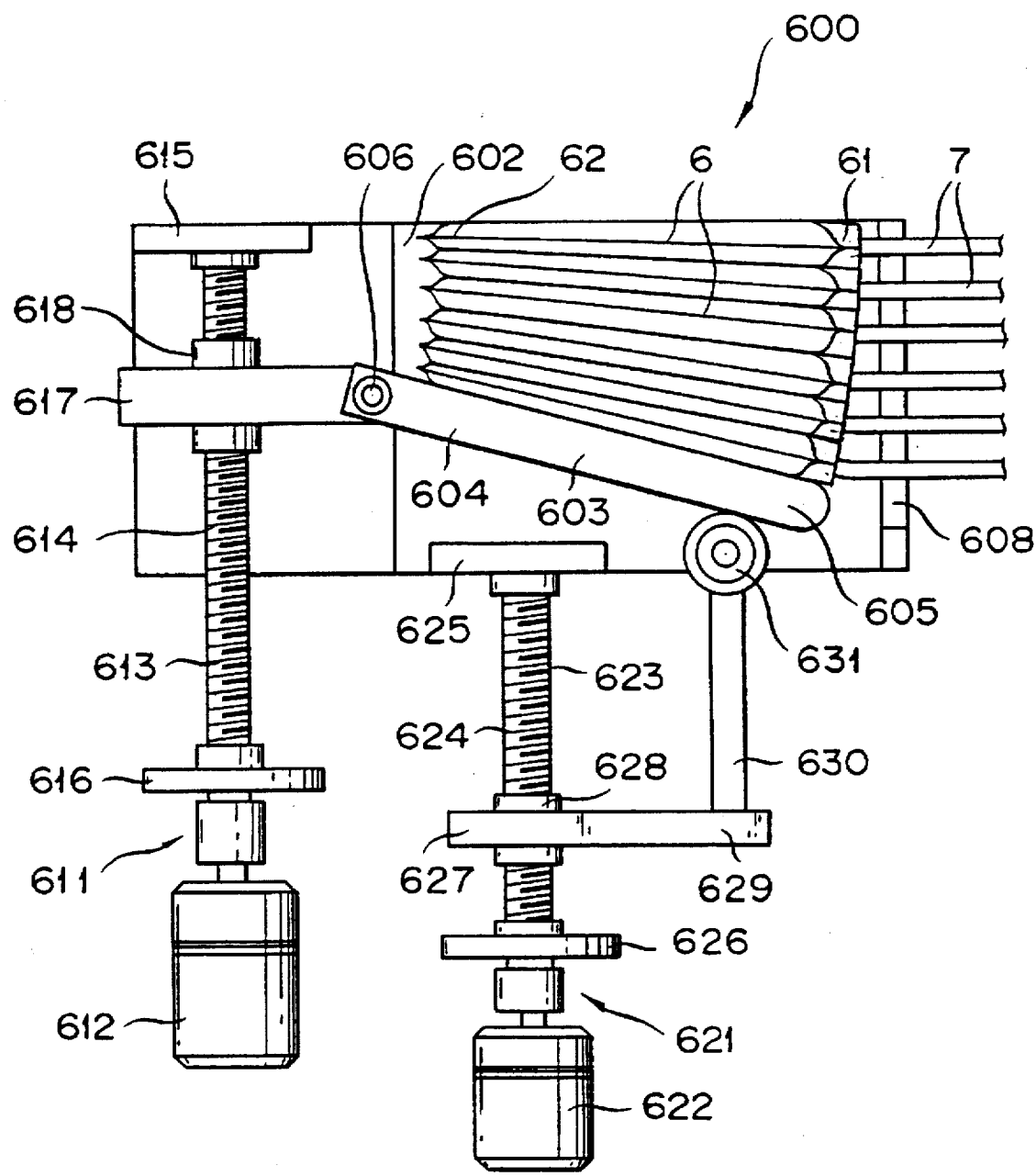
FIG. 34 is a front view illustrating a container feeding device.

The container feeding devices for supplying unused blood component bags 6 are disposed one each near the front and the rear surface of the other end side (the recessed side in the bearings for FIG. 1) of the apparatus 1 for manufacture of blood products. FIG. 34 is a partially sectioned side view illustrating one example of the construction of the container feeding device. The container feeding device 600, as shown in the diagram, is composed of a magazine 602 as a storing part for storing unused blood component bags 6, a loading board 603 disposed on the bottom part of the magazine 602 and holding the blood component bags 6, and a lift 610 for vertically reciprocating the loading board 603 within the magazine 602.

The magazine 602 is constructed of a box which is possessed of an empty space for accommodating a plurality of hereinbelow specified blood component bags with the tube 7 sides thereof directed in one same direction and is opened in the upper and the lower sides in the bearings of FIG. 34.

A ribbonlike opening (slit) 608 admitting the tubes 7 of blood component bags is formed in the vertical direction (the direction of Y) in the generally central part of the front surface (the right side in the bearings of FIG. 34) of this magazine 602. During the placement of the blood component bags 6 in the magazine 602, the arrangement of the blood component bags 6 inside the magazine 602 is facilitated by causing the tubes 7 of the blood component bags 6 to pass through the openings 608.

The blood component bags 6 to be accommodated in the magazine 602 are products which are obtained by superposing flexible resinous sheet materials and fusing (as by thermal fusion or high-frequency fusion) or adhesively joining matched peripheral parts of the superposed sheet materials.

To one end part (upper part) 61 of the blood component bag 6 is connected one end of the tube 7 which communicates with the interior of the bag. In this case, the connection of the tube 7 to the blood component bag 6 is effected by interposing the tube 7 closely between the superposed sheet materials in the peripheral part of bag and fusing (as by thermal fusion or high-frequency fusion) or adhesively joining the tacked portion of the tube with the bag.

In the blood component bag 6, the one end part 61 thereof has a thickness increased by a size equivalent to the external diameter of the tube 7 as compared with the other end part (the bottom part of bag) 62. The assembly of a plurality of blood component bags 6 accommodated in the magazine 602, therefore, produces a difference of thickness between the upper side of bag and the bottom side of bag as illustrated in the diagram in consequence of the accumulation of differences of thickness between the two end parts 61 and 62 of the individual blood component bags 6.

The largest number of blood component bags 6 that can be accommodated in the magazine 602 is not particularly limited. Generally, it is desired to set this number in the approximate range of 2 to 50, preferably 10 to 20.

In the proximity of the bottom part of the magazine 602, the loading board 603 adapted to support the blood component bags 6 is installed. The loading board 603 is a sheetlike (or frame-like) member and is rotatably fixed in a basal end part 604 thereof to a hereinbelow specified flexible member 617 through a pin 606.

In the illustrated construction, the individual blood component bags 6 are so superposed that the other end parts 62 of the blood component bags 6 will substantially coincide with the basal end part 604 of the loading board 603 and the one end parts 61 of the blood component bags 6 with the leading end part 605 of the loading board 603.

When one or more blood component bags 6 are superposed on the loading board 603 as illustrated in FIG. 34, since the thickness of the one end part 61 of each of the blood component bags 6 is larger than that of the other end part 62 thereof, the loading board 603 is inclined so that a leading end part 605 thereof will assume a lower position than the basal end part 604 thereof and consequently the uppermost of the blood component bags in the heap will remain in a horizontal position.

The loading board 603 is reciprocated in the direction of Y and revolved around the pin 606 by the lift (elevating device) 610. The lift 610 is provided with two driving mechanisms which are adapted to elevate the basal end part 604 and the leading end part 605 of the loading board 603 at different rates of speed. The driving mechanism 611 which elevates the basal end part 604 side of the loading board 603 is composed of a motor 612 as a driving source, a shaft 613 extended in the vertical direction and connected to the rotary shaft of the motor 612, supporting members 615 and 616 rotatably supporting the shaft 613 at the upper and the lower part thereof, and a movable member 617 adapted to move in the longitudinal direction of the shaft 613.

A screw thread 614 is formed on the periphery of the shaft 613 and a nut 618 adapted to be meshed with the screw thread 614 is fixed on the movable member 617. When the shaft 613 is rotated in a prescribed direction by the operation of the motor 612, the nut 618 ascends along the shaft 613 and consequently the movable member 617 ascends. When the shaft 613 is rotated in the direction opposite the direction mentioned above, the movable member 617 descends. The nut 618, when necessary, may be a ball screw which interposes balls (steel balls) between itself and the screw 614.

The driving mechanism 621 which elevates the leading end part 605 side of the loading board 603 is composed of a motor 622 as a driving source, a shaft 623 extended in the vertical direction and connected to the rotary shaft of the motor 622, supporting members 625 and 626 rotatably supporting the shaft 623 at the upper and the lower part thereof, a movable member 627 adapted to move in the longitudinal direction of the shaft 623, an arm 630 disposed on the movable member 617, and a roller 631 supported on the arm.

A screw thread 624 is formed on the periphery of the shaft 623 and a nut 628 like a ball screw adapted to be meshed with the screw thread 624 if fixed to the movable member 627. When the shaft 623 is rotated in a prescribed direction by the operation of the motor 622 in the same manner as described above, the nut 628 ascends along the shaft 623 and consequently the movable member 627 ascends. The movable member 627 descends when the shaft 623 is rotated in the direction opposite to the direction mentioned above.

The arm 630 is erected on an extended part 629 protruding sideways from the movable member 627 and the roller 631 capable of free rotation is disposed at the upper end of the arm 630. The peripheral surface of the roller 631 contacts the lower surface of the loading board 603 near the leading end part 605. In consequence of an ascent of the arm 630, the roller 631 pushes up the neighborhood of the leading end part 605 of the loading board 603 and, at the same time, rolls on the lower surface of the loading board 603.

The loading board 603 is supported in place by the pin 606 interconnecting the movable member 617 and the loading board 603, and the roller 631 disposed at the leading end of the arm 630. The loading board 603, therefore, is elevated in consequence of the ascent of the movable members 617 and 627. After the uppermost of the plurality of blood component bags superposed on the loading board 603 inside the magazine 602 is removed from the magazine 602, the loading board 603 will be elevated and the next blood component bag 6 will be consequently allowed to assume the same position (height) as the predecessor.

In this case, the driving mechanisms 611, 621 of the lift 610 elevate the movable members 617 and 627 at different rates of speed such that the basal end part 604 and the leading end part 605 of the loading board 603 will be raised at different rates of speed. This rate of speed is adjusted so that the uppermost of the plurality of blood component bags 6 accommodated in a pile inside the magazine 602 will always keep its posture in a fixed angle, specifically the angle of horizon in the illustrated construction, without reference to the number of the blood component bags 6 forming the pile.

Since the one end part 61 of each blood component bag 6 has a larger thickness than the other end part 62 thereof as already pointed out, the rate of elevation of the movable member 627 is set at a larger magnitude than that of the movable member 617 for the purpose of enabling the uppermost blood component bag 6 to remain in a horizontal position. Specifically, when the ratio of the thickness $T_1$ of the one end part 61 and the thickness $T_2$ of the other end part 62 of the blood component bag 6, $T_1:T_2$ is 3:2, for example, the rates of elevation of the movable members 627 and 617 are so adjusted that the ratio of the rate of elevation of the leading end part 605 to the rate of elevation of the basal end part 604 of the loading board 603 will be about 3:2.

Such rates of elevation of the movable members 617 and 627 as mentioned above are adjusted, for example, by controlling the speeds of rotation or the durations of operation of the motors 612 and 622 as desired, by setting the pitches of the screw threads 614 and 624 as desired, or suitably combining the two measures just described. The motors 612 and 622 are controlled by use of the control means 30 which will be specifically described hereinbelow.

When the rates of elevation of the movable members 617 and 627 are adjusted by setting the pitches of the screw threads 614 and 624, this adjustment obviates the necessity for assigning different controls severally to the motors 612 and 622 and brings about a desirable effect of simplifying the construction of the control system of the apparatus.

Owing to the construction described above, the blood component bags 6 accommodated in the magazine 602 and supplied therefrom sequentially from the uppermost blood component bag downward invariably assume a horizontal posture while removing from the magazine 602. The retention of the uppermost blood component bag 6 in the horizontal posture during the removal thereof from the magazine 602 can be facilitated and ensured by the second container conveying device 650 which will be specifically described hereinbelow. When this operation is repeated, it can be carried out uniformly and stably on each of the bags piled in the magazine 602.

After the magazine 602 is emptied of blood component bag 6, it will be prepared for the next cycle of operation by rotating the motors 612 and 10 in the direction opposite to the direction mentioned above, lowering the loading board 603 to the lowest allowable level, opening a lid 648 on the front surface of the apparatus for manufacture of blood products, and supplying the magazine 2 with a plurality of newly supplied blood component bags.

Figure 35:
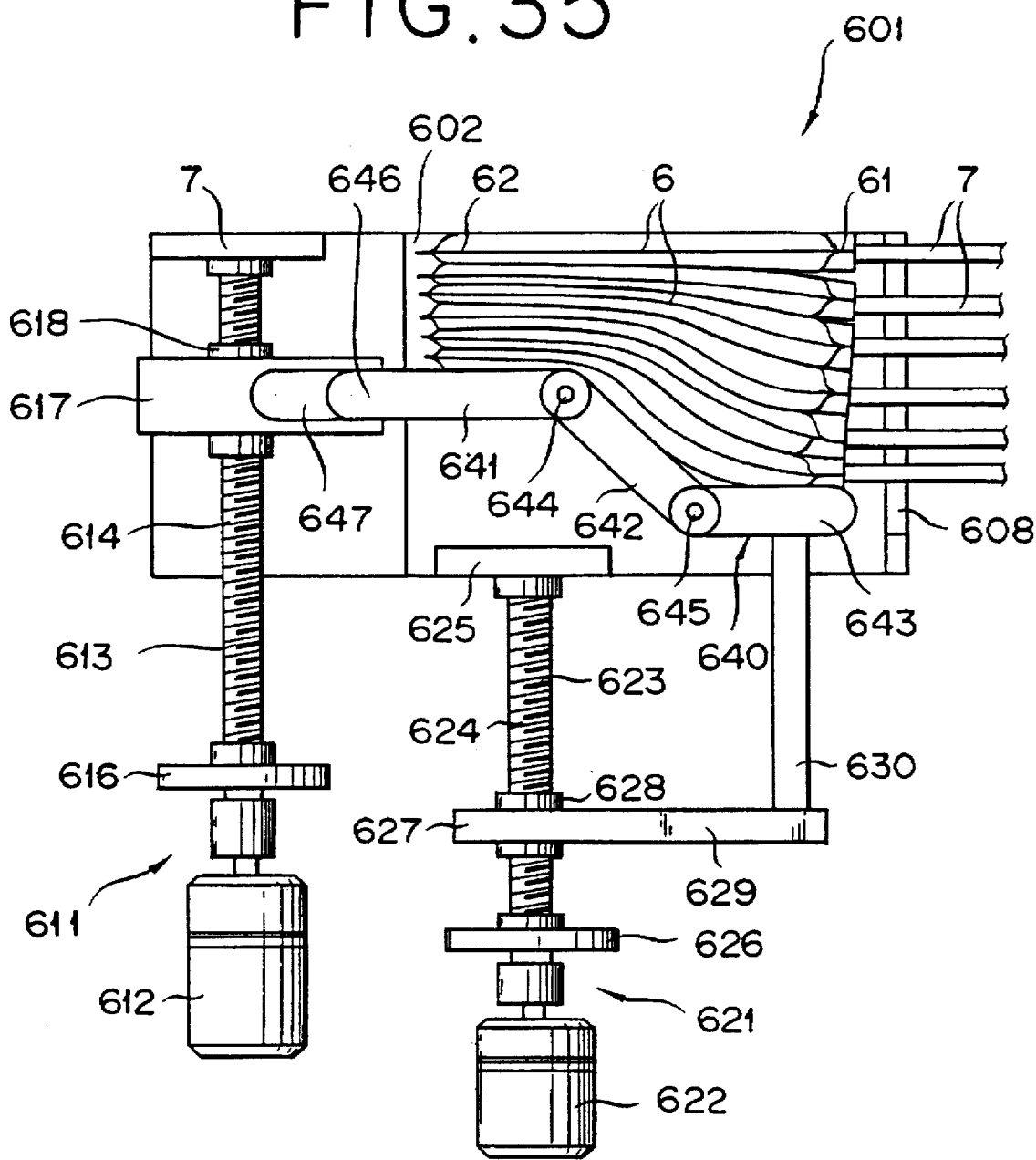
FIG. 35 is a front view illustrating another example of the container feeding device.

FIG. 35 is a partially sectioned side view illustrating another example of the construction of the container feeding device. A container feeding device 601 shown in the diagram differs from the container feeding device 600 described above mainly in the construction of the loading board and equals the countertype in the other constructions. Now, the different construction will be described below while the identical constructions will be omitted from the description.

A loading board 640 in the container feeding device 601 comprises three loading board segments 641, 642, and 643 which jointly form a link mechanism by having the loading board segments 641, 642 interconnected through a pin 644 and likewise having the loading board segments 642 and 643 interconnected through a pin 645.

The loading board segment 643 on the leading end side of the loading board 640 is fixed to the upper end of the arm 630 so as to assume a substantially horizontal posture and the loading board segment 641 on the basal end side of the loading board 640 is horizontally slidably supported in place with a basal end part 646 thereof inserted in a groove 647 formed on the lateral part of the movable member 617.

When one or more blood component bags 6 are superposed on the loading board 640 as shown in FIG. 35, since the one end part 61 of the blood component bag 6 has a larger thickness than the other end part 62 thereof, the loading board segment 643 is made to occupy a lower position than the segment 641 and the loading board segments 641 to 643 are collectively made to assume an overall shape bent like the letter S for the purpose of allowing the uppermost blood component bag 6 to remain in a horizontal posture.

The loading board 640 is supported in place by the groove 647 of the movable member 617 and the upper end of the arm 630. As a result, this loading board 640 ascends in consequence of the elevation of the movable members 617 and 14. After the uppermost of the plurality of blood component bags 6 superposed in a pile on the loading board 640 inside the magazine 602 is removed from the magazine 602, the next blood component bag 6 is caused to assume the same position (height) as occupied by the predecessor by elevating the loading board 640.

In this case, the loading board 640 deforms in consequence of the elevation of itself. Specifically, the loading board segments 641 and 643 ascend while keeping the horizontal postures thereof intact, the loading board segment 641 slides inside the groove 647 in consequence of the elevation of itself, and the central loading board segment 642 ascends while decreasing the angle of inclination thereof relative to the horizon.

The driving mechanisms 611, 621 of the lift 610 elevate the movable members 617 and 627 at different rates of speed so that the loading board segments 641 and 643 of the loading board 640 will be elevated at different rates of speed. The rates of elevation, like those mentioned above, are adjusted so that the uppermost blood component bag 6 will always keep the posture thereon at a fixed angle relative to the horizon, specifically a horizontal posture in the illustrated construction, without reference to the number of the blood component bags 6 which are accommodated in the magazine 602. The container feeding device 601 constructed as described above manifests the same effect as the countertype described above because the uppermost blood component bag 6 is always kept in a horizontal posture without reference to the number of the blood component bags which are accommodated in the magazine 602.

Further, the container feeding device 601 has advantages over the container feeding device 600 mentioned above as follows. For example, when the difference of thickness between the one end part 61 and the other end part 62 of the blood component bag 6 is relatively large or when the overall length of the blood component bag 6 is relatively large, the uppermost blood component bag 6 in the container feeding device 601 can be kept flat owing to the incorporation of the aforementioned link mechanism in the loading board 640 without reference to the conditions of the blood component bags 6 accommodated in the magazine as compared with the uppermost blood component bag 6 in the container feeding device 600 which is liable to form a recess near the central part thereof.

The lift is not limited to the construction which utilizes the driving mechanisms 611, 621 for independently elevating the opposite end parts of the loading board 603 or 640 as shown in the diagram. Optionally, the lift may be constructed so that mechanisms or devices will be used one each for elevating the opposite end parts of the loading board 603 or 640 at different rates of speed.

FIG. 1 depicts a construction using two container feeding devices 600. This construction is no critical requirement for this invention. Optionally, one container feeding device 600 may be so constructed that it will supply blood component bags 6 onto two loading boards 701.

[Second container conveying device 650]

The unused blood component bags 6 which have been supplied from the container feeding device 600 are conveyed one by one by the second container conveying device 650 to the Container loading base 700 which will be specifically described hereinbelow and mounted thereon. The blood component bags 6 to which blood components have been transferred are conveyed by the second container conveying device 650 from the container loading base 700 to the second container recovering case 710.

Figure 36:
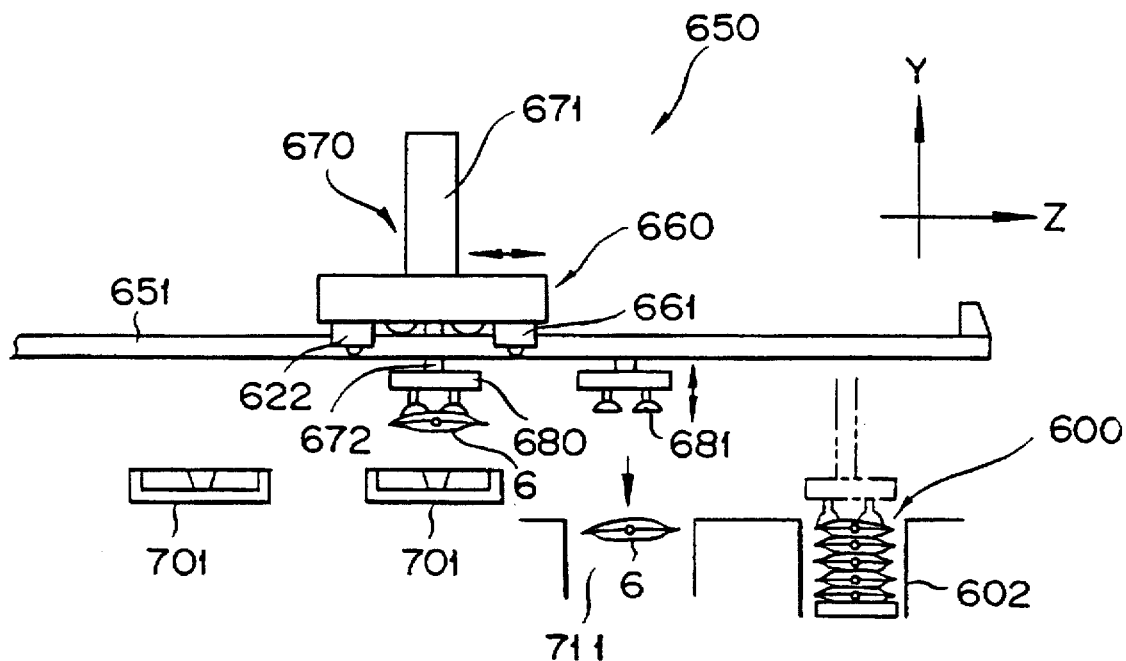
FIG. 36 is a side view illustrating a second container conveying device.
Figure 37:
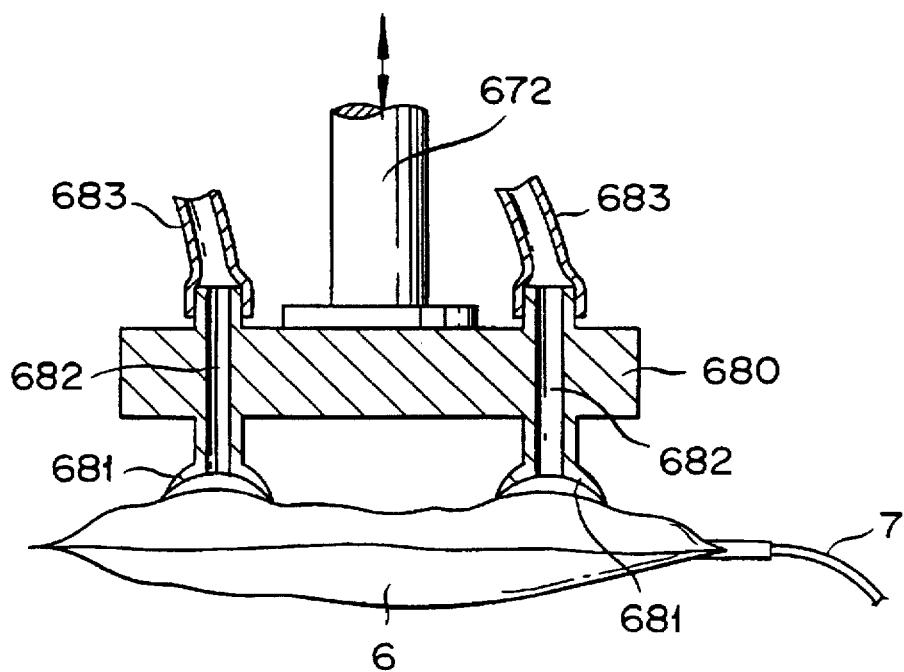
FIG. 37 is a sectioned front view illustrating the essential part of the second container conveying device on a magnified scale.

FIG. 36 and FIG. 37 are each a side view illustrating the second container conveying device 650. The second container conveying device 650, as shown in these diagrams, is provided with a conveying rail 651, a moving member 660, an elevating device 670, and a retaining member 680. The conveying rail 651 is erected in the direction of Z on the straight line interconnecting the container feeding device 600 (601), the container loading base 700, and a shooter 711 above the shooter, etc.

The moving member 660 is seated on the conveying rail 651 and adapted to reciprocate in the direction of Z on the conveying rail 651 within the range from the position above the one container feeding device 600 to the position above the other container feeding device 600.

The moving member 660 is provided with two pairs of rollers 661, 662 adapted to chuck the conveying rail 651 and a motor (not shown) for driving these rollers 661, 662. This motor is capable of normal/reverse rotation. When the rollers are rotated by the operation of the motor, the moving member 660 moves on the conveying rail 651 within the range mentioned above.

The elevating device 670 is composed of a pneumatically or hydraulically operated cylinder 671 disposed as on the moving member 660 and a piston rod 672. The retaining member 680 is fixed to the leading end of the piston rod 672. The operation of the cylinder 671, therefore, causes the piston rod 672 to move and the retaining member 680 to move in the direction of Y.

The retaining member 680, as shown in FIG. 37, is provided in the lower part thereof with four suction cups 681. Suction holes formed through the retaining member 680 communicate one each to the interiors of the suction cups 681. Suction tubes 683 are connected one each to the remaining ends of the suction holes 682. The suction tubes 683 are connected to such aspirating means (not shown) as a suction pump. Owing to the aspiration of air by the aspirating means, the retaining member 680 keeps the interiors of the suction cups 681 under a reduced pressure and retains the blood component bag 6 in place by aspiration.

The suction cups 681 are desired to be made of an elastic material such as, for example, rubber or a soft resin. The aspirating force generated by these suction cups 681 is set as such a level as to permit infallible retention of a blood component bag 6 containing blood components to full capacity. The suction cups 681 may be disposed on the main body of the retaining member 680 through such shock absorbing means (not shown) as a spring.

The motor for driving the rollers 661, 662, the elevating device 670, and the aspirating means are severally connected electrically to the hereinbelow specified control means 30, which controls the drive of the relevant component parts.

Now, the operation of the second container conveying device 650 constructed as described above will be explained below. For the placement of unused blood component bags 6 on the loading board 701, the moving member 660 is moved to set the retaining member 680 in place above the container feeding device 600 and then the elevating device 670 is operated to lower the retaining member 680 and bring the suction cups 681 into close contact with the surface of the uppermost unused blood component bag 6 inside the magazine 602 and the aspirating means is operated to make the suction cups 681 retain fast the blood component bag 6 by aspiration. Then, the elevating device 670 is operated to elevate the retaining member 680 and consequently lift one blood component bag 6 and, at the same time, the moving member 660 is moved until the blood component bag 6 retained thereby by aspiration is positioned above the Container loading base 700. Subsequently, by the operation of the elevating device 670, the retaining member 680 is lowered and the blood component bag 6 is set in place on the loading board 701. The aspiration exerted therefore by the aspirating means on the blood component bag 6 is now discontinued. As a result, the retention of the blood component bag 6 by the retaining member 680 ceases to exist. After the conveyance of the blood component bag 6 to the loading board 701 performed as described above is completed, the retaining member 680 is returned to the home position (reference position) by the operation of the elevating device 670 and the motion of the moving member 660.

For the conveyance to the second container recovering case 710 of a blood component bag 6 which has been sealed after completion of the transfer of blood components thereto, the moving member 660 is moved until the retaining member 680 is positioned above the loading board 701 supporting the blood component bag 6 thereon and then the elevating device 670 is operated to lower the retaining member 680 until the suction cups 681 comes into close contact with the surface of the blood component bag 6 and, at the same time, the aspirating means is operated to cause fast retention of the blood component bag 6 by aspiration. Then, the retaining member 680 is elevated and the blood component bag 6 is consequently lifted by the operation of the elevating device 670 and, at the same time, the blood component bag 6 now retained in place by aspiration is moved by the operation of the moving member 660 to a position above the selected shooter 711. Subsequently, the aspiration theretofore exerted by the aspirating means is discontinued, with the result that the retention of the blood component bag 6 by the retaining member 680 will cease to exist and the blood component bag 6 will fall into the shooter 711. After the recovery of the blood component bag 6 carried out as described above is completed, the retaining member 680 will be returned to the reference position by the operation of the elevating device 670 and the motion of the moving member 660.

The illustration portrays use of one second container conveying device 650 adapted for concurrently serving two lines of transfer of blood components from the viewpoint of simplifying the construction of the device. Optionally, the same second container conveying device 650 may be provided for each line of transfer of blood components.

This invention does not limit the second container conveying device 650 to the function of simultaneously keeping hold of the blood component bag 6 by aspiration and conveying it. This device may be otherwise constructed so as to utilize separately a chucking member for keeping the blood component bag 6 chucked fast, a hook for keeping the blood component bag 6 suspended, or a moving base or a conveyer for keeping the blood component bag 6 mounted, for example, during the conveyance.

[Container loading base 700]

Figure 39:
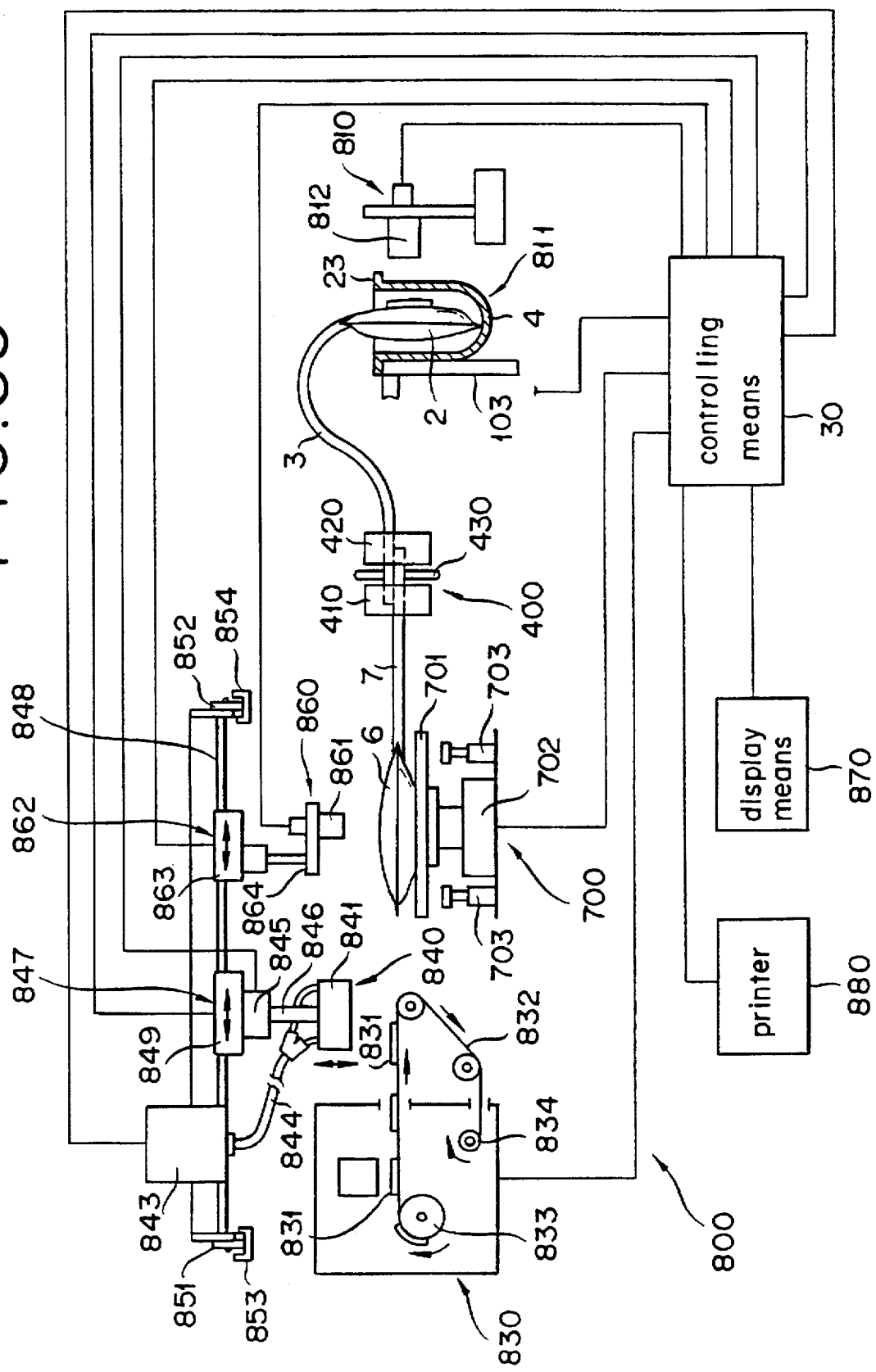
FIG. 39 is a structural diagram illustrating in the form of a model an data processing device.

On the other end side (the recessed part side in the bearings of FIG. 1) of the apparatus 1 for manufacture of blood products, two container loading bases 700 for supporting blood component bags 6 during the transfer of blood components are installed. The container loading bases 700, as shown in FIG. 39, are each composed of a loading board 701 for seating a blood component bag 6, a load cell (weight detecting means) 702 for detecting the weight of the blood component bag 6 on the seating device 701, and stoppers (overload releasing means) 703 disposed one each on both lateral parts of the load cell 702 and adapted to regulate the lowest allowable position of the loading board 701.

When a label 831 is pasted to the blood component bag 6 on the loading board 701 as will be specifically described hereinbelow, a head 841 of a label application device 840 which will be specifically described hereinbelow presses the blood component bag 6. In this case, the exertion of a load exceeding the allowable limit on the load cell 702 is precluded because the loading board 701 after descending to a certain extent and colliding against the stopper 703 is prevented from continuing the descent any further.

The leading end part of the stopper 703 is adapted to be moved in the vertical direction and, therefore, is enabled to adjust the lowest allowable position of the loading board 701. Optionally, the stopper 703 may be adapted to ascend to the extend of fixing the loading board 701 in place and preventing it from exerting a load on the load cell 702.

The load cell 702 is electrically connected to the control means 30 so that the information on weight detected by the road cell 702 will be input into the control means 30 to be processed thereby as desired. When the cumulative weight of blood components transferred to the blood component bag 6 reaches a fixed level, the control means 30 effects a control to stop the transfer of blood components.

When the total weight of blood components transferred to a given blood component bag 6 happens to be short, this blood component bag 6 is discarded as a rejectable (defective) blood product which will be specifically described hereinbelow. The control means 30 decides the rating of this rejectability and controls the operation of the second container conveying device 650 so as to discriminate the particular blood component bag 6 rated as a rejectable blood product from other acceptable blood products as by causing the bag 6 to be dumped into the shooter 711 set aside for disposal of useless articles, for example.

Figure 40:
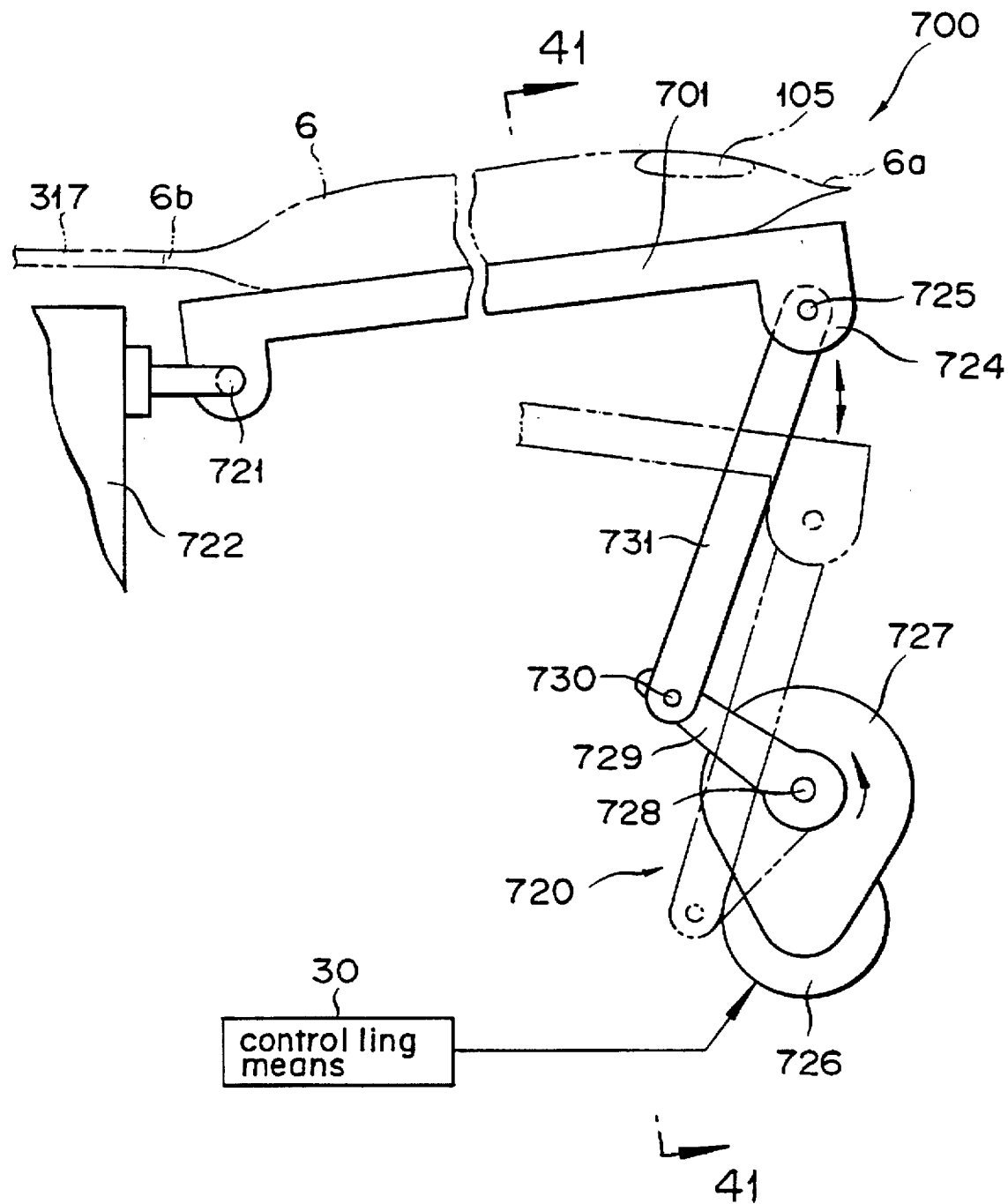
FIG. 40 is a side view illustrating stirring means in the tube squeeze device.
Figure 41:
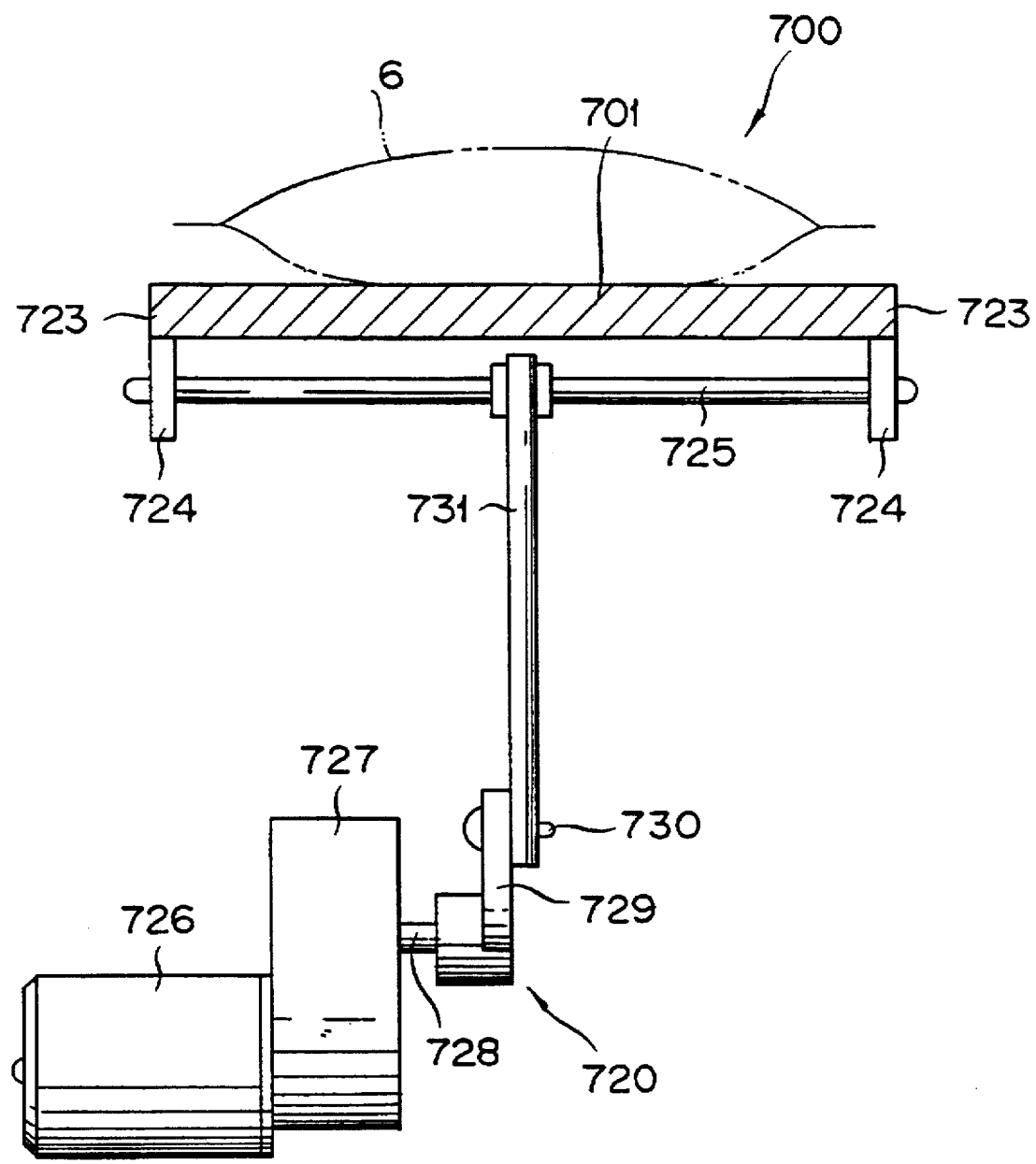
FIG. 41 is a view taken through FIG. 40 along the line 41—41 and viewed in the direction of the arrow.

FIG. 40 is a side view illustrating a modified example of the container loading base which is provided with stirring means 720 and FIG. 41 is a cross section taken through FIG. 40 along the line 41—41. The container loading base 700, as shown in these diagrams, is provided with the loading board 701 for supporting such a container as a flexible bag 6 and bag shaking means 720 which is stirring means for stirring a fluid in the bag 6 supported on the loading board 701.

The loading board 701 is a member shaped like a plate or a frame. The leading end (the left end in the bearing of FIG. 40) of the loading board 701 is revolvably attached to a base 722 of the Container loading base 700 through a shaft 721. A pair of supporting pieces 724 projecting toward the reverse surface side (the lower side in the bearings of FIG. 40) of the loading board 701 are formed in the opposite lateral parts 723 of the rear end (the right end in the bearings of FIG. 40) of the loading board 701. A shaft 725 is laid to interconnect the opposite supporting pieces 724.

On the obverse surface (the upper surface in the bearings of FIG. 40) side of the loading board 701, a fixing member for fixing the leading end part 6b or the trailing end part 6a, for example, of the bag 6 to the loading board 701 is disposed, through not shown in the diagram.

The shaking means 720 is installed on the reverse surface side of the loading board 701. It is composed of a motor 726 resembling the motor mentioned above and serving as a driving source, a gearbox 727 for reducing the speed of rotation of the motor 726, an arm 729 having one end thereof fixed to an output shaft 728 of the gearbox 727, and an arm 731 having one end thereof revolvably connected through a pin 730 to the other end of the arm 729 and having the aforementioned shaft 725 inserted through the other end thereof. The arms 729 and 731 and the pin 730 interconnecting the arms jointly form a crank mechanism.

In the shaking means 720 which is constructed as described above, when the motor 726 is actuated, the rotating consequently produced is reduced by the gearbox 727 and transmitted to the output shaft 728 and used for rotating the arm 729 in a prescribed direction. As a result, one end of the arm 731 is moved along the locus of the other end of the arm 729 in rotation and, in consequence of this motion, the other end of the arm 731, the shaft 725 connected thereto, and the supporting piece 724 are shaken and the loading board 701 is revolved (shaken) in the vertical direction in the bearings of FIG. 40 around the axis 721 as the center. In consequence of this revolution of the loading board 701, the bag 6 supported on the loading board 701 is shaken and the liquid and gas in the bag 6 are stirred.

When the liquids [such as, for example, blood (red blood cells, white blood cells, blood plasma, platelets), and chemical solution] discharged from the tubes 3, 7 are different in composition from the liquids [such as, for example, chemical solutions (anticoagulant, red blood preserver, platelet preserver, and reagent)] packed in the bag 6, these liquids are uniformly mixed by stirring.

The shaking of the bag 6 which is attained as described above is continued for a duration preset by a timer which is built in the control means 30. The motor 726 is stopped after the preset time expires.

Figure 42:
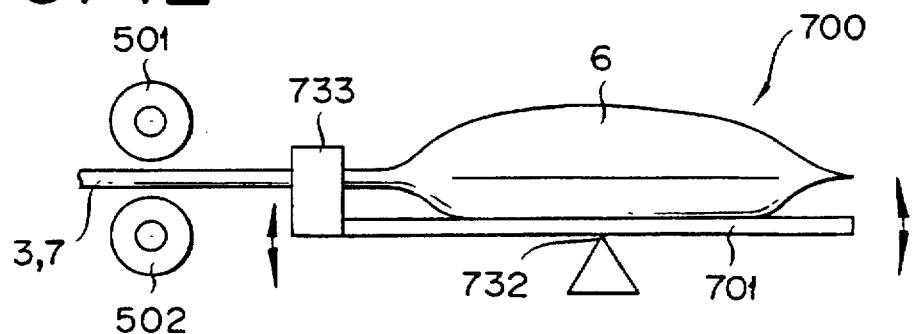
FIGS. 42 and 43 are side views each illustrating a container loading device in the tube squeeze device.

FIG. 42 is a side view illustrating another example of the container loading base. The Container loading base 700, as shown in the diagram, is provided with the same shaking means (not shown) as described above. A fulcrum 732 to be used by the shaking means in revolving the loading board 701 is located near the center of the loading board 701 in the longitudinal direction of the bag so that the leading end and the trailing end of the loading board 701 will be severally reciprocated in the vertical direction.

In order for the construction described above to impart required shaking to the bag 6 on the loading board 701, a cramp means 733 disposed at the leading end (the left end in the bearings of FIG. 42) of the loading board 701 is actuated to press and close the tubes 3, 7 and block the inner cavities thereof and, at the same time, the rollers 501 and 502 are released from the state of chucking the tubes 3, 7 so as to allow free motion of the tubes 3, 7 between the rollers 501 and 502.

Figure 43:
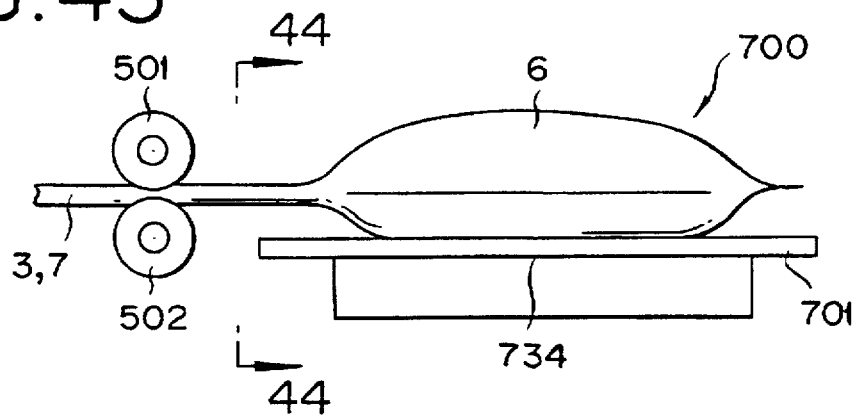
Figure 44:
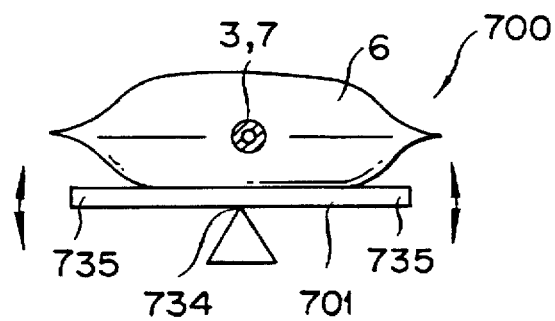
FIG. 44 is a view taken through FIG. 3 along the line 44—44 and viewed in the direction of the arrow.

FIG. 43 is a side view illustrating yet another example of the container loading base and FIG. 44 is a cross section taken through FIG. 43 along the line 44—44. The Container loading base 700, as illustrated in these diagrams, is provided with the same shaking means (not shown) as described above. A fulcrum 734 to be used by this shaking means in revolving the loading board 701 is located near the center of the loading board 701 in the direction of width of the bag so that opposite lateral parts 735 of the loading board 701 will be severally reciprocated in the vertical direction.

In the Container loading base 700 of this construction, the tubes 3, 7 can be shaken around the bag 6 on the loading board 701 as the center and the tubes 3, 7 are meantime kept in a pressed and closed state by the rollers 501 and 502.

Figure 45:
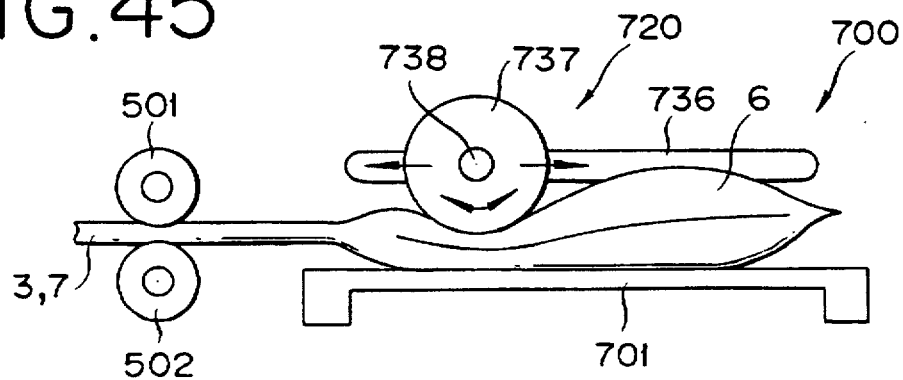
FIG. 45 is a side view illustrating a container loading device in tube squeeze device.

FIG. 45 is a side view illustrating still another example of the container loading base. The Container loading base 700, as shown in the diagram, is provided with stirring means 720. This stirring means 720 is intended to stir the fluid in the bag 6 without shaking the loading board 701. It is composed of a guide 736 extended substantially parallel to the loading board 701, a roller 737 adapted to move along this guide 736, and moving means (not shown) capable of moving the roller 737.

The guide 736 may be constructed, for example, in the form of an oblong hole adapted to admit a shaft 738 of the roller 737 or a member with a rack gear to be meshed with a pinion gear (both gears not shown) which is to be fixed on the shaft 738 of the roller 737.

The roller 737 is disposed at a position separated by a prescribed distance from the obverse surface (the upper surface in the bearings of the diagram) of the loading board 701. This position of the roller 737 is such that the outer surface thereof will be enabled to exert moderate pressure on the bag 6 filled with the liquid.

In the stirring means 720 constructed as described above, when the moving means mentioned above is operated to move the roller 737 along the guide 736, this motion of the roller 737 causes a change in the position of pressure exertion on the bag 6 and consequently deforms the bag 6 and stirs the fluid in the bag.

In this invention, the stirring means which is installed in the container loading base does not need to be limited to any of the constructions illustrated in the diagrams mentioned above. It may be, for example, a vibrator capable of imparting oscillation to the bag 6 or such a stirring device as a magnet stirrer. This invention also allows the container loading base to be dispossessed of the shaking means or other stirring means.

[Second container recovering case 710]

Within the range in which the second container conveying device 650 effects required conveyance, the second container recovering cases 710 for recovering the blood component bags 6 to which blood components have been transferred are disposed one each in the positions adjoining the two container loading base 700 as illustrated in FIG. 1. The second container recovering case 710 is provided with the shooter 711. In this case, the shooter 711 is positioned between the loading board 701 of the container loading base 700 and the magazine 602 of the container feeding device 600. The two container loading bases 7, the two shooters 711, and the two magazines 602 are disposed in a substantially rectilinear pattern.

The blood component bag 6 which has been placed on the loading board 701, filled with blood components, and sealed tightly is picked up by the suction cups 681 of the second container conveying device 650 by virtue of aspiration, conveyed to a position above the shooter 711 adjoining the loading board 701, for example, and dropped from the suction cups 681 into the shooter 711 by cancellation of the aspiration (see; FIG. 36). The blood component bags 6 which have been recovered and piled up in the shooter 711 are removed through an outlet (not shown) formed in the lateral wall of the apparatus 1 for manufacture of blood products.

The two shooters 711 are desired to be used as discriminated with respect to varying items of blood products (such as, for example, blood plasma and buffy coat, buffy coat and other item, platelet and other item). This discrimination does not form any critical requirement for this invention. The two shooters 711 may be used severally to serve each line of transfer of blood components. Otherwise, one of the two shooters 711 may be used for recovery of blood products which meet the standard and the other for recovery of blood products which do not meet the standard (by reason of shortage of weight, unduly low ratio of removal of extraneous blood components) and must be discarded as useless. The number of shooters 711 is not particularly limited. It may be 3 or even more.

[Chemical solution supplying device 750]

The chemical solution supplying devices 750 for supplying chemical solutions to the blood bags 2 are installed one each on the front side and the rear side of the apparatus 1 for the manufacture of blood products. FIG. 38 is a model diagram illustrating the construction of a circuit for the chemical solution feeding device 750. The chemical solution feeding device 750, as shown in the diagram, comprises a chemical solution container 751, a third tube 752 communicating with the interior of the chemical solution container 751, and a stand 753.

The chemical solution container 751 is retained in place desirably detachably by the stand 753. The chemical solution container stores a chemical solution. When the transfer of blood plasma and buffy coat to the blood component bag 6 is completed and a red blood cell preserving liquid is to be added by use of the chemical solution feeding device 750 to the concentrated red blood cells remaining in the blood bag 2, for example, the red blood cell preserving liquid 760 is stored in the chemical solution container 751. Incidentally the chemical solution container 751 may be made of a flexible material or a rigid material.

The capacity of the chemical solution container 751 is not particularly limited. To satisfy amply the requirement for automation of the addition of chemical solution, however, this capacity is desired to be such that the chemical solution container 751 can continuously supply the red blood cell preserving liquid to a plurality (approximately 2 to 100) of blood bags 2.

Specifically, the capacity in question is in the approximate range of 100 to 10,000 ml, preferably 1,000 to 5,000 ml.

As concrete examples of the red blood cell preserving liquid 760 to be used in the chemical solution container 751, the following aqueous solutions may be cited.

(1) An aqueous solution called S.A.G.M. solution (containing 0.877% of sodium chloride, 0.0169% of adenine, 0.818% of grape sugar, and 0.525% of D-mannitol).

(2) An aqueous solution produced by Thermo Co., Ltd., marketed under trademark designation of "OPTISOL," containing 0.877% of sodium chloride, 0.030% of adenine, 0.818% of grape sugar, and 0.525% of D-mannitol.

(3) An aqueous solution called MAP solution containing 0.497% of sodium chloride, 0.014% of adenine, 0.721% of grape sugar, 1.457% of D-mannitol, 0.020% of citric acid, 0.150% of sodium citrate, and 0.094% of monosodium phosphate.

To the lower end of the chemical solution container 751 is connected one end of the tube 752 which communicates with the interior of the chemical solution container 751 as shown in FIG. 38. The other end of this tube 752 is conveyed by the tube conveying device 300, loaded in the tube connecting device 400 by the tube loading device 350, and connected to the tube 3 of the blood bag 2. Then, by the operation of the roller pump 160 set in the midway of the tube 3, the red blood cell preserving liquid 760 in the chemical solution container 751 is supplied into the blood bag 2 through the interconnected tubes 752 and 3.

Owing to the use of the roller pump 160 for the transfer of the red blood cell preserving liquid 760, the present example enables this transfer to proceed quickly and infallibly at a stable flow volume. Besides, it obviates the necessity for installing the chemical solution container 751 at an elevated place and permits great freedom in the design of the layout and construction of the chemical solution container 751 and associated component parts and contributes to the miniaturization of the apparatus 1 for the manufacture of blood products. Further, the roller pump 160 has an advantage over the pumps of the other types in permitting easy attachment and detachment of itself without interfering with the closed system of flow path. Thus, it proves beneficial for the sake of aseptic processing in the manufacture of blood products.

A valve, a cock, or a flow regulating valve, though not illustrated in the diagram, may be provided in the midway of the tube 752, particularly near the chemical solution container 751.

The proper amount of the red blood cell preserving liquid 760 to be fed is substantially proportional to the amount of red blood cells held in the blood bag 2. The chemical solution feeding device 750 of the present example is provided with flow detecting means 170 capable of detecting the amount of the chemical solution which flows in the blood bag 2 and, therefore, is enabled to control the actual amount of the red blood cell preserving liquid 760 added to the blood bag 2 based on the information to be obtained by the flow detecting means 170. As concrete examples of the flow detecting means, a flow meter (integrating flow meter) disposed in the midway of the tube 752 or means for detecting the operating time or revolution number of the roller pump 160 may be cited.

Alternatively, the control of the amount of the red blood cell preserving liquid 760 to be added may be accomplished by installing a load cell (not shown) as a weight sensor for detecting the weight of the blood bag 2 in the lower part of the bag pressing device 151, operating this load cell to detect the weight of the content of the blood bag 2, and using the result of this detection as the basis for the control of the amount of the preserving liquid 760 to be added. For example, this control is attained by causing the load cell to detect the weight of the concentrated red blood cells in the blood bag 2 prior to the addition of the red blood cell preserving liquid 760 and, based on the change of weight of the load cell, adjusting the amount of the red blood cell preserving liquid 760 to be fed to a value proportionate to the weight so detected. In this case, since the red blood cell preserving liquid 760 can be added in a proper amount conforming to the amount of the concentrated red blood cells in the blood bag 2, the red blood cells will be preserved in the blood bag 2 under the optimum conditions and will consequently enjoy a long shelf life.

As concrete ways of adjusting the amount of the chemical solution based on the information acquired by the flow detecting means, a method which effects this adjustment by controlling the operating time or the revolution number of the roller pump 160 and a method which adjusts the flow volume of the red blood cell preserving liquid 760 supplied to the blood bag 2 by use of a flow regulating valve (not shown) provided in the midway of the tube 752 may be cited.

The chemical solution feeding device 750, when necessary, may be so constructed that the red blood cell preserving liquid 760 will be added in a predetermined amount to the blood bag 2 besides being so constructed that the amount of the red blood cell preserving liquid 760 will be adjusted proportionately to the amount of the concentrated red blood cells in the blood bag 2.

The roller pump 160 mentioned above may be substituted by such a regular grade pump as a centrifugal pump or a bellows type pump. The supply of the red blood cell preserving liquid 760 to the blood bag 2 may be alternatively effected by setting the chemical solution container 751 at a higher place than the blood bag 2 and inducing the flow of the preserving liquid 760 to the blood bag 2 spontaneously by virtue of water level instead of using any of the pumps mentioned above.

In the construction illustrated in FIG. 1, chemical solution supplying devices 750 are provided one each for the two lines of transfer of blood components. Optionally, one chemical solution supplying device 750 may be used for concurrently serving the two lines of transfer of blood components.

The construction intended to add the red blood cell preserving liquid 760 to the blood bag 2 already holding the concentrated red blood cells has been typically described heretofore. This particular construction does not form any critical requirement for this invention. In the case of a blood bag 8 which is provided with a partition portion as specifically described hereinbelow or a blood bag which is so constructed as to have tubes connected one each to the upper and the lower end of bag (JP-B-63-20,144), the platelet preserving liquid can be added thereto by use of the chemical solution feeding device 750 because, of the three centrifugally separated blood components, the blood plasma and the red blood cells are discharged respectively through the upper and the lower part of bag and the buffy coat are finally left standing in the blood bag.

It is permissible to feed the platelet preserving liquid by use of the chemical solution feeding device 750 to the blood component bag 6 which has received either the buffy coat or the concentrated platelets.

In the apparatus 1 for manufacture of blood products, the addition of chemical solutions of different kinds such as, for example, the red blood cell preserving liquid and the platelet preserving liquid, to different bags may be effected, for example, by preparing chemical solution containers 751 containing such chemical solutions and suitably interchanging them during the course of actual use or by preparing a plurality of chemical solution containers 751 and switching the flow paths for transfer of these chemical solutions discharged from the containers 751. In the latter case, a flow channel provided with flow path switching means which is constructed by joining individual tubes 752 severally emanating from a plurality of chemical solution containers 751 into one tube (to be eventually connected to the tube 3, for example) through a branched connector and therefore operated by selectively pressing and closing the individual tubes 752 and blocking the inner flow paths thereof may be used.

[Data processing device 800]

FIG. 39 is a structural diagram illustrating the data processing device 800 in the form of a model. The data processing device 800, as shown in the diagram, comprises a reader 810 for reading a data code tacked to the blood bag 2 at an information reading unit 811, a label producing device 830 for forming the data code on a label, a label application device 840 for applying a label 831 produced by the label producing device 830 to the blood component bag 6, a check reader 860 for reading and confirming the data code on the label 831 applied to the blood component bag 6, display means 870, and a printer 880. Now, these component elements of the data processing device 800 will be described sequentially below.

Figure 47:
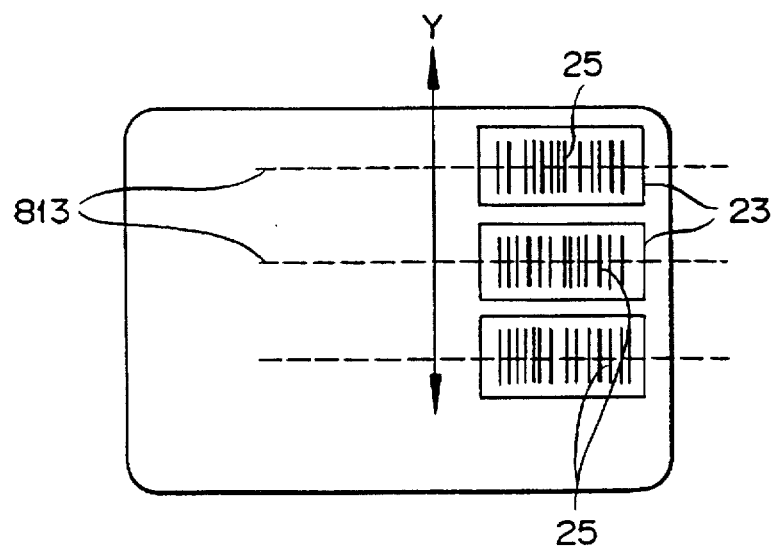
FIG. 47 is a diagram illustrating one example of the disposition of a label applied to a bag.

To the outer surface on one side of the blood bag 2, at least one label 23 with a bar code (data code) 25 (see; FIG. 47) having the information concerning the blood to be collected in the blood bag 2 is applied directly or through a large bag label. Optionally, one or more bar codes 25 may be directly printed on the bag label.

As concrete examples of the information to be indicated by the bar code 25, name of blood product, code number, production number of blood product, blood type (ABO, Rh blood group system), items of biochemical test (such as, for example, GOT, GPT, TA, Alb, and total bilirubin), presence or absence of infectious disease, date of blood collection, place of blood collection (such as, for example, code of medical facilities), and information on donor (such as, for example, address, name, sex, age, data of birth, body weight) may be cited. Of these pieces of information, those which are pertinent to occasion are carried.

The blood bag 2 now bearing the label 23 is conveyed by the conveying device described above to the information reading unit 811.

(A) Reader 810 the reader 810, as shown in FIG. 1, is disposed on the rear surface side in the central part of the apparatus 1 for manufacture of blood products. It comprises a bar code reader 812, moving means (actuator) 814 for moving the bar code reader 812 in the direction of Y (the vertical direction) in the bearings of FIG. 1, and reading auxiliary means 819. These component parts are mounted on a moving base 822 which is movable in the direction of X.

Figure 46:
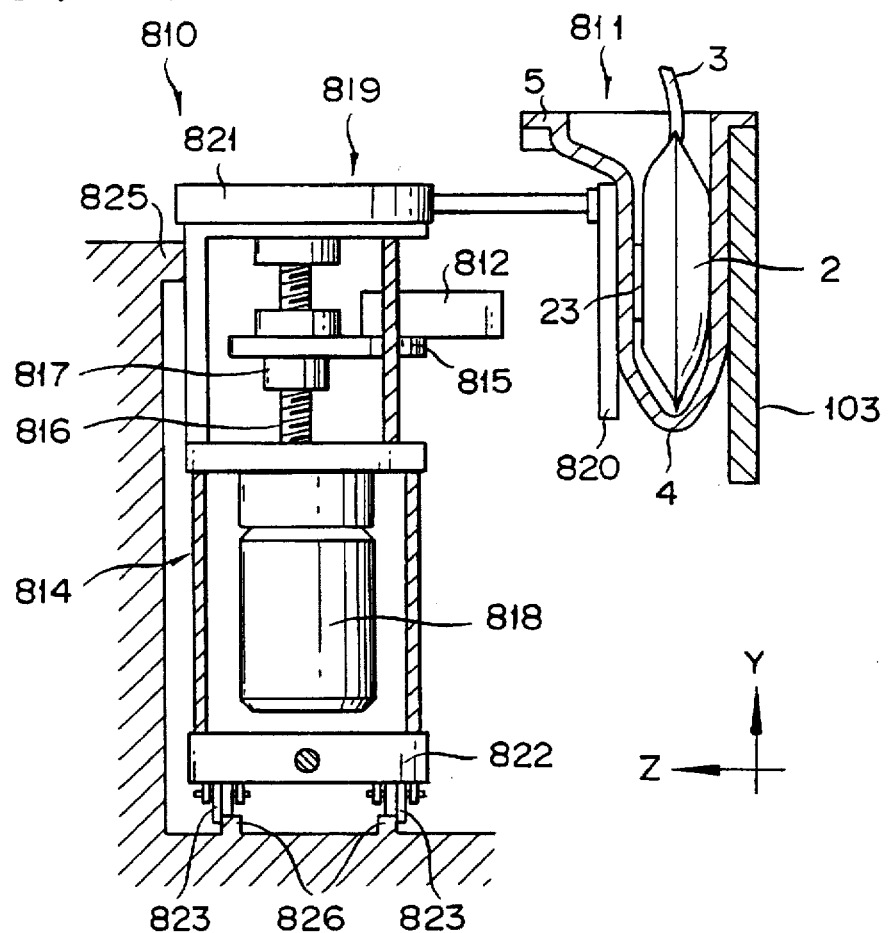
FIG. 46 is a partially sectioned side view illustrating a reader.

The moving means 814, as shown in FIG. 46, is composed of a moving base 815 for fixing the bar code reader 812, a screw shaft 816 having a helical screw thread formed thereon, a nut 817 fixed to the moving base 815, and a driving source 818 for rotationally driving the screw shaft 816. A motor capable of normal/reverse rotation, for example, is used as the driving source 818. When this driving source 818 is operated, the screw shaft 816 is rotated and consequently the nut 817 is moved in the direction of Y and the bar code reader 812 is selectively reciprocated in the vertical direction.

This vertical reciprocation of the bar code reader 812 is carried out for the purpose of aligning the scanning line of the bar code reader 812 and the position of the label 23 on the blood bag 2 and, in the case of the blood bag 2 having a plurality of bar codes 25 printed in a layout shown in FIG. 47, for the purpose of sequentially aligning these bar codes 25 and the scanning line 813 on the bar code reader 812 and reading these codes.

Incidentally, the bar code reader 812 is only required to be capable of reading bar codes. As concrete examples of the bar code reader 812, a reader of the laser scan system and a reader of the line sensor type may be cited.

The reading auxiliary means 819 is composed of a transparent (flat) plate 820 and driving means 821 capable of moving the transparent plate 820 at a relatively low speed toward the cup 4 retained by the cup retaining member 103. Specifically, the driving means 821 may be a solenoid, a cylinder (of hydraulic or pneumatic operation), or means similar to the moving means 814 mentioned above, for example.

When the driving means 821 is actuated, it slowly moves toward the right in the bearings of FIG. 46 and presses the cup 4 and the blood bag 2 held therein and causes the part of the blood bag 2 having the label 23 pasted thereto to contact the transparent plate 820 tightly through the lateral wall of the cup 4. In the ensuant environment, the bar code reader 812 reads the bar code 25 on the label 23 through the transparent plate 820 and the lateral walls of the cup 4. The accuracy with which the bar code reader 812 reads the bar code 25 is exalted in this case by the fact that the label 23 is pressed tightly on the inner surface of the lateral wall of the cup 4 and consequently kept in a flat state. The exertion of pressure by the transparent plate 820 on the blood bag 2 in this case is desired to proceed slowly and gradually so that the boundaries of the separated blood components in the blood bag 2 will not be disturbed.

Incidentally, the reaction of the pressure exerted by the transparent plate 820 on the blood bag 2 is absorbed by the fact that the rear surface of the reader 810 contacts a projecting part 825 of the wall of the apparatus' main body 15 to which the rear surface is opposed. Thus, the reader 810 is allowed to keep the posture thereof intact.

The bar code reader 812 is electrically connected to the control means 30. The information read out by the bar code reader 812, therefore, is injected into the control means 30 and processed therein as desired.

Four wheels 823 are set in place beneath a moving base 822. When these wheels 823 roll on rails 826 formed on the main body 15 of the apparatus, the reader 810 is reciprocated in the direction of X. As a result, the labels 23 of the two blood bags 2 retained by the cup retaining member 103 are sequentially read out.

(B) Label producing device 830

The label producing device (printer) 830 is electrically connected to the control means 30. In response to a signal from the control means 30, it forms (by printing or thermal ink transfer) on the label 831 a bar code (and an indication of character, sign, color, etc.) which corresponds to the information carried by the bar code 25 on the label 23 of the blood bag 2 and other added information. The added information includes date and time of manufacture of blood product, weight of blood components held in the blood component bag 6, kind and quality of bag, manufacturer of bag, and production lot number of bag, for example. Of these various data items of information, the date and time of manufacture of blood product are obtained from a clock which is built in the control means 30, the weight of blood component is derived from the magnitude detected by the load cell 702 mentioned above, and the attributes of the bag are introduced by such external input means as a keyboard connected to the operator console 40, for example.

Inside the label producing device 830, a roll 833 of a ribbonlike label sheet 832 having unused labels 831 arranged as spaced with a fixed interval and a reel 834 for rewinding the label sheet 832 are set in place as shown in FIG. 39. The label sheet 832 is paid out of the roll 833 in consequence of the rotation of the rewinding reel 834 and, synchronously with the motion of the label sheet 832, bar codes are sequentially printed on the successive labels 831 on the label sheet 832. The labels 831 on which relevant bar codes have been printed are conveyed out of the label producing device 830 in consequence of the motion of the label sheet 832.

The label 831 to be used in the label producing device 830 has the reverse surface thereof coated with an adhesive mass or a hotmelt type adhesive agent, for example.

The label producing device 830 may be capable of displaying, in the place of or in addition to the bar code, a data code of other kind such as, for example, monochromic or color characters, signs, or figures. Specifically, the label producing device 830 may be so constructed as to permit use of labels prepared in different colors (four colors, for example) or implement color printing and, therefore, produce labels 831 in varying colors indicative of blood types, for example.

The label 831 which has been produced by the label producing device 830 of the construction described above is conveyed to the outer surface of the blood component bag 6 and tacked thereto by the label application device 840.

(C) Label application device 840

The label application device 840 is composed of a head 841, suction means 843 for tacking the label 831 by suction to the head 841, driving means 845 for moving the head 841 in the direction of Y in the bearings of FIG. 1, and moving means 847 for moving the head 841 and the driving means 845 in the directions of X and Z in the bearings of FIG. 1.

The head 841 is made of a block of metallic material, for example. A plurality of suction holes 842 are formed in this head 841. The suction holes 842 open into the upper and the lower surface of the head 841. These suction holes 842 opening into the upper surface side of the head are connected through tubes 844 to the suction means 843 such as, for example, a suction pump.

The driving means 845 is formed of a solenoid or cylinder (of hydraulic or pneumatic operation), for example. The head 841 is fixed to the leading end of a rod 846 thereof. The head 841 is lowered/raised respectively by the action/inaction of the driving means 845.

The moving means 847 is composed of a rail 848, a slider 849 capable of moving along this rail 848, rollers 851 and 852, and guide rails 853 and 854. The slider 849 is provided with a pair of rollers (not shown) adapted to nip the rail 848 and a motor (not shown) for rotating these rollers. This motor is capable of normal/reverse rotation. When the rollers are rotated by the operation of this motor, the slider 849 moves on the rail 848 within a prescribed range.

One pair of rollers 851 and 852 is installed at either end of the rail 848. These rollers 851 and 852 are rolled on the guide rails 853 and 854. The guide rails 853 and 854 are erected mutually parallel on the container loading case 700 in a direction perpendicular to the rail 848. Further, on the rail 848, a motor (not shown) for rotating the rollers 851 and 852 is set in place. This motor is capable of normal/reverse rotation. When the rollers 851 and 852 are rotated by the operation of this motor, the head 841 is moved together with the rail 848 in the longitudinal direction of the guide rails 853 and 854 within a prescribed range.

The suction means 843, the driving means 845, and the various motors built in the slider 849 and the rail 848 are severally connected electrically to the control means 30. They are operated in response to the signals output from the control means 30.

Now, the operation of the label application device 840 for the application of the labels 831 to a surface will be described below with reference to FIGS. 33 to 37. The labels 831 in this case have the reverse surfaces thereof coated with an adhesive mass.

Figure 48:
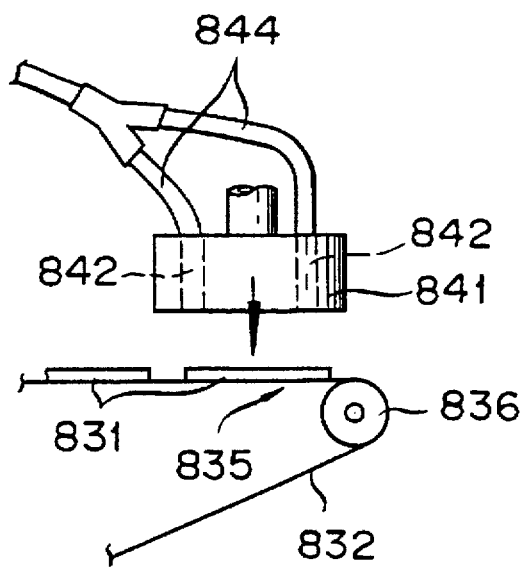
FIGS. 48 to 55 are side views illustrating a process for applying a label by use of a label application device.

The label 831 conveyed from the label producing device 830 is kept waiting at a label suction position 835 as shown in FIG. 48. In the meantime, the rail 848 is moved along the guide rails 853 and 854 and, at the same time, the slider 849 is moved along the rail 848 until the head 841 is positioned directly above the label suction position 835. Subsequently, the head 841 is lowered by the operation of the driving means 845.

Figure 49:
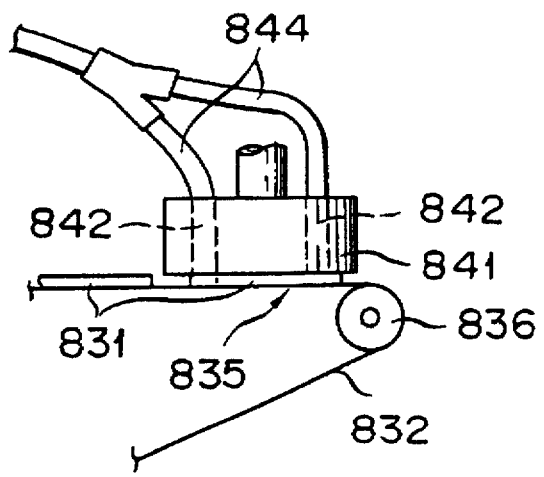

Then, the suction means 843 is operated to give rise to negative pressure in the suction holes 842 of the head 841 and consequently induce the head 841 to suck the label 831 to the lower surface thereof by dint of aspiration as shown in FIG. 49.

Figure 50:
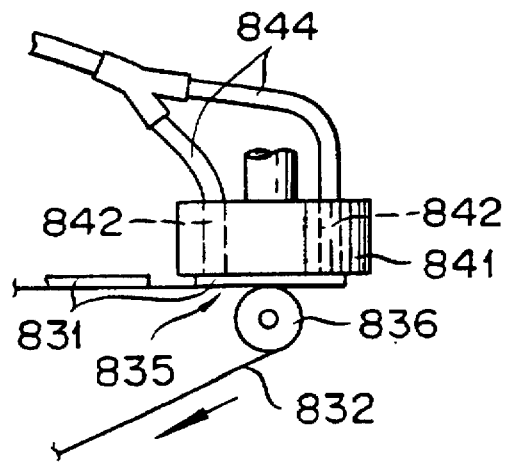

Subsequently, as illustrated in FIG. 50 the head 841 keeping the label 831 attached fast thereto by suction is moved in the direction of Z in the bearings of FIG. 1 by the motion of the slider 849 and, at the same time, the reel 834 is rotated to rewind the label sheet 832 thereon and forward the labels 831 on the label sheet 832 in the direction of Z in the bearings of FIG. 1. As a result, the label sheet 832 is reversed by the roller 836 and the label 831 still attached fast to the head 841 by aspiration is moved toward the right in the bearings of FIG. 50 and eventually peeled off the label sheet 832.

Figure 51:
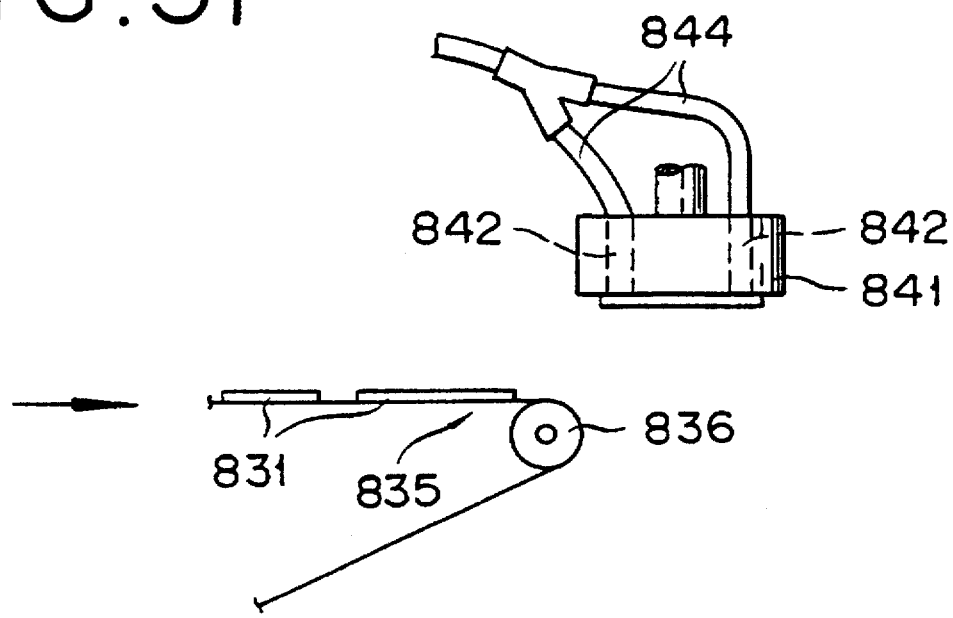

After the label 831 has been peeled off the label sheet 832, the driving means 845 is operated to elevate the head 841 as shown in FIG. 51. Then, the label sheet 832 is advanced and the next label 831 is moved to the label suction position 835 and kept waiting there.

Figure 52:
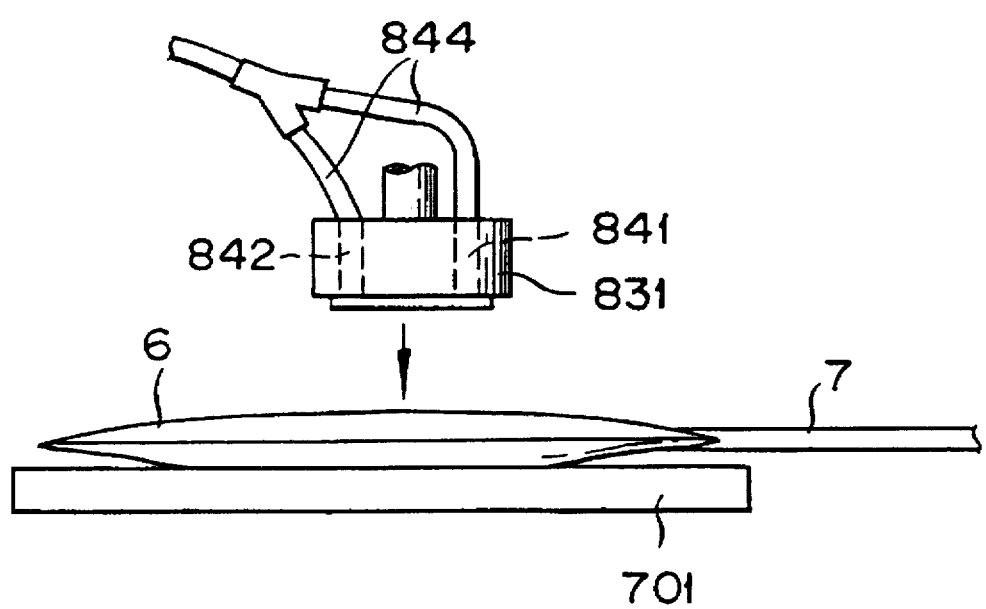

Now, the rail 848 and the slider 849 are operated until the head 841 is positioned directly above the part of the blood component bag 6 mounted on the loading board 701 to which the label is expected to be applied as illustrated in FIG. 52. Then, by the operation of the driving means 845, the head 841 is lowered until the label 831 tacked to the head 841 by aspiration is attached fast to the outer surface of the blood component bag 6. As a result, the label 831 is pasted to the blood component bag 6.

Then, the suction means 843 is suspended from operation to discontinue the work of sucking a label 831. The driving means 845, the slider 849, and the rail 848 are operated until the head 841 is returned to the position directly above the label suction position 835 and readied for the next work of applying a label 831.

When the blood component bag 6 happens to be inflated to a certain extent with a liquid or a gas entrapped therein, it is desired to be subjected to the so-called two-step pressing treatment for the purpose of precluding the otherwise possible defective application of the label 831.

Figure 53:
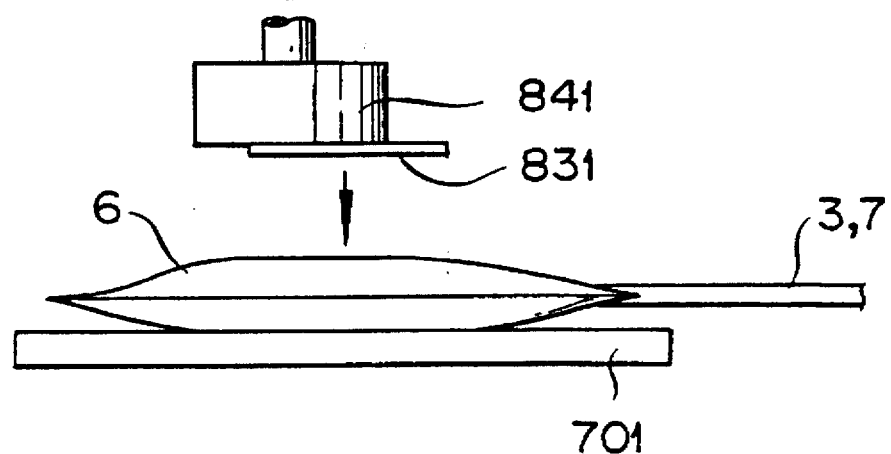
Figure 54:
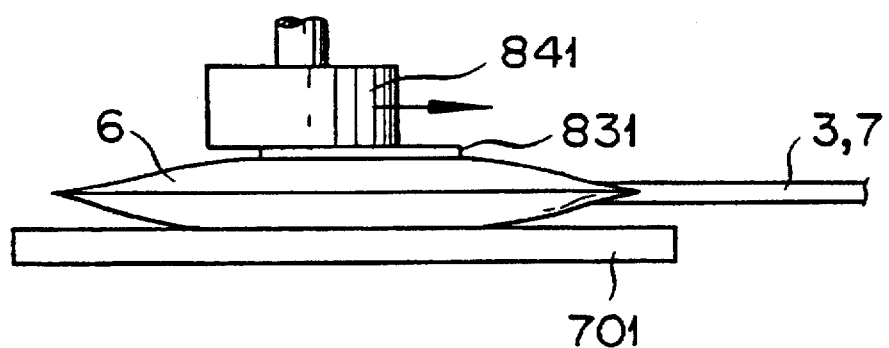
Figure 55:
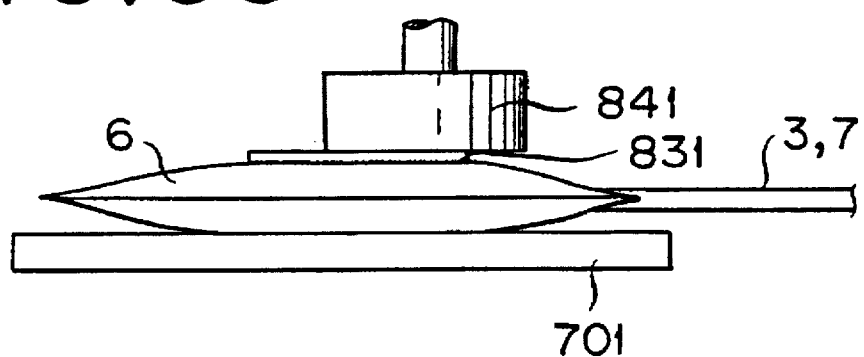

Specifically, the label 831 is sucked fast to the head 841 in such a manner that one end part of the label 831 will protrude from the head 841 as shown in FIG. 53. Then, the head 841 is lowered until the label 831 tacked to the head 841 is attached fast to the outer surface of the blood component bag 6 as shown in FIG. 54. Thereafter, the head 841 is moved toward the right in the bearings of FIG. 55 until the one end part of the label 831 protruding from the head 841 is attached fast to the outer surface of the blood component bag as shown in the diagram. As a result, the label 831 can be infallibly applied fast to the blood component bag 6 even when the blood component bag 6 is in an inflated state or the label 831 is unduly large.

When the label 831 happens to have the reverse surface thereof coated with a hotmelt type adhesive agent, the head 841 is desired to be formed of a heating head resembling a electric heating die so that the label 831 tacked by aspiration thereto will be pasted to the blood component bag 6 by simultaneous exertion of heat and pressure.

(D) Check reader 860

The check reader 860 is composed of a bar code reader 861 similar to the bar code reader 861 described hereinabove and moving means 862 for moving the bar code reader 861 in the directions of X and Z sown in the diagram.

The bar code reader 861 is electrically connected to the control means 30. The information read out by the bar code reader 861 is input into the control means and processed therein as desired.

The moving means 862 is constructed similarly to the moving means 847 mentioned above and is composed of the rail 848, a slider 863 capable of being moved along the rail 848, the rollers 851 and 852 disposed one each of the opposite ends of the rail 848, and the guide rails 853 and 854. The slider 863 is provided with a pair of rollers (not shown) for chucking the rail 848 and a motor (not shown) for rotating these rollers. This motor is capable of normal/reverse rotation. When the rollers are rotated by the operation of the motor, the slider 863 is moved on the rail 848 within of prescribed range. The rail 848 is moved as already described in the longitudinal direction of the guide rails 853 and 854 within a prescribed range. As a result, the bar bode reader 861 is moved along the upper surface of the blood component bag 6 and enabled to carry out the works of the alignment of positions and the reading of code bars.

Thus, the motion of the bar code reader 861 in the direction of X is utilized for aligning the scanning line of the bar code reader 861 and the position of the label pasted to the blood component bag 6 and, where the blood component bag 6 happens to have a plurality of bar codes displayed thereon, also for enabling these bar codes to be sequentially read out.

The check reader 860 which is constructed and operated as described above may be omitted when occasion demands.

(E) Display means 870

The display means 870 is formed of a liquid crystal display or a CRT display, for example. It is electrically connected to the control means 30 and is caused to display various kinds of information in response to signals output by the control means 30. As concrete examples of the information to be indicated by the display means 870, the in formation carried by the bar code 25 to be read by the bar code reader 812, the information carried by the bar code to be formed on the label 831. The number of labels 831 to be printed. The magnitudes detected and displayed by the load cell 702, the amount of red blood cell preserving liquid to be supplied, the conditions for separation and the method for separation used for the centrifuge 20, the present process, the errors to be displayed, and the results of sum total (such as tables) which will be specifically described hereinbelow may be cited.

(F) Printer 880

The printer 880 is a tool for printing out the information displayed on the display means 870, for example. The printer 880 is noted specifically limited to any particular type or construction.

From the viewpoint of simplification of the construction of device, each of the component elements of the data processing device 800 mentioned in (A) through (F) above is desired to be used for serving concurrently two lines of transfer of blood components. These component elements, when necessary, may be severally provided for serving a sole line of transfer of blood components.

Incidentally, the control means 30 is desired to be additionally endowed with the function of aggregating the data to be read out by the reader 810. This function, for example, may consist in memorizing data of 100 cases (100 blood bags) in a memory or in the storage device described above, reading out the data if need arises, aggregating the data, and tabling the result of sum total. In terms of the manner of aggregation, the data may be aggregated in accordance with the order of code numbers or production numbers, the order of dates of manufacture, the order of dates of blood collection, the classification of blood types, the sortation of sites of blood collection, and the classification of one or more items of information carried by bar codes, for example.

The result of such aggregation and the table derived therefrom, as occasion demands, may be displayed on the display means 870 mentioned above, printed out by the printer 880, or memorized by the storage means mentioned above. Further, the data are transmitted through an interface device to a host computer installed at a blood center and aggregated and processed by the host computer. This management can be implemented in the same manner as the management of commodities which is performed by the point of sales system, for example.

The data processing device 800 described above is capable of reading out information concerning the blood held in a given blood bag 2, automatically producing a label having printed thereon a data code symbolized the information corresponding to the information read out as described above, and applying this label to the relevant blood component bag 6. It, therefore, enables the work of producing a label and the work of applying the produced label to the bag to proceed quickly and precisely and also safely in the sense that the otherwise possible selection of wrong labels or wrong bags is precluded. The data processing device 800, therefore, in at an advantage in promoting rationalization and automation of the manufacture of blood products.

When the data processing device 800 is further capable of aggregation and processing of the information which has been read out, it operates to advantage in comprehensive management of the system for the manufacture of blood products.

For this invention, the data processing device 800 is not limited to the construction described above. In the case of the data code which is attached to the label on the blood bag 2 or the blood component bag 6, for example, such a two-dimensional code as the Caruler code which has monochromic mosaic patterns arranged two-dimensionally may be used in the place of such a one-dimensional code as the bar code described above. In this case, a two-dimensional reader using an area sensor (CCD) is adopted for the reader 810 or the check reader 860.

It is also allowable to use a magnetic storage medium, a photomagnetic storage medium, or an optical storage medium as the data code. These storage media are formed in the shape of stripes (tracks). In this case, a read out device which is provided with a magnetic head or an optical head (a light pickup device) is used as the reader.

The label producing device 830 is not limited to the printer described above. It is only required to be capable of forming a data code on the label. When the data code happens to be a magnetic storage medium, for example, the label producing device constitutes itself a magnetic recording device which is adapted to write information in the magnetic storage medium placed on the label.

[Control means 30]

The control means 30 is formed of a central processing unit (CPU) of the kind which is used in a personal computer or a microcomputer. It is provided, as occasion demands, with a memory or such external input means as a keyboard, means for recording data in such a storage medium as a floppy disk and a hard disk, and communication means with other computers.

The control means 30 described above is electrically connected to the centrifuge 20, the operator console 40, the rotary conveying mechanism 101 and the cup conveying mechanism 110 of the first container conveying device 100, the bag pressing device 151 and the roller pump 160 of the blood component transferring device 150, the flow meter 170, the tube pickup device 200, the tube conveying device 300, the tube loading device 350, the tube connecting device 400, the tube shape retention device 450, the tube squeezing device 500, the tube sealing device 550, the container feeding device 600 (601), the second container conveying device 650, the load cell 702, the chemical solution supplying device 750, the reader 810, the label producing device 830, the label application device 840, the check reader 860, the display means 870, and the printer 880. It controls the actions of these component units and processes the obtained data or information.

The component units of the apparatus mentioned above can be manually operated from the operator console 40 or automatically operated sequentially (sequence control) in accordance with a program preset in the control means 30.

[Operator console 40]

The operator console 40, as shown in FIG. 1, has keys, levers, buttons, switches, dials, etc. set in place thereon as required. By the manipulation of these instruments, conditions for various parts of devices can be set, commands to start/stop operations of devices issued, manual operations of various movable parts of devices attained, and operation modes of devices selected, for example.

With the apparatus 1 for the manufacture of blood products in the present example, for the transfer of blood components from the blood bag 2 to the blood component bag 6, a plurality of mutually different modes of transfer can be selected as from among the first, the second, and the third modes which will be specifically described hereinbelow. The selection and the setting of these modes of transfer are performed by use of the operator console 40.

The operator console 40 does not need to be limited to the type which is installed in the main body 15 of the apparatus. It may be a type which will be operated by remote control using or not using a wire.

As the substance for forming the sheet material of which the blood bag 2 (or 8) and the blood component bag 6 is made, soft polyvinyl chloride is advantageously used, for example. As concrete examples of the plasticizer for use in this soft polyvinyl chloride, di(ethylhexyl) phthalate (DEHP) and di-(n-decyl)phthalate (DnDP) may be cited. The content of this plasticizer is desired to be in the approximate range of 30 to 70 parts by weight, based on 100 parts by weight of the polyvinyl chloride.

Other substances which are available for the formation of the sheet material of the bags 2, 6, and 8 are polyolefins, ie. the polymers obtained by polymerizing or copolymerizing such olefins or diolefins as ethylene, propylene, butadiene, and isoprene. Polyethylene, polypropylene, ethylene-vinyl acetate copolymer (EVA), polymer blends obtained by blending EVA with various thermoplastic elastomers, and arbitrary combinations thereof may be cited as concrete examples. It is permissible to use instead such polyesters as polyethylene terephthalate (PET), polybutylene terephthalate (PBT), and poly-1,4-cyclohexane dimethyl terephthalate (PCHT) and polyvinylidene chloride.

The sheet materials for the bags 2, 6, and 8 may be made of different substances in different thickensses which are suitably selected depending on the kinds of blood components to be contained in the bags. The blood component bag 6 used for storing blood plasma, for example, is destined to be frozen for storage. The sheet material for this bag 6, therefore, is desired to be made of such a substance as polyethylene, polypropylene, or ethylene-vinyl acetate (EVA) copolymer which exhibits high strength at low temperatures. The blood components bag 6 which stores platelets is desired to possess improved perviousness to gas and consequently impart an elongated shelf life to the stored platelets. Thus, the sheet material for this bag 6 is desired to be made of a DnDP-plasticized polyvinyl chloride in a relatively small thickness.

As concrete examples of the material for the formation of the tubes 3, 7, and 752, polyvinyl chloride, polyolefins such as polyethylene, polypropylene, and EVA, polyesters such as PET and PET, thermoplastic elastomers such as polyurethane, polyamide, silicone, polyester elastomer, polyamide elastomer, and styrene-butadiene copolymer, and arbitrary combinations thereof may be cited. Among other materials mentioned above, polyvinyl chloride proves particularly desirable in respect that it befits automated mass production of the tubes under discussion.

The two tubes to be joined by the tube connecting device 400 are desired to be made of an identical material or similar materials from the viewpoint of facilitating and ensuring the union thereof. The two tubes to be connected are desired to have substantially identical internal and external diameter.

Now, one example of the method of this invention for the manufacture of blood products will be described below. Blood products can be manufactured by using the apparatus 1 for manufacture of blood products described above and adopting the steps of process described hereinbelow. The method to be described hereinbelow adopts the mode of simultaneously transferring blood components from two blood bags 2 to two corresponding blood component bags 6 by use of two lines of transfer of blood component of the apparatus 1 for manufacture of blood products. Preparatorily to the execution of the following steps, therefore, the information regarding the adoption of this particular mode of transfer (second mode of transfer) is preset in the operator console 40.

[A-1] The cup holding the blood bag 2 packed with collected blood is conveyed by the cup conveying mechanism 110, set in place on the rotor of the centrifuge 20, and subjected to centrifugal separation under prescribed conditions by the operation of the centrifuge 20. In consequence of the centrifugal separation, the blood in the blood bag 2 is separated into three blood components, ie. blood plasma, buffy coat, and red blood cells from the upper layer downward. The rotor of the centrifuge 20 allows about two to six cups 4 to be set thereon at once.

[A-2] After the centrifugal separation, the cup conveying mechanism 110 is operated to extract all the cups 4 one by one from the rotor of the centrifuge 20 and place them temporarily on the tray 11.

[A-3] By the operation of the cup conveying mechanism 110, the cups 4 seated on the tray 11 are removed one by one and conveyed until they are retained by the cup retaining member 103 located on the centrifuge 20 side of the rotary conveying mechanism 101. After two cups 4 (the first and the second cup 4) have been lodged in one cup retaining member 103, the rotator 102 is rotated by 90° counterclockwise in the bearings of FIG. 1. As a result, the two cups 4 retained by the cup retaining member 103 are conveyed to the information reading unit 811 and one of them is caused to confront the reader 810.

In preparation for the next transfer of blood components, the cup conveying mechanism 110 is actuated after the rotation of the rotator 102 to remove the third and the fourth cup 4 newly placed on the tray and convey them until they are loaded in the cup retaining member 103 located on the centrifuge 20 side.

[A-4] In the reader 810, the driving means 821 is actuated to press the blood bags 2 and the cup 4 together with the transparent plate 820 and impart a flattened shape to the label 23 applied to the blood bag 2 and, at the same time, the moving means 814 is actuated to move the bar code reader 812 until the scanning line 813 thereof reaches the position of the bar code 25 on the label 23 which is to be read. Then, the bar code reader 812 is operated to read the bar code 25. The data thus read out of the bar code 25 are input into the control means 30, processed in the arithmetic section as desired, and then stored temporarily in the built-in memory.

[A-5] the transparent plate 820 is returned to the home position. Then, the reader 810 is moved in the direction of X and operated to read in the same manner as described above the bar code 25 on the label 23 tacked to the blood bag 2 which is held in the other cup 4. The data thus read out are input into the control means 30, processed in the arithmetic section as desired, and stored temporarily in the built-in memory.

[A-6] The rotator 102 is further rotated by 90° counterclockwise in the bearings of FIG. 1. As a result, the two cups 4 positioned theretofore in the information reading unit 811 are conveyed to the blood component transferring device 150 and are severally caused to confront the bag pressing device 151. Further by this rotation of the rotator 102, the third and the fourth cup 4 are placed in the information reading unit 811. After the rotation of the rotator 102, the cup conveying mechanism 110 is actuated to remove the fifth and the sixth cup 4 newly placed on the tray 11 and convey them until they are loaded in the cup retaining member 103 which is positioned on the centrifuge 20 side.

[A-7] The second container conveying device 650 is actuated to remove the uppermost of unused blood component bags 6 held inside the magazine 602 in the bag supplying device 600 and convey it until it is seated on the loading board 701 of each of the loading bases 700. In this case, the blood component bags 6 which are placed on the two loading boards 701 may be both supplied from one of the two bag supplying devices 600 or one each supplied from the two bag supplying devices 600.

The leading end part of the tube 7 connected to the blood component bag 6 which is seated on the loading board 701 is set in place between the rollers 320 near the loading board 701 by the operation of the same tube pickup device as described above.

[A-8] The control means 30 suitably reads out the data concerning the information symbolized by the bar code 25 stored in the memory thereof, outputs a signal for forming on the label 831 a bar code corresponding to the data mentioned above or the data together with the aforementioned added information to the label producing device 830. The label producing device 830, in response to the signal, produce a label 831 having the bar code printed therein, and discharges it.

[A-9] by the operation of the label application device 840, the label 831 discharged from the label producing device 830 is handled in procedure described above and eventually pasted to the outer surface of the blood component bag 6 placed on the loading board 701. The production and the applying of labels 831 are carried out on each of the two blood component bags 6.

[A-10] The moving means 862 of the check reader 860 is actuated to move the bar code reader 861 until the scanning line thereof coincides with the position of the bar code on the label pasted to the blood component bag 6 to be read out. Then, this bar code is read out by the bar code reader 861.

[A-11] The data thus read out by the bar code reader 861 are input into the control means 30 and processed in the arithmetic section thereof. The control means 30 examines the bar code of the label 831 tacked to the blood component bag 6 to determine whether or not the bar code is free from such defects as misprint and, at the same times, compares the information symbolized by the bar code on the blood component bag 6 with the data stored in the memory of the control means 30, namely the information carried by the bar code 25 on the corresponding blood bag 2 to determine whether or not they are identical.

For the purpose of confirming this identicalness, all the information that is coded by the bar code is not required to be used for the comparison. The comparison suffices for its purpose by using only such important items of information as code number, production number of blood product, other similar numbers, and blood type.

[A-12] When the identicalness of the bar codes on the two corresponding bags 2 and 6 is confirmed, the fact of this confirmation is displayed on the display means 870. When this identicalness is not confirmed or when the bar code formed on the label 831 is found to contain such defects as misprint, the control means 30 gives an alarm and, at the same time, suspends the work of manufacturing blood products.

The alarm is implemented by turning on an alarm lamp (not shown), sounding an alarm buzzer or spreading a vocal alarm through a public announcing system (not shown), or causing the display means 870 to display an alarm in the form of characters or figures.

[A-13] The tube pickup device 200 is actuated as described above to take hold of the leading end part of the tube 3 and convey it until it reaches the gap between the rollers 312 of the tube conveying devices 300. At this time, the midway of the tube 3 is set in the roller pump 160 having the head 162 thereof kept in an opened state.

[A-14] The rollers 312 are set rotating to convey the tube 3 until the leading end part of the tube 3 protrudes from the upstream side end part of the conveying rail 303.

[A-15] The rollers 320 and 311 are set rotation to conveying the tube 7 connected to the blood component bag 6 on the loading board 701 until the leading end part thereof passes the recess 309.

[A-16] The tube loading device 350 is actuated as described above to load the tubes 3 and 7 in the tube connecting device 400.

[A-17] The tube connecting device 400 is actuated as described above to effect aseptic connection of the tubes 3 and 7. In the construction illustrated in FIG. 1, since the tube connecting device 400 is intended for concurrently serving two lines of transfer of blood components, it is moved in the direction of Z and operated to connect tubes alternately in the two lines of transfer of blood components.

The severed portions of tubes which are useless any longer are removed from the holders 410 and 420 and discharged by the operation of the tube loading device 350.

[A-18] After the joined tube has been conveyed until the joined part thereof is positioned in the tube inserting path 480 of the tube shape retention device 450, the tube shape retention device 450 is actuated as described above to correct deformation caused in the joined part of tube and secure an inner flow path of the tube.

In the meantime, the head 162 of the roller pump 160 is closed and readied for transfer of liquid.

[A-19] The bag pressing device 151 and the roller pump 160 are actuated to transfer the blood plasma forming the upper layer in the blood bag 2 through the connected tubes 3 and 7 into the blood component bag 6. In this case, the transfer of the blood plasma to the blood component bag 6 is automatically stopped when the weight detected by the load cell 701 installed in the container bag 6 reaches the supporting the relevant blood component bag 6 reaches the preset value (the weight of the blood component bag 6 which has recovered the substantially whole amount of blood plasma).

When the apparatus is provided with boundary detecting means for detecting the interfacial boundaries of blood components mentioned above, the transfer of the blood plasma to the blood component bag 6 may be stopped on the basis of the data derived by the detecting the means.

[A-20] The tube sealing device 550 is utilized for fusing and sealing a midway of the tube 3 or 7 and cutting the sealed portion 75 of the tube and, when necessary, breaking and separating thin-wall connecting portions 76 of the connected tube by exertion of tensile force on the tube. As a result, the blood bag 2 and the blood component bag 6 are separated from each other both in a tightly closed state.

Optionally, this step may be carried out after the following step of [A-21].

[A-21] The tube squeeze device 500 is actuated as described above to induce flow of the blood components still remaining in the tube toward the blood component bag 6 side which is placed on the loading board 701. Incidentally, since the part of the tube which has been squeezed is unusable, the general part of the tube including the point at which the squeezing of tube is terminated is sealed and out again by the step of [A-20]. The severed segment of tube may be discarded. In this case, the discarded tube segment is recovered in the waste recovery box mentioned above.

[A-22] The blood component bags 6 placed on the two loading boards 701 and already packed with blood plasma are conveyed by the second container conveying device 650 and thrown into the shooter 711 of the second container recovering case 710. In this case, the two blood component bags 6 placed one each on the loading boards 701 may be thrown into two different shooters 711 adjoining the loading boards 701 or into one and the same shooter 711.

[A-23] By sequentially carrying out the same steps as the aforementioned steps of [A-7 to [A-12] and [A-14] to [A-22], the buffy coat forming the intermediate layer in the blood bag 2 is transferred into unused blood component bags 6 and the blood component bags 6 now packed with the buffy coat are tightly sealed and recovered in the shooters 711. In this case, the blood component bags 6 which are to be used for receiving the transferred buffy coat may have a platelet preserving liquid placed therein in advance of the use.

At the step of [A-22]]mentioned above, when the two blood component bags 6 containing the blood plasma have been thrown into one and the same shooter 711, the two blood component bags 6 containing the buffy coat will be thrown into the other shooter 711. This rule facilitates the subsequent management of blood products because the blood components bags 6 are accumulated in the different shooters 711 as sorted by kid of blood product.

[A-24] The rollers 321 and 311 are rotated to convey the tube 752 connected to the chemical solution container 751 at the chemical solution feeding device 750 until the leading end part thereof passes the recess 309.

[A-25] The tube loading device 350 is actuated in the same manner as in the aforementioned step of [A-16] to load the tubes 3 and 752 in the tube connecting device 400.

[A-26] The tube connecting devices 400 is operated in the same manner as in the aforementioned step of [A-17] to effect aseptic connection of the tubes 3 and 752.

[A-27] The connected tube is conveyed in the same manner as in the aforementioned step of [A-18] until the connected part of tube is positioned in the tube inserting path 480 of the tube shape retention device 450. Then, the tube shape retention device 450 is actuated to correct the deformation formed in the connected part of tube and secure an inner flow path of the connected tube.

[A-28] The pressing plate 152 of the bag pressing device 150 is returned to the home position thereof to relieve the blood bag 2 of pressure.

[A-29] The roller pump 160 is rotated in the direction opposite to the direction mentioned above to advance the red blood cell preserving liquid 760 held in the chemical solution container 751 through the connected tubes 752 and 3 into the blood bag 2 containing red blood cells.

[A-30] The tube sealing device 550 is operated to fuse and seal the midway of the tube 3 and 752 and, at the same time, cut the sealed portion 75 of tube and, when necessary, break and separate the thin-wall connecting portion 76 by exerting tensile force on the tube.

[A-31] The reader 811 is operated to carry out the same steps as the aforementioned steps of [A-4] and [A-5] on the blood bags 2 held in the third and the fourth cup placed in the information reading unit 811 so as to read the bar codes 25 on the blood bags 2. The obtained information is to be processed and stored by the control means 30.

[A-32] The roller 321 is rotated in the direction opposite to the direction mentioned above to return the tube 752 until the leading end part thereof is positioned in the groove 306 of the branched rail 301'.

[A-33] The rotator 102 is further rotated by 90° counterclockwise in the bearings of FIG. 1. As a result, the two cups theretofore opposed to the bag pressing device 150 are conveyed to the first container recovering case 250 on the front side of the apparatus 1 for manufacture of blood products and placed opposite the chucking means 252.

After the rotation of the rotator 102, the cup conveying mechanism 110 is operated to remove the seventh and the eighth cups 4 newly placed on the tray 11, convey them, and loaded in the cut retaining member 103 positioned on the centrifuge 20 side.

[A-34] The chucking means 252 is actuated to extract the two cups 4 held in place by the cup retaining member 103 and thrown them into the shooter 251 of the first container recovering case 250.

[A-35] Thereafter, the aforementioned steps of [A-6] to [A-33] are repeated until all the cups 4 storing the blood bags 2 already subjected to centrifugal separation and standing on the tray 11 are removed for further processing.

In this invention, a step of successively rotating the rotator 102 at angular intervals of 90° thereby loading all the notches 105 in the four cup retaining members 103 with cups 4 may precede the step of [A-4] and the subsequent steps.

Now, one example of the method for manufacturing a platelet preparation from the buffy coat obtained above by use of the apparatus 1 for manufacture of blood products will be described below. The following method adopts the mode of transfer of blood components from two blood component bags 6 containing the buffy coat to two corresponding blood component bags 6 through two lines of transfer of blood components. The information about the fact of adopting this particular mode of transfer (the second mode of transfer), therefore, is preset in the operator console 40 prior to the implementation of the following steps.

[B-1] The blood component bags 6 filled with the buffy coat (hereinafter referred to as "BC bags") are taken out of the shooter 711 and placed in the cups. The cups 4 are conveyed and set in place on the rotor of the centrifuge 20 by the operation of the cut conveying mechanism 110. The centrifuge 20 is actuated to effect centrifugal separation on the cups 4 under prescribed conditions. As a result, the buffy coat in the BC bags is separated into an upper layer of platelets (platelet concentrated plasma) and a lower layer of white blood cells.

[B-2 and B-3] The same steps as the aforementioned steps of [A-2] and [A-3] are carried out.

[B-4] In the same manner as in the aforementioned step of [A-4], the label 831 tacked to the BC gag is pressed into flattened state, the bar code on the label is read out by the bar code reader 812, and the obtained data thus is input into the control means 30 to be processed and stored therein as required.

[B-5 to B-12] The same steps as the aforementioned steps of [A-5] to [A-12] are carried out.

[B-13 to B-18] In the same manner as in the aforementioned steps of [A-13] to [A-18], the tube pickup device 200 and the tube conveying device 300 are operated to convey the tube 7 on the BC bag side, the tube conveying device 300 is actuated to convey the tube 7 on the blood component bag 6 side and load the two tubes on the tube connecting device 400, the tube connecting device 400 is used to connect the two tubes, and the tube shape retention device 450 is actuated to correct deformation of the connected part of tube.

[B-19] The bag pressing device 151 and the roller pump 160 are operated to transfer the platelets forming the upper layer in the BC bag through the connected tubes 7 and 7 into the blood component bag 6 on the loading board 701. In this case, the transfer of the platelets to the blood component bag 6 is stopped automatically when the weight detected by the load cell 702 set in place on the container loading case 700 for seating the blood component bag 6 reaches the preset level (the weight of the blood component bar 6 which has recovered the substantially whole amount of platelets).

When the apparatus 1 for manufacture of blood products is provided with boundary detecting means for detecting the interfacial boundaries of the blood components mentioned above, the transfer of the platelets to the blood component bag 6 may be stopped based on the result of detection by the means mentioned above.

When the BC bags to be used at the aforementioned step of [A-23] do not contain the platelet preserving liquid, the blood component bags 6 to which the platelets are to be transferred are desired to have the platelet preserving liquid placed therein in advance of the transfer of platelets.

[B-20 and B-21] The same steps as the aforementioned steps of [A-20] and [A-21] are carried out.

[B-22] In the same manner as in the aforementioned step of [A-22], the blood component bags 6 placed on the two loading boards 701 and already filled with platelets are conveyed, thrown into the desired shooter 711, and recovered.

[B-23] The pressing plate 152 of the bag pressing device 150 is returned to the home position thereof to relative the BC bags of pressure.

[B-24] The same steps as the aforementioned steps of [A-4] and [A-5] are carried out on the BC bags held in the third and the fourth cups 4 which are positioned in the information reading unit 811.

[B-25 and B-26] The same steps as the aforementioned steps of [A-33] and [A-34] are carried out.

[B-27] Thereafter, the steps of [B-6] to [B-26] mentioned above are repeated until all the cups 4 placed on the tray 11 and readied for accommodating the BC bags already subjected to centrifugal separation are moved away the tray 11 for further processing.

In this invention, a step of successively rotating the rotator 102 at angular intervals of 90° thereby loading all the notches 105 in the four cup retaining members 103 with cups 4 may precede the step of [B-4] and the subsequent steps.

In this invention, the mode of transferring blood components from one blood bag 2 (or BC bag) to one corresponding blood components bag 6 through one of the two lines of transfer of blood components in the apparatus 1 for manufacture of blood products may be adopted instead. In this case, the information about the fact of adopting this particular mode of transfer (first mode of transfer) is present in the operator console 40 prior to the implementation of the steps mentioned above. When this mode of transfer is adopted, the step of lodging one cup 4 in either of the notches 105 of one cup retaining member 103, the step of moving the reader 810 in the direction of X, and the step of moving the tube connecting device 400 in the direction of Z are not necessary.

Further, in this invention, it is permissible to use blood bags 8 which are constructed as illustrated in FIG. 38 and transfer blood components from these blood bags 8 separately to different blood components bags 6.

Figure 56:
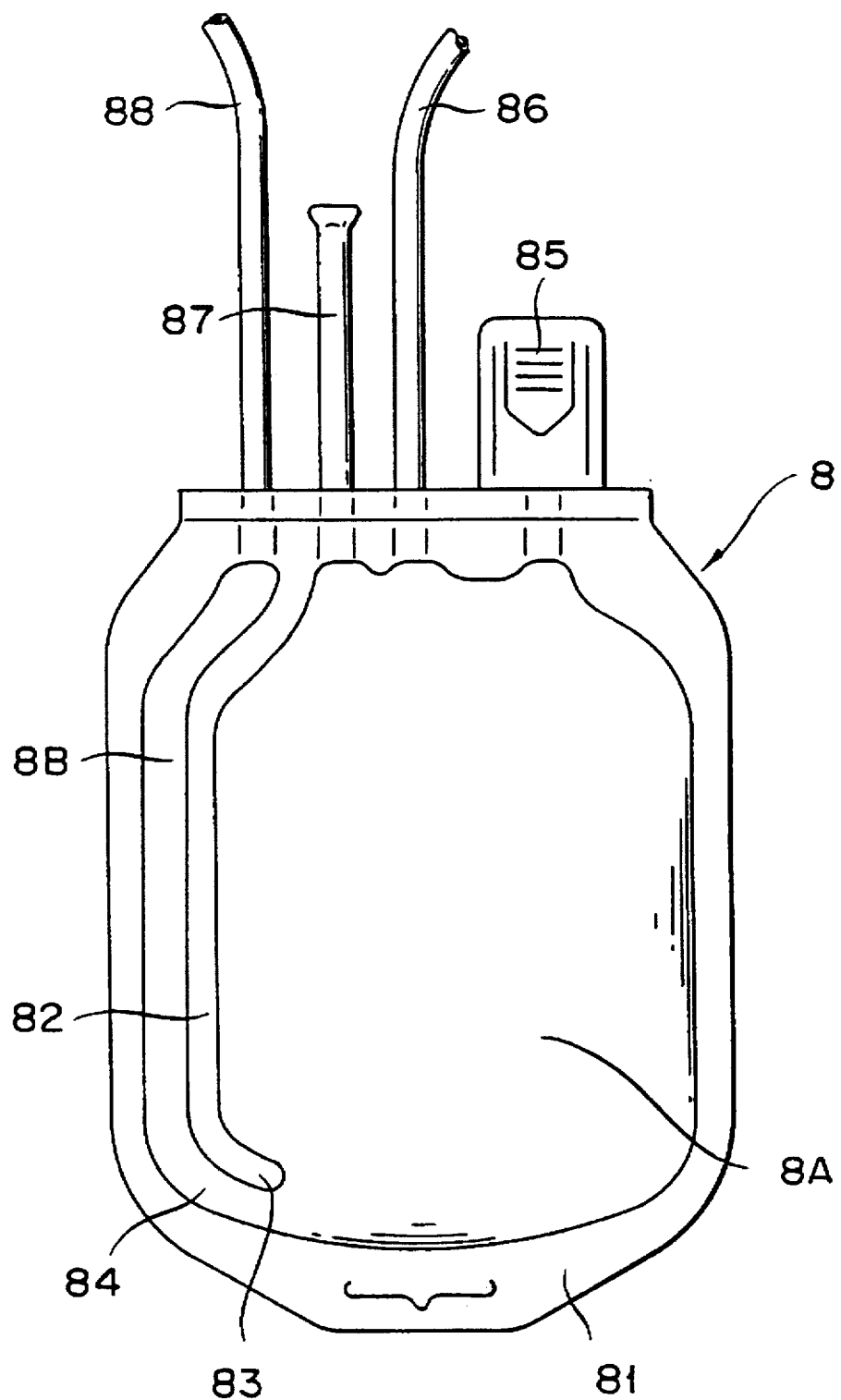
FIG. 56 is a plan view illustrating a blood bag to be used in the present invention.

A blood bag 8 illustrated in FIG. 56 is constructed by superposing the same sheet materials as mentioned above and fusing (thermal fusion or high-frequency fusion, for example) or adhesively joining the superposed sheet materials in a peripheral sealed portion 81 defining a bag-like enclosure. The interior of this blood bag 8 is partitioned with a ribbonlike partition portion 82 into two spaces 8A and 8B. The space 8A accounts for the greater part of the inner cavity of the blood bag 8 and the space 8B forms a ribbonlike cavity extending along the lateral part of the blood bag 8.

The space 8B fulfills the function of a flow path for discharging out of the blood bag 8 the red blood cells which form the lower of the three layers of separated blood components. The ribbonlike shape imparted to this space 8B (reduced to the shape of a slender column in an inflated state) enables the red blood cells in the process of flowing through the space 8B from the lower part (bottom part) side to the upper part side of the blood bag 8 to move smoothly and does not easily allow them to flow back.

The two spaces 8A and 8B communicate with each other near a lower end part 83 of the partition portion 82, namely near the bottom part of the blood bag 8 (communicating part 84) as shown in FIG. 56. The upper end of the partition portion 82 is connected to the loading board 81.

The lower end part 83 of the partition portion 82 assumes a curved shape, particularly a roundish shape. The lower end part 83 may assume any position, providing it should fall below the boundary between the lower layer (red cells) and the intermediate layer (buffy coat) which are formed after the blood held in the blood bag 8 has been separated by centrifugation.

In the upper part of the blood bag 8, a discharge port 85 for transfusion openably sealed with a peel tab is formed. Further to the upper part of the blood bag 8, three tubes 86, 87, and 88 are connected.

Of these three tubes, the tube 86 serves the purpose of permitting discharge of the blood plasma forming the upper layer. The inner cavity of this tube 86 communicates with the space 8A. The tube 87 fulfills the role of introducing collected blood into the blood bag 8. The inner cavity of this tube 87 communicates with the space 8A. After the introduction of collected blood, this tube 87 is sealed by fusion, with the sealed portion out. The tube 88 plays the part of discharging the red blood cells forming the lower layer. The inner cavity of this tube 88 communicates with the space 8B.

Now, one example of the method of this invention for the manufacture of blood products by use of the blood bag 8 mentioned above will be described. The following method adopts the mode of transferring two different blood components from one blood bag 8 to two different blood component bags 6 by use of two lines of transfer of blood components of the apparatus 1 for manufacture of blood products. The information about the fact of adopting this particular mode of transfer (third mode of transfer) is present in the operator console 40, therefore, prior to the implementation of the following steps.

[C-1 and C-2] The same steps as the aforementioned steps of [A-1] and [A-2] are carried out.

[C-3] In the same manner as in the aforementioned step of [A-3], the cups 4 are conveyed and lodged in the cup retaining member 103. In this case, one cup 4 is lodged in either of the notches 105 (that on the left side, for example) of the cup retaining member 103 and the rotator 102 is successively rotated at angular intervals of 90° to allow cups 4 (a total of four cups) to be lodged one each in the cup retaining members 103.

[C-4] The same step as the aforementioned step of [A-4] is carried out on the first cup 4 positioned in the information reading unit 811.

[C-5] The transparent plate 820 is returned to the home positioned thereof.

[C-6] The rotator 102 is further rotated by 90° counterclockwise in the bearings of FIG. 1. As a result, the cup 4 theretofore positioned in the information reading unit 811 is conveyed to the blood component transferring device 150 placed opposite the bag pressing device 151 and, at the same time, the second cup 4 is set in place in the information reading unit 811. [C-7 to C-12] The same steps as the aforementioned steps of [A-7] to [A-12] are carried out.

[C-13] In one of the lines for transfer of blood components, the tube pickup device 200 is actuated to take hold of the leading end part of the tube 86 and transfer it until it reaches the gap between the rollers 312 of the tube conveying device 300. Likewise in the other line for transfer of blood components, the leading end part of the tube 88 is conveyed until it reaches the gap between the roller 312. At this time, the midways of the tubes 86 and 88 are set in place in the roller pump 160 which has the head 162 thereof kept in an opened state.

[C-14] The roller 312 is rotated to convey the tubes 86 and 88 until the leading end parts of the tubes 86 and 88 severally protrude from the upstream side end part of the conveyor rail 303.

[C-15] The rollers 320 and 311 are rotated to convey the tubes 7 connected to the blood component bags 6 on the loading board 701 until the leading end parts thereof pass the recess 309.

[C-16] The tube connecting device 400 is positioned on either of the lines for transfer of blood components and the tube loading device 350 is operated to load the tubes 86 and 7 in the tube connecting device 400.

[C-17] The tube connecting device 400 is actuated to effect aseptic connection of the tubes 86 and 7. Further, the tube loading device 350 is used to remove severed segments of tube from the holders 410 and 420 and discard them as useless.

[C-18] The tube connecting device 400 is moved in the direction of Z and positioned on the other line for transfer of blood components and the tube loading device 350 is actuated to load the tubes 88 and 7 in the tube connecting device 400.

[C-19] The tube connecting device 400 is operated to effect aseptic connection of the tubes 88 and 7. Further, the tube loading device 350 is used to remove severed segments of tube from the holder 410 and 420 and discard them as useless.

[C-20] The same step as the aforementioned step of [A-18] is carried out.

[C-21] The bag pressing device 151 and the roller pump 160 are operated to transfer the blood plasma forming the upper layer in the blood bag 8 through the connected tubes 86 and 7 into one of the blood component bags 6 and, at the same time, transfer the red blood cells forming the lower layer in the blood bag 8 through the space 8B and the connected tubes 86, 7 into the other blood component bag 6. In this case, the transfer of the blood plasma to the blood component bag 6 is automatically stopped after the weight of the blood component bag 6 detected by the load cell 702 on the side of the blood component bag 6 receiving the blood plasma has reached a preset level (the weight of the blood component bag 6 which has recovered the substantially whole amount of the blood plasma). The procedure just mentioned holds good for the blood component bags 6 to which the red cells are to be transferred.

When the apparatus 1 for manufacture of blood products is provided with boundary detecting means capable of detecting the interfacial boundaries of the blood components mentioned above, the transfer of blood plasma an red blood cells to the blood component bags 6 may be stopped based on the result of detection by the detecting means mentioned above.

After completion of the transfer of blood plasma and red blood cells to the relevant blood components bags 6, the buffy coat forming the intermediate layer remains in the blood bag 8.

[C-22 and C-23] The same steps as the aforementioned steps of [A-20] and [A-21] are carried out.

[C-24] In the same manner as in the aforementioned step of [A-22], the blood component bag 6 already filled with blood plasma and the blood component bag 6 already filled with red blood cells and both placed on the loading boards 701 are severally conveyed by the second container conveying device 650 and thrown into the shooter 711 of the second container recovery case 710. In this case, the two blood component bags placed on each of the loading boards 701 may be thrown into different shooters 711 adjoining the loading boards 701 or into one and the same shooter 711. In the former case, the subsequent management of the blood component bags 6 is facilitated because these blood component bags 6 are piled in the shooters 711 as sorted by kind of blood product.

[C-25 to C-29] In the same manner as in the aforementioned steps of [A-24] to [A-28], the conveyance of the tubes 86 and 752, the loading of the tubes in the tube connecting device 400, the connection of the tubes, the shaping of the connected part of tubes, and relieving of the blood bags 8 from pressure are carried out in one of the lines for transfer of blood components.

[C-30] In the same manner as in the aforementioned step of [A-29], the roller pump 160 is rotated in a direction opposite to the aforementioned direction to convey the platelet preserving liquid in the chemical solution container 751 through the connected tubes 752 and 86 to the blood bag 2 containing the buffy coat.

[C-31 and C-32] The same steps as the aforementioned steps of [A-30] and [A-32] are carried out.

[C-33 to C-38] In the same manner as in the aforementioned steps of [A-7] to [A-12], the placement of the blood component bags 6 (BC bags) on the loading board 701, the production of labels 831 by the label producing device 830, the applying of the labels 831, the reading and conformation of the information on the labels by the check reader 860 are carried out in the line for transfer of blood components opposite the line used for the addition of the platelet preserving liquid mentioned above.

[C-39 to C-44] In the same manner as in the aforementioned steps of [A-12] to [A-18], the conveyance of the tube 88 by the tube pickup device 200 and the tube 7 by the tube conveying device 300, and the loading of the two tubes 88 and 7 in the tube connecting device 400, the connection of the tubes, and the shaping of the connected portion of tubes are carried out.

[C-45] The bag pressing device 151 and the roller pump 160 are operated to transfer the buffy coat in the blood bag 2 through the space B and the connected tubes 88 and 7 to the BC gas on the loading board 701.

[C-46 and C-47] The same steps as the aforementioned steps of [A-20] and [A-21] are carried out.

[C-48] In the same manner as in the aforementioned step of [A-22], the BC bags already filled with the buffy coat and placed on the loading board 701 are thrown into the desired shooters 711 and recovered.

[C-47] In the same manner as in the aforementioned step of [A-28], the blood bag 8 is relieved of pressure.

[C-50] The same steps as the aforementioned steps of [C-4] and [C-5] are carried out the second cup 4 positioned in the information reading unit 811.

[C-51] In the same manner as in the aforementioned step of [A-33], the rotator 102 is further rotated by 90° counterclockwise in the bearings of FIG. 1 to convey the cup 4 theretofore positioned opposite the bag pressing device 150 to the first container recovering base 250.

[C-52] The same step as in the aforementioned step of [A-34] is carried out.

[C-53] The aforementioned steps of [C-6] to [C-52] are carried out on all the cups lodged in the four cup retaining members 103 of the rotator 102.

[C-54] The aforementioned steps of [C-3] to [C-53] are repeated until the cups 4 on the tray 11 holding the blood bags 8 already subjected to centrifugal separation are moved away for further processing.

Then, the same steps as the aforementioned steps of [B-1] to [B-27] are carried out for manufacturing a platelet preparation from the buffy coat obtained in the steps [C-3] to [C-54] by use of the apparatus 1 for manufacture of blood products. In this case, the information about the fact of adopting the second mode of transfer is preset in the operator console 40.

For this invention, a blood bag which is constructed by connecting a tube for discharging blood plasma to the upper end of a bag and a tube for discharging red blood cells to the lower end of the bag (see; JP-B-63-20,144) may be used on account of the equality of function to the blood bag 8 mentioned above. When the blood bag of this construction is used, manufacture of blood products can be attained by the same method as is adopted for the manufacture of blood products by use of the blood bag 8.

The first and the second container used in the examples described above are invariably formed of a flexible bag. This invention does not limit the first and the second container to this particular flexible bag. They may be such containers as bottles. Further, the first container may be different in shape and size (volume) from the second container.

The apparatus and the method for manufacture of blood products according to this invention have been described with respect to typical constructions which are illustrated in various diagrams. This invention nevertheless is not limited to these examples. Particularly in the present invention, while it is most desirable for all the series of steps mentioned above to be carried out automatically, part of the steps and part of the modes of transfer may be modified or carried out manually or by manual works as occasion demands.

What is claimed is:

1. An apparatus for the manufacture blood products comprising:
   a blood component transferring device for transferring from a first container to a second container at least one of a plurality of separated blood components stored in the first container, and
   a tube connecting device for aseptically connecting a first tube communicating with the first container to a second tube communicating with the second container to permit said blood component transferring device to transfer at least one of the blood components stored in the first container to the second container through the interconnected first and second tubes;

said tube connecting device comprising:
a pair of retaining members for retaining the first and second tubes in a parallel arrangement;
a heat plate movably disposed between said two retaining members and adapted to fuse and cut the first and second tubes;
a tube sealing device for causing at least one of said two retaining members to be moved relative to the other retaining member and for joining cut surfaces of the first and second tubes;
a tube shape retention device for removing deformation in the first and second tubes imparted during joining of the first and second tubes, said tube shape retention device including a tube inserting space for permitting insertion of a tube through the space, a pair of pressing members provided with pressing surfaces for chucking a deformed part of the tube inserted through the space, and drive means for moving said pressing surfaces in opposite directions relative to each other.

2. An apparatus according to claim 1, wherein said blood component transferring device comprises compressing means adapted to compress the first container and expel blood components from the first container.

3. An apparatus according to claim 2, wherein said blood component transferring device further comprises aspirating means adapted to aspirate said blood components from said first container.

4. An apparatus according to claim 3, wherein said aspirating means is a roller pump.

5. An apparatus according to claim 1, wherein said tube connecting device comprises a tube loading device for seating the first and second tubes on said retaining members, and said tube loading device comprising a conveying head provided with two chucks for chucking the tubes at mutually different positions and drive means for moving at least one of said two chucks and varying the distance between said two chucks.

6. An apparatus according to claim 1, wherein said apparatus further comprises a tube sealing device comprising cutting means for cutting fused portions of the tubes.

7. An apparatus according to claim 6, wherein said tube sealing device comprises a pair of heating heads each having a tube chucking surface, said tube chucking surface of at least one of said heating heads being provided with a protuberance.

8. An apparatus according to claim 1, including a first container conveying device for conveying the first container in a cup and in situ to said blood component transferring device.

9. An apparatus according to claim 8, wherein said cup is transparent or translucent.

10. An apparatus according to claim 8, wherein said first container conveying device comprises a rotary drive mechanism composed of a rotator, a plurality of cup retaining parts disposed in the peripheral part of said rotator and each adapted to retain a cup in place, and rotary drive means for imparting a rotary driving motion to said rotator.

11. An apparatus according to claim 8, wherein said first container conveying device comprises a plurality of cup retaining parts each adapted to retain a cup in place, a cup conveying mechanism for removing cups from a centrifuge and seating the cups in one of said cup retaining parts.

12. An apparatus according to claim 8, wherein said first container conveying device includes a first container recovery part for recovering the first container from which transfer of the blood components has been effected.

13. An apparatus according to claim 1, including a container loading part for receiving the second container, with the second container being seated in said container loading part during conveyance of blood components from the first container.

14. An apparatus according to claim 1, including a container feeding device for supplying the second container.

15. An apparatus according to claim 14, wherein said container feeding device comprises a bag accommodating part for accommodating a plurality of second containers which are in the form of bags having a side from which extends a tube so that the bags are orderly superposed in a stack in the bag accommodating part with said side of each bag being posed in one fixed direction, a mounting base disposed near a bottom part of said bag accommodating part for receiving the bags, and a lift for imparting a vertical reciprocating motion to said mounting base and, thereby, enabling said mounting base to be elevated by the action of said lift and permitting an uppermost one of said bags in the stack mounted on said mounting base to be supplied.

16. An apparatus according to claim 15, wherein said mounting base is included so that one end of the mounting base is at a different elevation than the opposite end of the mounting base to thereby impart a prescribed orientation to the uppermost bag in the stack of bags accommodated in said bag accommodating part without reference to the number of bags so accommodated.

17. An apparatus according to claim 15, wherein said mounting base is rotatably disposed at one end part of the mounting base so as to be rotated to vary inclination of the mounting base.

18. An apparatus according to claim 15, wherein said mounting base comprises a plurality of mounting assemblies connected together to form a link mechanism in which each of the mounting assemblies is positionable at a different inclination relative to other mounting assemblies.

19. An apparatus according to claim 15, wherein said lift comprises two drive mechanisms for elevating different portions of said mounting base at different rates of elevation.

20. An apparatus according to claim 15, including a second container conveying device for conveying the second container from said container feeding device to a prescribed position, said second container conveying device comprising a head provided with retaining means for retaining the second container in place and moving means for moving said head in at least two perpendicularly intersecting directions.

21. An apparatus according to claim 20, wherein said retaining means comprises a suction cup for drawing said second container to the suction cup by means of aspiration and decompressing means for reducing the pressure within said suction cup.

22. An apparatus according to claim 20, wherein said second container conveying device is provided with at least one second container recovering part for recovering the second container into which conveyance of said blood components has been effected.

23. An apparatus according to claim 1, including a tube squeeze device for imparting a squeezing action to at least one of the first and second tubes in the longitudinal direction of the tube.

24. An apparatus according to claim 23, wherein said tube squeeze device comprises a tube squeezing part composed of a roller and a counter member, roller rotating means for rotating said roller, and displacing means for varying the distance between said roller and said counter member, said displacing means causing said roller and said counter member to approach each other and close the tube and, at the same time, said roller rotating means causing rotation of said roller, squeezing of the tube to a prescribed length, and movement of liquid in the tube.

25. An apparatus according to claim 23, wherein said tube squeeze device includes a tube squeezing part composed of a roller and a counter member, roller rotating means for rotating said roller, and displacing means for varying the distance between said roller and said counter member, a container loading part for seating the second container in the form of a flexible container having the second tube attached thereto, and control means for controlling said roller rotating means and said displacing means so that said displacing means causes said roller and said counter member to approach each other and compress and close the second tube, so that said roller rotating means rotates said roller squeezes the second tube to a prescribed length, and moves liquid in the second tube toward the second container, and so that said roller rotating means moves said roller and said counter member away from each other to relieve compression on the second tube.

26. An apparatus according to claim 23, wherein said tube squeeze device comprises a tube squeezing part composed of a pair of rollers disposed in opposing relation to each other, roller rotating means for rotating at least one of said rollers, and displacing means for varying the distance between said rollers, a container loading part for seating the second container in the form of a flexible container having the second tube in communication with an interior of the second container, and control means for controlling said roller rotating means and said displacing means so that said displacing means causes said two rollers to approach each other and compress and close the tube and so that, at the same time, the roller rotating means rotates said rollers and squeezes the tube to a prescribed length to move the fluid in the tube toward the second container, and then moves said two rollers away from each other to relieve compression on the tube.

27. An apparatus according to claim 23, wherein said tube squeeze device comprises a tube squeezing part composed of a pair of rollers disposed in opposing relation to each other, roller rotating means for rotating at least one of said rollers, and displacing means for varying the distance between said rollers, a container loading part for seating the second container in the form of a flexible container having the second tube in communication with an interior of the flexible container, stirring means for stirring a liquid in the second container seated on said container loading part, and control means for controlling said displacing means and said stirring means so that said control means causes said two rollers to approach each other and compress and close the second tube and, at the same time, causes said roller rotating means to rotate said roller, squeeze the tube to a prescribed length, and move liquid in the tube toward the second container, then causes said stirring means to stir the liquid in the second container, and thereafter causes said displacing means to move said rollers away from each other to relieve compression on the tube.

28. An apparatus according to claim 27, wherein said stirring means is shaking means for shaking said container loading port.

29. An apparatus according to any of claim 24 to 27, wherein said tube squeeze device terminates squeezing action exerted on the second tube at a position near a joint between the second tube and the second container.

30. An apparatus according to claim 1, including a chemical solution feeding device for introducing a chemical solution into at least one of the first and second containers.

31. An apparatus according to claim 30, wherein said chemical solution feeding device comprises a chemical solution container for storing chemical solution and a third tube communicating with said chemical solution container and allowing the chemical solution in said chemical solution container to be transferred in a prescribed amount to the first container through the first and third tubes after said tube connecting device has interconnected said first and said third tubes.

32. An apparatus according to claim 30, including a roller group for effecting transfer of chemical solution to the first container.

33. An apparatus according to claim 1, wherein said apparatus further comprises control means for controlling at least parts of said apparatus for the manufacture of blood products, which comprises a data processing device for processing information concerning a content of the first container.

34. An apparatus according to claim 33, wherein said data processing device comprises a reader for reading data code applied to the first container and adapted to symbolize said information concerning the content in the first container.

35. An apparatus according to claim 34, wherein said reader is a one-dimensional reader to a two-dimensional reader.

36. An apparatus according to claim 34, wherein said reader is adapted to optically read data code.

37. An apparatus according to claim 34, wherein said reader is adapted to read data code in a flattened state.

38. An apparatus according to claim 34, wherein said data processing device comprises a label producing device for producing a label bearing the data code.

39. An apparatus according to claim 38, wherein said label producing device is a printer for printing said data code on a label.

40. An apparatus according to claim 38, wherein said data processing device comprising a label application device for applying a label produced by said label producing device to said second container.

41. An apparatus according to claim 40, wherein said label application device comprises a pressure head for applying a label with pressure to a surface and moving for moving said pressure head in at least two perpendicularly intersecting directions.

42. An apparatus according to claim 40, wherein said control means controls said data processing device to utilize said reader for reading the data code attached to the first container, controls said label producing device for producing a label having attached thereto the data code corresponding to the data code read by said reader, and controls said label application device for applying the label to the second container.

43. An apparatus according to claim 38, wherein said label has other information indicated thereon besides the information concerning the content.

44. An apparatus according to claim 33, wherein said data processing device comprises a check reader for reading data code on a label attached to the second container.

45. An apparatus according to claim 44, wherein said control means controls said data processing device to utilize said reader for reading the data code attached to said first container, controls said label producing device for producing a label having attached thereto data code corresponding to the information read by said reader, controls said label application device for applying said label to the second container, and controls said check reader for comparing the information read by the check reader with the data code on the label and confirming coincidence therebetween.

46. An apparatus according to claim 45, wherein said control means is adapted to produce an alarm when the control means confirms the absence of coincidence between the information read out by said reader and the information read out by said check reader.

47. An apparatus according to claim 33, wherein said control means comprises flow detecting means for detecting the amount of liquid flowing in and/or flowing out of the first container.

48. An apparatus according to claim 33, wherein said control means comprises a weight detecting means for detecting a change in weight of the second container.

49. An apparatus according to claim 48, wherein said weight detecting means comprises overload releasing means for precluding exertion of an excessive load.

50. An apparatus according to claim 1, wherein the first or second container is comprised of one or more pieces.

51. An apparatus for the manufacture of blood products comprising:

a blood component transferring device for transferring from a first container to a second container at least one of a plurality of separated blood components stored in the first container;

a tube connecting device for aseptically connecting a first tube communicating with the first container to a second tube communicating with the second container to permit said blood component transferring device to transfer at least one blood component stored in the first container to the second container through the interconnected first and second tubes; and a tube conveying device for conveying the first and second tubes in the longitudinal direction of the tubes, said tube conveying device comprising, conveying rails forming a passage for passing the tubes, at least one pair of rollers adapted to chuck and rotate the tubes, and drive means for rotating said rollers.

52. An apparatus according to claim 51, wherein said tube convey device comprises a tube pickup device for retaining said tubes in a taut state.

* * * * *

UNITED STATES PATENT AND TRADEMARK OFFICE
CERTIFICATE OF CORRECTION

PATENT NO. : 5,674,741
DATED : October 7, 1997
INVENTOR(S) : Takahiko WATANABE

It is certified that error appears in the above-identified patent and that said Letters Patent is hereby corrected as shown below:

In Column 2, line 37, after "subjected" insert -- again --.

In Column 9, line 53, delete "sever" and insert -- severe --.

In Column 11, line 16, after "in" and before "tube" insert -- the --.

In Column 12, line 26, delete "1" and insert -- 2 --.

In Column 15, line 58, after "is" and before "a" insert -- in --.

In Column 16, line 10, delete "fir" and insert -- fit --.

In Column 18, line 18, delete "roller" and insert -- rollers --.

In Column 20, line 10, after "232" delete "is" and insert -- in --.

In Column 20, line 51, delete "downward" and insert -- downstream --.

In Column 24, line 63, delete "approximation" and insert -- approximate --.

In Column 26, line 30, delete "used" and insert -- use --.

In Column 26, line 61, delete "out" and insert -- cut --.

In Column 29, line 65, after "above" insert -- , --.

In Column 32, line 14, delete "out" and insert -- cut --.

In Column 44, line 56, delete "through" and insert -- though --.

In Column 50, line 16, delete "the" and insert -- The --.

In Column 66, line 55, after "manufacture" insert -- of --.

In Column 69, line 58, delete "port" and insert -- part --.

UNITED STATES PATENT AND TRADEMARK OFFICE
CERTIFICATE OF CORRECTION

PATENT NO. : 5,674,741
DATED : October 7, 1997
INVENTOR(S) : Takahiko WATANABE

It is certified that error appears in the above-identified patent and that said Letters Patent is hereby corrected as shown below:

In Column 70, line 21, delete "to" and insert -- or --.
In Column 70, line 39, after "moving" and insert -- means --.

Signed and Sealed this

Fourteenth Day of April, 1998

Attest:

BRUCE LEHMAN

Attesting Officer

Commissioner of Patents and Trademarks